(12) United States Patent
Brouns et al.

(10) Patent No.: US 10,435,678 B2
(45) Date of Patent: *Oct. 8, 2019

(54) MODIFIED CASCADE RIBONUCLEOPROTEINS AND USES THEREOF

(71) Applicant: Caribou Biosciences, Inc., Berkeley, CA (US)

(72) Inventors: Stan Johan Jozef Brouns, Wageningen (NL); John Van Der Oost, Renkum (NL)

(73) Assignee: Caribou Biosciences, Inc., Berkeley, CA (US)

( * ) Notice: Subject to any disclaimer, the term of this patent is extended or adjusted under 35 U.S.C. 154(b) by 217 days.

This patent is subject to a terminal disclaimer.

(21) Appl. No.: 15/802,413

(22) Filed: Nov. 2, 2017

(65) Prior Publication Data

US 2018/0119121 A1     May 3, 2018

Related U.S. Application Data

(63) Continuation of application No. 14/997,474, filed on Jan. 15, 2016, now Pat. No. 9,885,026, which is a continuation of application No. 14/326,099, filed on Jul. 8, 2014, now abandoned, which is a continuation of application No. 14/240,735, filed as application
(Continued)

(30) Foreign Application Priority Data

Dec. 30, 2011 (GB) .................................. 1122458.1

(51) Int. Cl.
| | |
|---|---|
| C12N 9/22 | (2006.01) |
| C07K 14/245 | (2006.01) |
| A61K 48/00 | (2006.01) |
| C12N 9/16 | (2006.01) |
| C12N 15/74 | (2006.01) |
| C12N 15/62 | (2006.01) |
| C12N 15/70 | (2006.01) |
| C12N 15/81 | (2006.01) |
| C12N 15/82 | (2006.01) |
| C12N 15/86 | (2006.01) |
| C12N 15/90 | (2006.01) |
| C07K 14/47 | (2006.01) |
| C12N 15/66 | (2006.01) |
| A61K 38/00 | (2006.01) |

(52) U.S. Cl.
CPC ............. *C12N 9/22* (2013.01); *A61K 48/005* (2013.01); *C07K 14/245* (2013.01); *C07K 14/47* (2013.01); *C12N 9/16* (2013.01); *C12N 15/62* (2013.01); *C12N 15/66* (2013.01); *C12N 15/70* (2013.01); *C12N 15/74* (2013.01); *C12N 15/81* (2013.01); *C12N 15/82* (2013.01); *C12N 15/86* (2013.01); *C12N 15/902* (2013.01); *C12N 15/907* (2013.01); *A61K 38/00* (2013.01); *C07K 2319/09* (2013.01); *C07K 2319/22* (2013.01); *C07K 2319/60* (2013.01); *C07K 2319/71* (2013.01); *C07K 2319/80* (2013.01); *C07K 2319/85* (2013.01); *C12N 2310/20* (2017.05); *C12Y 301/21004* (2013.01)

(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 5,489,677 | A | 2/1996 | Sanghvi et al. |
| | | (Continued) | |

FOREIGN PATENT DOCUMENTS

| | | | |
|---|---|---|---|
| CN | 103224947 A | | 7/2013 |
| CN | 103233028 A | | 8/2013 |
| | (Continued) | | |

OTHER PUBLICATIONS

Makarova et al. (2011) Evolution and classification of the CRISPR-Cas systems. Nature Reviews Microbiology, 9(6):467-477 (Year: 2011).*

(Continued)

*Primary Examiner* — Neil P Hammell
(74) *Attorney, Agent, or Firm* — Gary R. Fabian; Barbara G. McClung

(57) ABSTRACT

A clustered regularly interspaced short palindromic repeat (CRISPR)-associated complex for adaptive antiviral defence (Cascade); the Cascade protein complex comprising at least CRISPR-associated protein subunits Cas7, Cas5 and Cas6 which includes at least one subunit with an additional amino acid sequence possessing nucleic acid or chromatin modifying, visualizing, transcription activating or transcription repressing activity. The Cascade complex with additional activity is combined with an RNA molecule to produce a ribonucleoprotein complex. The RNA molecule is selected to have substantial complementarity to a target sequence. Targeted ribonucleoproteins can be used as genetic engineering tools for precise cutting of nucleic acids in homologous recombination, non-homologous end joining, gene modification, gene integration, mutation repair or for their visualization, transcriptional activation or repression. A pair of ribonucleotides fused to FokI dimers may be used to generate double-strand breakages in the DNA to facilitate these applications in a sequence-specific manner.

11 Claims, 25 Drawing Sheets
Specification includes a Sequence Listing.

Related U.S. Application Data

No. PCT/EP2012/076674 on Dec. 21, 2012, now abandoned.

(56) References Cited

U.S. PATENT DOCUMENTS

| | | | |
|---|---|---|---|
| 5,602,240 | A | 2/1997 | De Mesmaeker et al. |
| 5,766,900 | A | 6/1998 | Shillito et al. |
| 5,767,367 | A | 6/1998 | Dudits et al. |
| 5,968,738 | A | 10/1999 | Anderson et al. |
| 6,066,476 | A | 5/2000 | Tsien et al. |
| 6,306,610 | B1 | 10/2001 | Bawendi et al. |
| 7,919,277 | B2 | 4/2011 | Russell et al. |
| 8,361,725 | B2 | 1/2013 | Russell et al. |
| 8,546,553 | B2 | 10/2013 | Terns et al. |
| 8,685,737 | B2 | 4/2014 | Serber et al. |
| 8,697,359 | B1 | 4/2014 | Zhang |
| 8,771,945 | B1 | 7/2014 | Zhang |
| 8,795,965 | B2 | 8/2014 | Zhang |
| 8,921,332 | B2 | 12/2014 | Choulika et al. |
| 2002/0119570 | A1 | 8/2002 | Yoon et al. |
| 2002/0182673 | A1 | 12/2002 | Chen et al. |
| 2003/0232410 | A1 | 12/2003 | Lilhedahl et al. |
| 2004/0111221 | A1 | 6/2004 | Beattie et al. |
| 2005/0026157 | A1 | 2/2005 | Baltimore et al. |
| 2005/0208489 | A1 | 9/2005 | Carroll et al. |
| 2006/0147980 | A1 | 7/2006 | Keene et al. |
| 2006/0199190 | A1 | 9/2006 | Russell et al. |
| 2006/0253913 | A1 | 11/2006 | Huang et al. |
| 2007/0016012 | A1 | 1/2007 | Hartlep et al. |
| 2007/0134796 | A1 | 6/2007 | Holmes et al. |
| 2007/0218528 | A1 | 9/2007 | Miller et al. |
| 2008/0124725 | A1 | 5/2008 | Barrangou et al. |
| 2008/0159996 | A1 | 7/2008 | Ando et al. |
| 2009/0227029 | A1 | 9/2009 | Radman et al. |
| 2010/0034924 | A1 | 2/2010 | Fremaux et al. |
| 2010/0047805 | A1 | 2/2010 | Wang et al. |
| 2010/0055728 | A1 | 3/2010 | Yang et al. |
| 2010/0076057 | A1 | 3/2010 | Sontheimer et al. |
| 2010/0093617 | A1 | 4/2010 | Barrangou et al. |
| 2010/0104690 | A1 | 4/2010 | Barrangou et al. |
| 2011/0002889 | A1 | 1/2011 | Barrangou et al. |
| 2011/0041195 | A1 | 2/2011 | Doyon |
| 2011/0082093 | A1 | 4/2011 | Gregory et al. |
| 2011/0105364 | A1 | 5/2011 | Kurn |
| 2011/0145940 | A1 | 6/2011 | Voytas et al. |
| 2011/0182867 | A1 | 7/2011 | Orkin et al. |
| 2011/0189776 | A1 | 8/2011 | Terns et al. |
| 2011/0203012 | A1 | 8/2011 | Dotson et al. |
| 2011/0207221 | A1 | 8/2011 | Cost et al. |
| 2011/0217739 | A1 | 9/2011 | Terns et al. |
| 2011/0223638 | A1 | 9/2011 | Wiedenheft et al. |
| 2011/0236530 | A1 | 9/2011 | Manoury et al. |
| 2011/0287545 | A1 | 11/2011 | Cost et al. |
| 2011/0294114 | A1 | 12/2011 | Van Der Loo et al. |
| 2011/0300538 | A1 | 12/2011 | Barrangou et al. |
| 2011/0301073 | A1 | 12/2011 | Gregory et al. |
| 2012/0029891 | A1 | 2/2012 | Behlke et al. |
| 2012/0149115 | A1 | 6/2012 | Kim et al. |
| 2012/0192298 | A1 | 7/2012 | Weinstein et al. |
| 2012/0196370 | A1 | 8/2012 | Urnov et al. |
| 2012/0230971 | A1 | 9/2012 | Choulika et al. |
| 2012/0324603 | A1 | 12/2012 | Hlubek et al. |
| 2013/0011828 | A1 | 1/2013 | Barrangou et al. |
| 2013/0017541 | A1 | 1/2013 | Forsyth |
| 2013/0065310 | A1 | 3/2013 | Davis et al. |
| 2013/0130248 | A1 | 5/2013 | Haurwitz et al. |
| 2013/0145497 | A1 | 6/2013 | Choi et al. |
| 2013/0158245 | A1 | 6/2013 | Russell et al. |
| 2013/0253040 | A1 | 9/2013 | Miller et al. |
| 2013/0288251 | A1 | 10/2013 | Horvath et al. |
| 2013/0326645 | A1 | 12/2013 | Cost et al. |
| 2013/0326725 | A1 | 12/2013 | Shukla et al. |
| 2013/0330778 | A1 | 12/2013 | Gusti et al. |
| 2014/0017212 | A1 | 1/2014 | Rebar et al. |
| 2014/0017214 | A1 | 1/2014 | Cost |
| 2014/0045176 | A1 | 2/2014 | Kim et al. |
| 2014/0068797 | A1 | 3/2014 | Doudna et al. |
| 2014/0080216 | A1 | 3/2014 | Cost et al. |
| 2014/0090112 | A1 | 3/2014 | Cogan et al. |
| 2014/0090113 | A1 | 3/2014 | Cogan et al. |
| 2014/0090116 | A1 | 3/2014 | Ainley et al. |
| 2014/0112896 | A1 | 4/2014 | Rebar et al. |
| 2014/0123330 | A1 | 5/2014 | Carlson et al. |
| 2014/0127752 | A1 | 5/2014 | Zhou et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0186958 | A1 | 7/2014 | Cong et al. |
| 2014/0189896 | A1 | 7/2014 | Bikard et al. |
| 2014/0199767 | A1 | 7/2014 | Barrangou et al. |
| 2014/0294773 | A1 | 10/2014 | Brouns et al. |
| 2014/0295556 | A1 | 10/2014 | Joung et al. |
| 2015/0024499 | A1 | 1/2015 | Brouns et al. |

FOREIGN PATENT DOCUMENTS

| | | |
|---|---|---|
| CN | 103343120 A | 10/2013 |
| EP | 2292731 A1 | 3/2011 |
| EP | 2341149 A1 | 7/2011 |
| EP | 2489275 A1 | 8/2012 |
| EP | 2674501 A1 | 12/2013 |
| WO | WO 88/08450 A1 | 11/1988 |
| WO | WO 93/19191 A1 | 9/1993 |
| WO | WO 02/34771 A3 | 5/2002 |
| WO | WO 2006/073445 A2 | 7/2006 |
| WO | WO 2007/025097 A2 | 3/2007 |
| WO | WO 2007/136815 A2 | 11/2007 |
| WO | WO 2007/144770 A2 | 12/2007 |
| WO | WO 2008/108989 A2 | 9/2008 |
| WO | WO 2009/115861 A2 | 9/2009 |
| WO | WO 2010/011961 A2 | 1/2010 |
| WO | WO 2010/054108 A2 | 5/2010 |
| WO | WO 2010/054154 A2 | 5/2010 |
| WO | WO 2010/066907 A1 | 6/2010 |
| WO | WO 2010/075424 A2 | 7/2010 |
| WO | WO 2010/117464 A1 | 10/2010 |
| WO | WO 2010/125471 A2 | 11/2010 |
| WO | WO 2011/011767 A1 | 1/2011 |
| WO | WO 2011/143124 A2 | 11/2011 |
| WO | WO 2011/156430 A2 | 12/2011 |
| WO | WO 2012/012738 A1 | 1/2012 |
| WO | WO 2012/054726 A1 | 4/2012 |
| WO | WO 2012/164565 A1 | 12/2012 |
| WO | WO 2013/044008 A2 | 3/2013 |
| WO | WO 2013/082519 A2 | 6/2013 |
| WO | WO 2013/088446 A1 | 6/2013 |
| WO | WO 2013/098244 A1 | 7/2013 |
| WO | WO 2013/126794 A1 | 8/2013 |
| WO | WO 2013/130824 A1 | 9/2013 |
| WO | WO 2013/141680 A1 | 9/2013 |
| WO | WO 2013/142578 A1 | 9/2013 |
| WO | WO 2013/155572 A1 | 10/2013 |
| WO | WO 2013/160230 A1 | 10/2013 |
| WO | WO 2013/169398 A2 | 11/2013 |
| WO | WO 2013/169802 A1 | 11/2013 |
| WO | WO 2013/176772 A1 | 11/2013 |
| WO | WO 2013/181440 A1 | 12/2013 |
| WO | WO 2013/186754 A3 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2014/011237 A1 | 1/2014 |
| WO | WO 2014/011901 A2 | 1/2014 |
| WO | WO 2014/018423 A2 | 1/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2013/188522 A2 | 4/2014 |
| WO | WO 2014/059255 A1 | 4/2014 |
| WO | WO 2014/065596 A1 | 5/2014 |
| WO | WO 2014/071006 A1 | 5/2014 |

(56) References Cited

FOREIGN PATENT DOCUMENTS

| | | |
|---|---|---|
| WO | WO 2014/089290 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/113493 A1 | 7/2014 |

OTHER PUBLICATIONS

Carroll et al. (2011) Genome Engineering With Zinc-Finger Nucleases. Genetics, 188:773-782 (Year: 2011).*
Zhao et al. (2008) Increasing the homogeneity, stability and activity of human serum albumin and interferon-a2b fusion protein by linker engineering. Protein Expression and Purification, 61:73-77 (Year: 2008).*
Haft et al. A Guild of 45 CRISPR-Associated (Cas) Protein Families and Multiple CRISPR/Cas Subtypes Exist in Prokaryotic Genomes, 1(6) PLoS Comput. Biol. 474-483 (2005).
Hale, et al. RNA-Guided RNA Cleavage by a CRISPR RNA-Cas Protein, 139(5) Cell 945-956 (2009).
Haurwitz, et al. Sequence- and structure-specific RNA processing by a CRISPR endonuclease, 329 Science 1355-1358 (2010).
Mojica, et al. Biological significance of a family of regularly spaced repeats in the genomes of Archaea, Bacteria and mitochondria, 36(1) Mol. Microbiol. 244-246 (2000).
Pourcel, et al. CRISPR elements in Yersinia pestis acquire new repeats by preferential uptake of bacteriophage DNA, and provide additional tools for evolutionary studies, 151 Microbiol. Read. Engl. 653-663 (2005).
Cong et al. (2013) Multiplex Genome Engineering Using CRISPR/Cas Systems. Science, 339:819-823, and supplementary materials.
Mojica et al. (2009) Short motif sequences determine the targets of the prokaryotic CRISPR defence system. Microbiology, 155:733-740, and Supplementary info, 37 pages.
Morton et al. (2006) Induction and repair of zinc-finger nuclease-targeted double-strand breaks in Caenorhabditis elegans somatic cells. PNAS 103(44):16370-16375, and supplementary materials.
Watters. "In Situ Hybridization", in: Walker et al., Medical Biomethods Handbook (New Jersey, Humana Press, 2005), pp. 409-418.
Brouns, S., et al., "Small CRISPR RNAs guide antiviral defense in prokaryotes," Science 321:960-964 (2008).
Caccavo, et al., "*Geobacter sulfurreducens* sp. nov., a Hydrogen- and Acetate-Oxidizing Dissimilatory Metal-Reducing Microorganism," Applied and Environmental Microbiology 60(10):3752-3759 (1994).
Choudhury, R., et al., "Engineering RNA endonucleases with customized sequence specificities," Nat. Commun. 3:1147 (2012). doi: 10.1038/ncomms2154.
Guilinger, J., et al., "Fusion of catalytically inactive Cas9 to FokI nuclease improves the specificity of genome modification," Nat Biotechnol. 32(6):577-582 (2014). Epub Apr. 25, 2014. doi: 10.1038/nbt.2909.
Hochstrasser, M., et al., "DNA targeting by a minimal CRISPR RNA-guided Cascade," Mol. Cell. 63(5):840-851 (2016). doi: 10.1016/j.molcel.2016.07.027.
Jackson, R., et al., "Crystal structure of the CRISPR RNA-guided surveillance complex from *Escherichia coli*," Science 345:1473-1479 (2014).
Jinek, M., et al., "A programmable dual-RNA-guided DNA endonuclease in adaptive bacterial immunity," Science 337(6096):816-821 (2012). Epub Jun. 28, 2012. doi: 10.1126/science.1225829.
Jore, M., et al., "Structural basis for CRISPR RNA-guided DNA recognition by Cascade," Nature Structural & Molecular Biology 18:529-537 (2011).
Kim, Y.G., et al., "Site-specific cleavage of DNA-RNA hybrids by zinc finger/FokI cleavage domain fusions," Gene 203(1):43-49 (1997).
Klein, et al., "Design and characterization of structured protein linkers with differing flexibilities," Protein Engineering, Design & Selection 27(10):325-330 (2014).
Methe, et al., "Genome of Geobacter sulfurreducens: Metal Reduction in Subsurface Environments," Science 302:1967-1969 (2003).
NC_002939.5 (Geobacter sulfurreducens PCA chromosome, complete genome, nucleotide positions 72629-74308, priority to Aug. 3, 2016, 2 pages).
NC_002939.4 (Geobacter sulfurreducens PCA chromosome, complete genome, nucleotide positions 72630-74309, priority to Oct. 14, 2010, 2 pages).
NZ_GG657742.1 (*Streptomyces* sp. SPB78 genomic scaffold supercont 1.1, whole genome shotgun sequence, NCBI Reference Sequence, nucleotide positions 3502816-3507630, priority to Oct. 26, 2010, 3 pages).
Pingoud, et al., "Type II restriction endonucleases—a historical perspective and more," Nucleic Acids Research 42(12):7489-7527 (2014).
Redding, S., et al., "Surveillance and processing of foreign DNA by the *Escherichia coli* CRISPR-Cas system," Cell 163(4):854-865 (2015). doi: 10.1016/j.cell.2015.10.003.
Rittie, et al., "Enzymes used in molecular biology: a useful guide," Journal of Cell Communication and Signaling 2(1):25-45 (2008).
Sashital, D., et al., "Mechanism of foreign DNA selection in a bacterial adaptive immune system," Mol. Cell 46:606-615 (2012).
Sinkunas, T., et al., "Cas3 is a single-stranded DNA nuclease and ATP-dependent helicase in the CRISPR/Cas immune system," EMBO J. 30(7):1335-1342 (2011). Epub Feb. 22, 2011. doi: 10.1038/emboj.2011.41.
Sinkunas, T., et al., "In vitro reconstitution of Cascade-mediated CRISPR immunity in *Streptococcus thermophilus*," EMBO J. 32(3):385-394 (2013). Epub Jan. 18, 2013. doi: 10.1038/emboj.2012.352.
Wiedenheft, B., et al., "Structures of the RNA-guided surveillance complex from a bacterial immune system," Nature 477(7365):486-489 (2011). doi: 10.1038/nature10402.
Zhao, et al., "Increasing the homogeneity, stability and activity of human serum albumin and interferon-alpha2b fusion protein by linker engineering," Protein Expression and Purification, 61:73-77 (2008).
U.S. Appl. No. 14/240,735, filed Feb. 24, 2014, Brouns et al.
Aguilera, et al. Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Amantana, et al. Pharmacokinetics, biodistribution, stability and toxicity of a cell-penetrating peptide-morpholino oligomer conjugate. Bioconjug Chem. Jul.-Aug. 2007;18(4):1325-31. Epub Jun. 21, 2007.
Barrangou, R. RNA-mediated programmable DNA cleavage. Nat Biotechnol. Sep. 2012;30(9):836-8. doi: 10.1038/nbt.2357.
Bassett, et al. Highly Efficient Targeted Mutagenesis of *Drosophila* with the CRISPR/Cas9 System. Cell Rep. Jul. 11, 2013;4(1):220-8. doi: 10.1016/j.celrep.2013.06.020. Epub Jul. 1, 2013.
Bhaya, et al. CRISPR-Cas systems in bacteria and archaea: versatile small RNAs for adaptive defense and regulation. Annu Rev Genet. 2011;45:273-97. doi: 10.1146/annurev-genet-110410-132430.
Brouns, et al. Small CRISPR RNAs guide antiviral defense in prokaryotes. Science. Aug. 15, 2008;321(5891):960-4. doi: 10.1126/science.1159689.
Carr, et al. Genome engineering. Nat Biotechnol. Dec. 2009 ;27(12):1151-62. doi: 10.1038/nbt.1590.
Carte, et al. Cas6 is an endoribonuclease that generates guide RNAs for invader defense in prokaryotes. Genes Dev. Dec. 15, 2008;22(24):3489-96. doi: 10.1101/gad.1742908.
Cho, et al. Targeted genome engineering in human cells with the Cas9 RNA-guided endonuclease. Nat Biotechnol. Mar. 2013;31(3):230-2. doi: 10.1038/nbt.2507. Epub Jan. 29, 2013.

(56) References Cited

OTHER PUBLICATIONS

Chylinski, et al. The tracrRNA and Cas9 families of type II CRISPR-Cas immunity systems. RNA Biol. May 2013;10(5):726-737. doi: 10.4161/rna.24321. Epub Apr. 5, 2013.
Cong, et al. Multiplex genome engineering using CRISPR/Cas systems. Science. Feb. 15, 2013;339(6121):819-23. doi: 10.1126/science.1231143. Epub Jan. 3, 2013.
Dame, et al. H-NS mediated compaction of DNA visualised by atomic force microscopy. Nucleic Acids Res. Sep. 15, 2000;28(18):3504-10.
Dekelver, et al. Functional genomics, proteomics, and regulatory DNA analysis in isogenic settings using zinc finger nuclease-driven transgenesis into a safe harbor locus in the human genome. Genome Res. Aug. 2010;20(8):1133-42. doi: 10.1101/gr.106773.110. Epub May 27, 2010.
Deltcheva, et al. CRISPR RNA maturation by trans-encoded small RNA and host factor RNase III. Nature. Mar. 31, 2011;471(7340):602-7. doi: 10.1038/nature09886.
Donnelly, et al. The 'cleavage' activities of foot-and-mouth disease virus 2A site-directed mutants and naturally occurring '2A-like' sequences. J Gen Virol. May 2001;82(Pt 5):1027-41.
Doyon, et al. Enhancing zinc-finger-nuclease activity with improved obligate heterodimeric architectures. Nat Methods. Jan. 2011;8(1):74-9. doi: 10.1038/nmeth.1539. Epub Dec. 5, 2010.
Drag, et al. DeSUMOylating enzymes—SENPs. IUBMB Life. Nov. 2008;60(11):734-42. doi: 10.1002/iub.113.
Fineran, et al. Degenerate target sites mediate rapid primed CRISPR adaptation. Proc Natl Acad Sci U S A. Apr. 22, 2014;111(16):E1629-38. doi: 10.1073/pnas.1400071111. Epub Apr. 7, 2014.
Friedland, et al. Heritable genome editing in C. elegans via a CRISPR-Cas9 system. Nat Methods. Aug. 2013;10(8):741-3. doi: 10.1038/nmeth.2532. Epub Jun. 30, 2013.
Fu, et al. High-frequency off-target mutagenesis induced by CRISPR-Cas nucleases in human cells. Nat Biotechnol. Jun. 23, 2013. doi: 10.1038/nbt.2623. [Epub ahead of print].
Gasiunas, et al. Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.
Grissa, et al. The CRISPRdb database and tools to display CRISPRs and to generate dictionaries of spacers and repeats. BMC Bioinformatics. May 23, 2007;8:172.
Guo, et al. Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guschin, et al. A rapid and general assay for monitoring endogenous gene modification. Methods Mol Biol. 2010;649:247-56. doi: 10.1007/978-1-60761-753-2_15.
Haft, et al. A guild of 45 CRISPR-associated (Cas) protein families and multiple CRISPR/Cas subtypes exist in prokaryotic genomes. PLoS Comput Biol. Nov. 2005;1(6):e60. Epub Nov. 11, 2005.
Hale, et al. Essential features and rational design of CRISPR RNAs that function with the Cas RAMP module complex to cleave RNAs. Mol Cell. Feb. 10, 2012;45(3):292-302. doi: 10.1016/j.molcel.2011.10.023. Epub Jan. 5, 2012.
Hale, et al. RNA-Guided RNA Cleavage by a CRISPR RNA-Cas Protein Complex. Cell. Nov. 25, 2009; 139(5): 945-956.
Haurwitz, et al. The CRISPR endoribonuclease Csy4 utilizes unusual sequence and 17 structure-specific mechanisms to recognize and process crRNAs. Electronic Thesis and Dissertations UC Berkley, pp. 1-108. Spring 2012. entire document URL: <http://escholarship.org/uc/item/0rh5940p>.
Heasman. Morpholino oligos: making sense of antisense? Dev Biol. Mar. 15, 2002;243(2):209-14.
Horvath, et al. CRISPR/Cas, the immune system of bacteria and archaea. Science. Jan. 8, 2010;327(5962):167-70. doi: 10.1126/science.1179555.

Hou, et al. Efficient genome engineering in human pluripotent stem cells using Cas9 from *Neisseria meningitidis*. oc Natl Acad Sci U S A. Sep. 24, 2013;110(39):15644-9. doi: 10.1073/pnas.1313587110. Epub Aug. 12, 2013.
Hsu, et al. DNA targeting specificity of RNA-guided Cas9 nucleases. Nat Biotechnol. Jul. 21, 2013. doi: 10.1038/nbt.2647. [Epub ahead of print].
Huang, et al. A simple, high sensitivity mutation screening using Ampligase mediated T7 endonuclease I and Surveyor nuclease with microfluidic capillary electrophoresis. Electrophoresis. Mar. 2012;33(5):788-96. doi: 10.1002/elps.201100460. Epub Mar. 21, 2012.
Hudziak, et al. Resistance of morpholino phosphorodiamidate oligomers to enzymatic degradation. Antisense Nucleic Acid Drug Dev. 1996 Winter;6(4):267-72.
Hwang, et al. Efficient genome editing in zebrafish using a CRISPR-Cas system. Nat Biotechnol. Mar. 2013;31(3):227-9. doi: 10.1038/nbt.2501. Epub Jan. 29, 2013.
International search report and written opinion dated Jun. 16, 2014 for PCT/US2014/023828.
International search report and written opinion dated Jul. 26, 2013 for PCT/US2013/032589.
International search report dated Mar. 7, 2013 for PCT Application No. EP2012/07664.
Jansen, et al. Identification of genes that are associated with DNA repeats in prokaryotes. Mol Microbiol. Mar. 2002;43(6):1565-75.
Jiang, et al. RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek, et al. A programmable dual-RNA-guided DNA endonuclease in adaptive bacterial immunity Science. Aug. 17, 2012;337(6096):816-21. doi: 10.1126/science.1225829. Epub Jun. 28, 2012.
Jinek, et al. RNA-programmed genome editing in human cells. Elife. 2013;2:e00471. doi: 10.7554/eLife.00471. Epub Jan. 29, 2013.
Jore, et al. Structural basis for CRISPR RNA-guided DNA recognition by Cascade. Nat Struct Mol Biol. May 2011;18(5):529-36. doi: 10.1038/nsmb.2019. Epub Apr. 3, 2011.
Kunin, et al. Evolutionary conservation of sequence and secondary structures in CRISPR repeats. Genome Biol. 2007;8(4):R61.
Lillestol, et al. A putative viral defence mechanism in archaeal cells. Archaea. Aug. 2006;2(1):59-72.
Lillestol, et al. CRISPR families of the *crenarchaeal* genus Sulfolobus: bidirectional transcription and dynamic properties. Mol Microbiol. Apr. 2009;72(1):259-72. doi: 10.1111/j.1365-2958.2009.06641.x. Epub Feb. 23, 2009.
Lintner, et al. Structural and functional characterization of an archaeal clustered regularly interspaced short palindromic repeat (CRISPR)-associated complex for antiviral defense (CASCADE). J Biol Chem. Jun. 17, 2011;286(24):21643-56. doi: 10.1074/jbc.M111.238485. Epub Apr. 20, 2011.
Makarova, et al. A putative RNA-interference-based immune system in prokaryotes: computational analysis of the predicted enzymatic machinery, functional analogies with eukaryotic RNAi, and hypothetical mechanisms of action. Biology Direct 2006, 1:7.
Makarova, et al. Evolution and classification of the CRISPR-Cas systems. Nat Rev Microbiol. Jun. 2011;9(6):467-77. doi: 10.1038/nrmicro2577. Epub May 9, 2011.
Makarova, et al. Unification of Cas protein families and a simple scenario for the origin and evolution of CRISPR-Cas systems. Biol Direct. Jul. 14, 2011;6:38. doi: 10.1186/1745-6150-6-38.
Makinen, et al. Stable RNA interference: comparison of U6 and H1 promoters in endothelial cells and in mouse brain. J Gene Med. Apr. 2006;8(4):433-41.
Mali, et al. RNA-guided human genome engineering via Cas9. Science. Feb. 15, 2013;339(6121):823-6. doi: 10.1126/science.1232033. Epub Jan. 3, 2013.
Marraffini, et al. CRISPR interference limits horizontal gene transfer in *staphylococci* by targeting DNA. Science. Dec. 19, 2008;322(5909):1843-5. doi: 10.1126/science.1165771.
Marraffini, et al. CRISPR interference: RNA-directed adaptive immunity in bacteria and archaea. Nat Rev Genet. Mar. 2011; 11(3):181-90. doi: 10.1038/nrg2749.

(56) References Cited

OTHER PUBLICATIONS

Melton, et al. Efficient in vitro synthesis of biologically active RNA and RNA hybridization probes from plasmids containing a bacteriophage SP6 promoter. Nucleic Acids Res. Sep. 25, 1984;12(18):7035-56.

Morcos, et al. Vivo-Morpholinos: A non-peptide transported delivers morpholinos into a wide array of mouse tissues. Biotechniques. Dec. 2008;45(6):613-4, 616, 618 passim.

Nagai, et al. A variant of yellow fluorescent protein with fast and efficient maturation for cell-biological applications. Nat Biotechnol. Jan. 2002;20(1):87-90.

Nishimasu, et al. Crystal Structure of Cas9 in Complex with Guide RNA and Target DNA. Cell. 2014;156(5):935-949.

Niu, et al. Generation of Gene-Modified Cynomolgus Monkey via Cas9/RNA-Mediated Gene Targeting in One-Cell Embryos. Cell. Feb. 13, 2014;156(4):836-43. doi: 10.1016/j.cell.2014.01.027. Epub Jan. 30, 2014.

Olson, et al. In vivo characterization of activatable cell penetrating peptides for targeting protease activity in cancer. Integr Biol (Camb). Jun. 2009;1(5-6):382-93. doi: 10.1039/b904890a. Epub May 11, 2009.

Partridge, et al. A simple method for delivering morpholino antisense oligos into the cytoplasm of cells. Antisense Nucleic Acid Drug Dev. 1996 Fall;6(3):169-75.

Perez-Rodriguez, et al. Envelope stress is a trigger of CRISPR RNA-mediated DNA silencing in *Escherichia coli*. Mol Microbiol. Feb. 2011;79(3):584-99. doi: 10.1111/j.1365-2958.2010.07482.x. Epub Dec. 13, 2010.

Qi, et al. Repurposing CRISPR as an RNA-guided platform for sequence-specific control of gene expression. Cell. Feb. 28, 2013;152(5):1173-83. doi: 10.1016/j.cell.2013.02.022.

Ryan, et al. Cleavage of foot-and-mouth disease virus polyprotein is mediated by residues located within a 19 amino acid sequence. J Gen Virol. Nov. 1991;72 ( Pt 11):2727-32.

Sapranauskas, et al. The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.

Sashital, et al. Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.

SBI. PrecisionX Cas9 SmartNuclease vector system user manual. System Biosciences. 2013.

Semenova, et al. Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.

Sigma-Aldrich. Cas9-GFP Expression Plasmids. Product information. 2013.

Sorek, et al. CRISPR—a widespread system that provides acquired resistance against phages in bacteria and archaea. Nat Rev Microbiol. Mar. 2008;6(3):181-6.

Subach, et al. Conversion of red fluorescent protein into a bright blue probe. Chem Biol. Oct. 20, 2008;15(10):1116-24. doi: 10.1016/j.chembiol.2008.08.006.

Summerton, et al. Morpholino antisense oligomers: design, preparation, and properties.Antisense Nucleic Acid Drug Dev. Jun. 1997;7(3):187-95.

Summerton. Morpholino antisense oligomers: the case for an RNase H-independent structural type. Biochim Biophys Acta. Dec. 10, 1999;1489(1):141-58.

Tahallah, et al. The effect of the source pressure on the abundance of ions of noncovalent protein assemblies in an electrospray ionization orthogonal time-of-flight instrument. Rapid Commun Mass Spectrom. 2001;15(8):596-601.

Tanaka, et al. Conformational variations in an infectious protein determine prion strain differences. Nature. Mar. 18, 2004;428(6980):323-8.

Tang, et al. Identification of 86 candidates for small non-messenger RNAs from the archaeon Archaeoglobus fulgidus. Proc Natl Acad Sci U S A. May 28, 2002;99(11):7536-41.

Tang, et al. Identification of novel non-coding RNAs as potential antisense regulators in the archaeon Sulfolobus solfataricus. Mol Microbiol. Jan. 2005;55(2):469-81.

Terns, et al. CRISPR-based adaptive immune systems. Curr Opin Microbiol. Jun. 2011;14(3):321-7. doi: 10.1016/j.mib.2011.03.005. Epub Apr. 29, 2011.

Urnov, et al. Genome editing with engineered zinc finger nucleases. Nat Rev Genet. Sep. 2010;11(9):636-46. doi: 10.1038/nrg2842.

Van Den Heuvel, et al. Improving the performance of a quadrupole time-of-flight instrument for macromolecular mass spectrometry. Anal Chem. Nov. 1, 2006;78(21):7473-83.

Van Der Oost, et al. CRISPR-based adaptive and heritable immunity in prokaryotes. Trends Biochem Sci. Aug. 2009;34(8):401-7. doi: 10.1016/j.tibs.2009.05.002. Epub Jul. 29, 2009.

Wang, et al. One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

Westra, et al. Cascade-mediated binding and bending of negatively supercoiled DNA. RNA Biol. Sep. 2012;9(9):1134-8. doi: 10.4161/rna.21410. Epub Sep. 1, 2012.

Westra, et al. H-NS-mediated repression of CRISPR-based immunity in *Escherichia coli* K12 can be relieved by the transcription activator LeuO. Mol Microbiol. Sep. 2010;77(6):1380-93. doi: 10.1111/j.1365-2958.2010.07315.x. Epub Aug. 18, 2010.

Wiedenheft, et al. RNA-guided genetic silencing systems in bacteria and archaea. Nature. Feb . 15, 2012;482(7385):331-8. doi: 10.1038/nature10886.

Wiedenheft, et al. Structural basis for DNase activity of a conserved protein implicated in CRISPR-mediated genome defense. Structure. Jun. 10, 2009;17(6):904-12. doi: 10.1016/j.str.2009.03.019.

Wiedenheft, et al. Structures of the RNA-guided surveillance complex from a bacterial immune system. Nature. Sep. 21, 2011;477(7365):486-9. doi: 10.1038/nature10402.

Xia, et al. Bioluminescence of *Aequorea macrodactyla*, a common jellyfish species in the East China Sea. Mar Biotechnol (NY). Mar. 2002;4(2):155-62.

Al-Attar, et al. Clustered regularly interspaced short palindromic repeats (CRISPRs): the hallmark of an ingenious antiviral defense mechanism in prokaryotes. Biol Chem. Apr. 2011;392(4):277-89. doi: 10.1515/BC.2011.042. Epub Feb. 7, 2011.

Anguela, et al. In Vivo Genome Editing of Liver Albumin for Therapeutic Gene Expression: Rescue of Hemophilic Mice via Integration of Factor 9. 54th ASH Annual Meeting and Exposition, Dec. 10, 2012, Atlanta, Georgia.

Barranger, et al. Gene transfer approaches to the lysosomal storage disorders. Neurochem Res. Apr. 1999;24(4):601-15.

Barrangou, et al. CRISPR Provides Acquired Resistance Against Viruses in Prokaryotes. Science, 2007, vol. 313, pp. 1709-1712.

Barras. Right on Target: New Era of Fast Genetic Engineering. New Scientist, Jan. 2014, vol. 2953.

Beloglazova, et al. A novel family of sequence-specific endoribonucleases associated with the clustered regularly interspaced short palindromic repeats. J Biol Chem. Jul. 18, 2008;283(29):20361-71. doi: 10.1074/jbc.M803225200. Epub May 15, 2008.

Beres et al. Genome sequence of a serotype M3 strain of group A *Streptococcus*: phage-encoded toxins, the high-virulence phenotype, and clone emergence. Proc Natl Acad Sci U S A. Jul. 23, 2002;99(15):10078-83. Epub Jul. 16, 2002.

Biffi, et al. Genetically-modified hematopoietic stem cells and their progeny for widespread and efficient protein delivery to diseased sites: the case of lysosomal storage disorders. Curr Gene Ther. Oct. 2012;12(5):381-8.

Biffi, et al. Metachromatic Leukodystrophy: an Overview of Current and Prospective Treatments. Bone Marrow Transplantation, 2008, vol. 42, pp. S2-S6.

Bolotin, et al. Clustered regularly interspaced short palindrome repeats (CRISPRs) have spacers of extrachromosomal origin. Microbiology. Aug. 2005;151(Pt 8):2551-61.

(56) References Cited

OTHER PUBLICATIONS

Bolotin, et al. Complete sequence and comparative genome analysis of the dairy bacterium *Streptococcus thermophilus*. Nat Biotechnol. Dec. 2004;22(12):1554-8. Epub Nov. 14, 2004.

Carroll. A CRISPR approach to gene targeting. Mol Ther. Sep. 2012;20(9):1658-60. doi: 10.1038/mt.2012.171.

Cermak, et al. Efficient design and assembly of custom TALEN and other TAL effector-based constructs for DNA targeting. Nucleic Acids Res. Jul. 2011;39(12):e82. doi: 10.1093/nar/gkr218. Epub Apr. 14, 2011.

Charpentier, Abstracts of the Interscience Conference on Antimicrobial Agents and Chemotherapy, 2012, 52, 1785.

Cong et al. Comprehensive interrogation of natural TALE DNA-binding modules and transcriptional repressor domains. Nat Commun. Jul. 24, 2012;3:968. doi: 10.1038/ncomms1962.

Courtin, et al., "Interactions Between Microorganisms in a Simple Ecosystem: Yogurt Bacteria as a Study Model", LAIT, 2004, vol. 84, pp. 125-134.

Cradick, et al. ZFN-site searches genomes for zinc finger nuclease target sites and off-target sites. BMC Bioinformatics. May 13, 2011;12:152. doi: 10.1186/1471-2105-12-152.

Dagnino, et al. Molecular diagnosis of analbuminemia: a new case caused by a nonsense mutation in the albumin gene. Int J Mol Sci. 2011;12(11):7314-22. doi: 10.3390/ijms12117314. Epub Oct. 25, 2011.

Editas Press Release, "Editas Medicine Created to Discover and Develop Novel Class of Genome Editing Therapeutics", Nov. 25, 2013.

Ferretti, et al. Complete genome sequence of an M1 strain of *Streptococcus pyogenes*. Proc Natl Acad Sci U S A. Apr. 10, 2001;98(8):4658-63.

Fu, et al. Improving CRISPR-Cas nuclease specificity using truncated guide RNAs. Nat Biotechnol. Mar. 2014;32(3):279-84. doi: 10.1038/nbt.2808. Epub Jan. 26, 2014.

Gaj, et al. ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.

Garneau, et al. The CRISPR/Cas bacterial immune system cleaves bacteriophage and plasmid DNA. Nature. Nov. 4, 2010;468(7320):67-71. doi: 10.1038/nature09523.

GenBank Accession No. AAL81255, Feb. 25, 2002, "hypothetical protein PF1131 [Pyrococcus furiosus DSM 3638]".

Gentner et al., Identification of hematopoietic stem cell-specific miRNAs enables gene therapy of globoid cell leukodystrophy. Sci Transl Med. Nov. 17, 2010;2(58):58ra84. doi: 10.1126/scitranslmed. 3001522.

Gilbert, et al. CRISPR-mediated modular RNA-guided regulation of transcription in eukaryotes. Cell. Jul. 18, 2013;154(2):442-51. doi: 10.1016/j.cell.2013.06.044. Epub Jul. 11, 2013.

Grabowski. Phenotype, diagnosis, and treatment of Gaucher's disease. Lancet. Oct. 4, 2008;372(9645):1263-71. doi: 10.1016/S0140-6736(08)61522-6.

Gray, et al., Maturase [Neosartorya fischeri] GenBank Accession No. AAX39426, May 19, 2005.

Gritti. Gene therapy for lysosomal storage disorders. Expert Opin Biol Ther. Sep. 2011;11(9):1153-67. doi: 10.1517/14712598.2011. 582036. Epub May 9, 2011.

Gupta, et al. Zinc finger protein-dependent and -independent contributions to the in vivo off-target activity of zinc finger nucleases. Nucleic Acids Res. Jan. 2011;39(1):381-92. doi: 10.1093/nar/gkq787. Epub Sep. 14, 2010.

Hale, et al. Prokaryotic silencing (psi)RNAs in Pyrococcus furiosus. RNA. Dec. 2008;14(12):2572-9. doi: 10.1261/rna.1246808. Epub Oct. 29, 2008.

Hatoum-Aslan, et al. Mature clustered, regularly interspaced, short palindromic repeats RNA (crRNA) length is measured by a ruler mechanism anchored at the precursor processing site. Proc Natl Acad Sci U S A. Dec. 27, 2011;108(52):21218-22. doi: 10.1073/pnas.1112832108. Epub Dec. 12, 2011.

Hockmeyer, et al. Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockmeyer, et al. Genetic engineering of human pluripotent cells using TALE nucleases. Nat Biotechnol. Jul. 7, 2011;29(8):731-4. doi: 10.1038/nbt.1927.

Hofling, et al. Human CD34+hematopoietic progenitor cell-directed lentiviral-mediated gene therapy in a xenotransplantation model of lysosomal storage disease.Mol Ther. Jun. 2004;9(6):856-65.

Hsu, et al. DNA targeting specificity of RNA-guided Cas9 nucleases. Nat Biotechnol. Sep. 2013;31(9):827-32. doi: 10.1038/nbt.2647. Epub Jul. 21, 2013.

Ishino, et al. Nucleotide sequence of the iap gene, responsible for alkaline phosphatase isozyme conversion in *Escherichia coli*, and identification of the gene product. J Bacteriol. Dec. 1987;169(12):5429-33.

Jacoby, et al. Expanding LAGLIDADG endonuclease scaffold diversity by rapidly surveying evolutionary sequence space. Nucleic Acids Res. Jun. 2012;40(11):4954-64. doi: 10.1093/nar/gkr1303. Epub Feb. 14, 2012.

Jacoby, et al., "Chain A, Expanding LAGLIDADG Endonuclease Scaffold Diversity by Rapidly Surveying Evolutionary Sequence Space", GenBank Record Accession No. 3UVF_A, Oct. 10, 2012.

Jacoby, et al., TPA_exp: LAGLIDADG Endonuclease, partial (mitochondrion) [Trichoderma reesei], GenBank Accession No. DAA35182, Jun. 30, 2012.

Kennedy, et al. Rapid blue-light-mediated induction of protein interactions in living cells. Nat Methods. Dec. 2010;7(12):973-5. doi: 10.1038/nmeth.1524. Epub Oct. 31, 2010.

Kim, et al. Long-term expression of the human glucocerebrosidase gene in vivo after transplantation of bone-marrow-derived cells transformed with a lentivirus vector. J Gene Med. Jul. 2005;7(7):878-87.

Leimig, et al. Functional amelioration of murine galactosialidosis by genetically modified bone marrow hematopoietic progenitor cells. Blood. May 1, 2002;99(9):3169-78.

Li, et al. High-efficiency TALEN-based gene editing produces disease-resistant rice. Nat Biotechnol. May 7, 2012;30(5):390-2. doi: 10.1038/nbt.2199.

Luo, et al. Highly parallel identification of essential genes in cancer cells. Proc Natl Acad Sci U S A. Dec. 23, 2008;105(51):20380-5. doi: 10.1073/pnas.0810485105. Epub Dec. 17, 2008.

Ma, et al. A guide RNA sequence design platform for the CRISPR/Cas9 system for model organism genomes. Biomed Res Int. 2013;2013:270805. doi: 10.1155/2013/270805. Epub Oct. 3, 2013.

Malanowska, et al. CTnDOT integrase performs ordered homology-dependent and homology-independent strand exchanges. Nucleic Acids Res. 2007;35(17):5861-73. Epub Aug. 24, 2007.

Marrafini, et al. Self versus non-self discrimination during CRISPR RNA-directed immunity Nature. Jan. 28, 2010;463(7280):568-71. doi: 10.1038/nature08703. Epub. Jan. 13, 2010.

Mittelman, et al. Zinc-finger directed double-strand breaks within CAG repeat tracts promote repeat instability in human cells. Proc Natl Acad Sci U S A. Jun. 16, 2009;106(24):9607-12. doi: 10.1073/pnas.0902420106. Epub May 29, 2009.

Mojica, et al. Intervening sequences of regularly spaced prokaryotic repeats derive from foreign genetic elements. J Mol Evol. Feb. 2005;60(2):174-82.

Mojica, et al. Long stretches of short tandem repeats are present in the largest replicons of the Archaea Haloferax mediterranei and Haloferax volcanii and could be involved in replicon partitioning. Mol Microbiol. Jul. 1995;17(1):85-93.

Mojica, et al. Short motif sequences determine the targets of the prokaryotic CRISPR defence system. Microbiology. Mar. 2009;155(Pt 3):733-40. doi: 10.1099/mic.0.023960-0.

Moore, et al. Improved somatic mutagenesis in zebrafish using transcription activator-like effector nucleases (TALENs). S One. 2012;7(5):e37877. doi: 10.1371/journal.pone.0037877. Epub May 24, 2012.

Moscou, et al. A simple cipher governs DNA recognition by TAL effectors. Science. Dec. 11, 2009;326(5959):1501. doi: 10.1126/science.1178817.

(56) References Cited

OTHER PUBLICATIONS

Muzykantov. Drug delivery by red blood cells: vascular carriers designed by mother nature. Expert Opin Drug Deliv. Apr. 2010;7(4):403-27. doi: 10.1517/17425241003610633.
Notice of allowance dated Feb. 20, 2014 for U.S. Appl. No. 14/054,414.
Office action dated Jan. 17, 2014 for U.S. Appl. No. 14/054,414.
Office action dated Dec. 5, 2013 for U.S. Appl. No. 14/054,414.
Orlando, et al. Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Papapetrou, et al. Genomic safe harbors permit high β-globin transgene expression in thalassemia induced pluripotent stem cells. Nat Biotechnol. Jan. 2011;29(1):73-8. doi: 10.1038/nbt.1717. Epub Dec. 12, 2010.
Pattanayak, et al. Revealing off-target cleavage specificities of zinc-finger nucleases by in vitro selection. Nat Methods. Aug. 7, 2011;8(9):765-70. doi: 10.1038/nmeth.1670.
Pennisi. The CRISPR craze. Science. Aug. 23, 2013;341(6148):833-6. doi: 10.1126/science.341.6148.833.
Povirk, et al., "Role of Brca 1 in Nonhomologous DNA End Joining", U.S. Army Medical Research and Material Command, Award No. DAMD 17-03-01-0620, Sep. 2004, pp. 1-11.
Ramsubir, et al. In vivo delivery of human acid ceramidase via cord blood transplantation and direct injection of lentivirus as novel treatment approaches for Farber disease. Mol Genet Metab. Nov. 2008;95(3):133-41. doi: 10.1016/j.ymgme.2008.08.003. Epub Sep. 20, 2008.
Rho, et al. Diverse CRISPRs evolving in human microbiomes. PLoS Genet. 2012;8(6):e1002441. doi: 10.1371/journal.pgen.1002441. Epub Jun. 13, 2012.
Sampson, et al. A CRISPR/Cas system mediates bacterial innate immune evasion and virulence. Nature. May 9, 2013;497(7448):254-7. doi: 10.1038/nature12048. Epub Apr. 14, 2013.
Sanjana, et al. A transcription activator-like effector toolbox for genome engineering. Nat Protoc. Jan. 5, ;7(1):171-92. doi: 10.1038/nprot.2011.431.
Shalem, et al. Genome-scale CRISPR-Cas9 knockout screening in human cells. Science. Jan. 3, 2014;343(6166):84-7. doi: 10.1126/science.1247005. Epub Dec. 12, 2013.
Sims, et al. High-throughput RNA interference screening using pooled shRNA libraries and next generation sequencing. Genome Biol. Oct. 21, 2011;12(10):R104. doi: 10.1186/gb-2011-12-10-r104.
Sontheimer et al., "Project 7: Establishing RNA-Directed DNA Targeting in Eukaryotic Cells; Project dates: Nov. 16, 2011 to Dec. 31, 2012" (Feb. 4, 2012).
Sorek et al. CRISPR-mediated adaptive immune systems in bacteria and archaea. Annu Rev Biochem. 2013;82:237-66. doi: 10.1146/annurev-biochem-072911-172315. Epub Mar. 11, 2013.
Stern, et al. Self-targeting by CRISPR: gene regulation or autoimmunity? Trends Genet. Aug. 2010;26(8):335-40. doi: 10.1016/j.tig.2010.05.008. Epub Jul. 1, 2010.
Sun, et al. Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Tan, et al. Precision editing of large animal genomes. Adv Genet. 2012;80:37-97. doi: 10.1016/B978-0-12-404742-6.00002-8.
Terns, et al. The CRISPR-Cas system: small RNA-guided invader small RNA-guided invader silencing in prokaryotes. The FASEB J. 2012, vol. 26, Abstract 353.3.
Urnov, et al. Highly efficient endogenous human gene correction using designed zinc-finger nucleases. Nature. Jun. 2, 2005;435(7042):646-51. Epub Apr. 3, 2005.
Van Til, et al. Lentiviral gene therapy of murine hematopoietic stem cells ameliorates the Pompe disease phenotype. Blood. Jul. 1, 2010;115(26):5329-37. doi: 10.1182/blood-2009-11-252874. Epub Apr. 12, 2010.
Wang, et al. Genetic correction of β-thalassemia patient-specific iPS cells and its use in improving hemoglobin production in irradiated SCID mice. Cell Res. Apr. 2012;22(4):637-48. doi: 10.1038/cr.2012.23. Epub Feb. 7, 2012.
Wang, et al. Reprogramming erythroid cells for lysosomal enzyme production leads to visceral and CNS cross-correction in mice with Hurler syndrome. Proc Natl Acad Sci U S A. Nov. 24, 2009;106(47):19958-63. doi: 10.1073/pnas.0908528106. Epub Nov. 10, 2009.
Wang, et al. Spatiotemporal control of gene expression by a light-switchable transgene system. Nat Methods. Feb. 12, 2012;9(3):266-9. doi: 10.1038/nmeth.1892.
Zhang, et al. cSSMD: assessing collective activity for addressing off-target effects in genome-scale RNA interference screens. Bioinformatics. Oct. 15, 2011;27(20):2775-81. doi: 10.1093/bioinformatics/btr474. Epub Aug. 16, 2011.
Zhou, et al. Mouse model for the lysosomal disorder galactosialidosis and correction of the phenotype with overexpressing erythroid precursor cells. Genes Dev. Nov. 1, 1995;9(21):2623-34.
Deveau; et al., "Phage response to CRISPR-encoded resistance in *Streptococcus thermophilus*. J. Bacteriol. (Feb. 2008), 190(4):1390-400.".
Mastroianni; et al., "Group II intron-based gene targeting reactions in eukaryotes. PLoS One. (Sep. 2008), 3 (9):e3121.".
Raymond; et al., "High-efficiency FLP and PhiC31 site-specific recombination in mammalian cells. PLoS One. (Jan. 2007), 2(1): e162.".

* cited by examiner

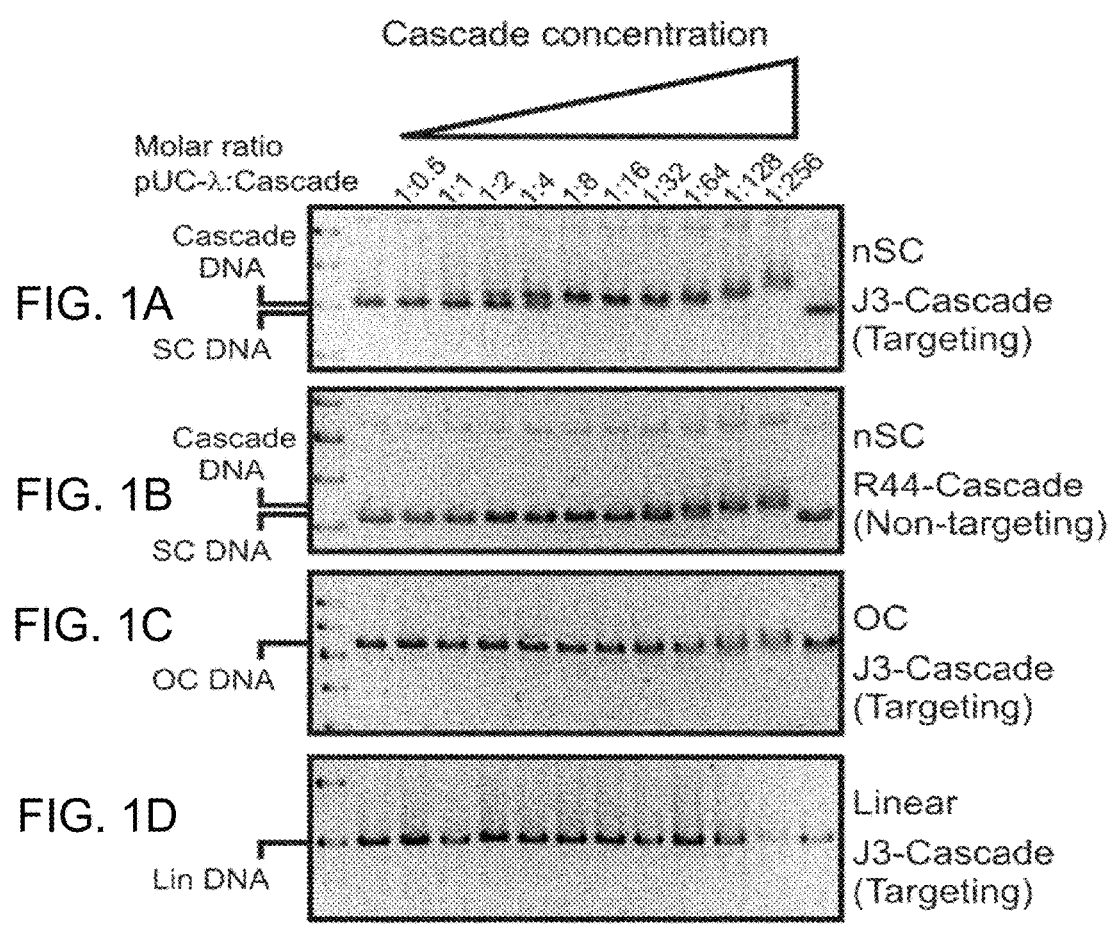

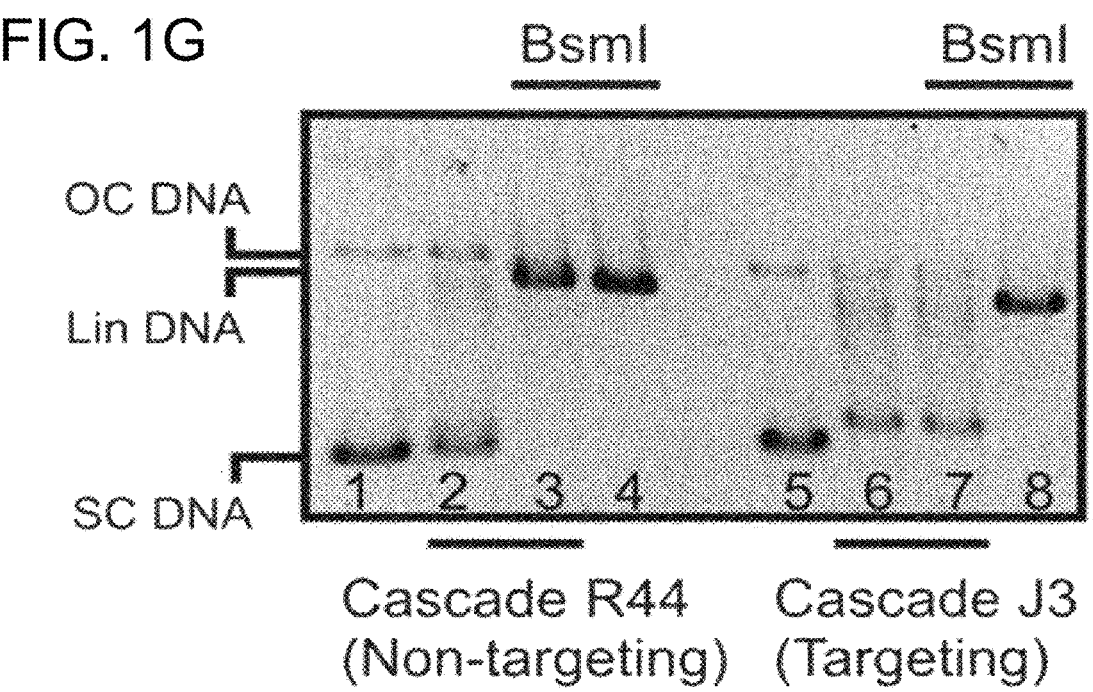

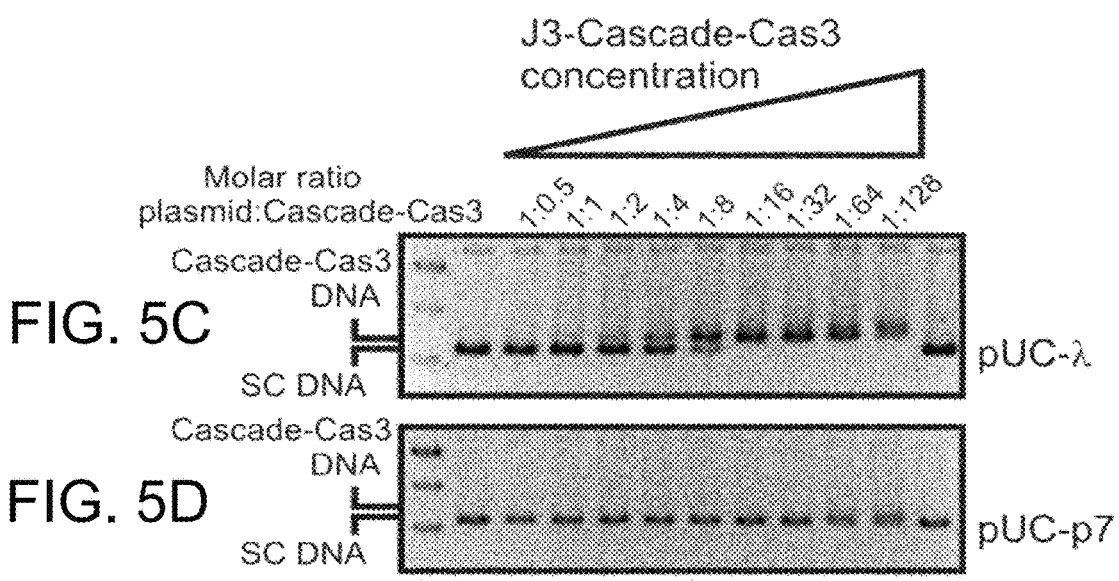

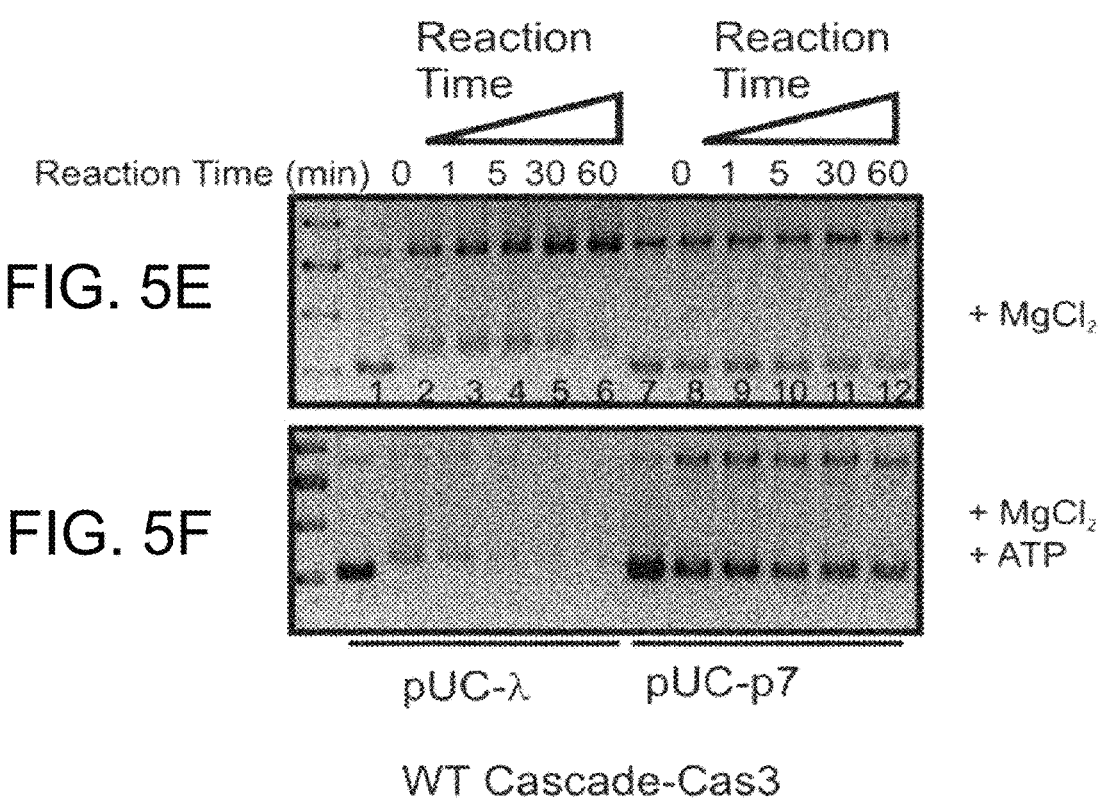

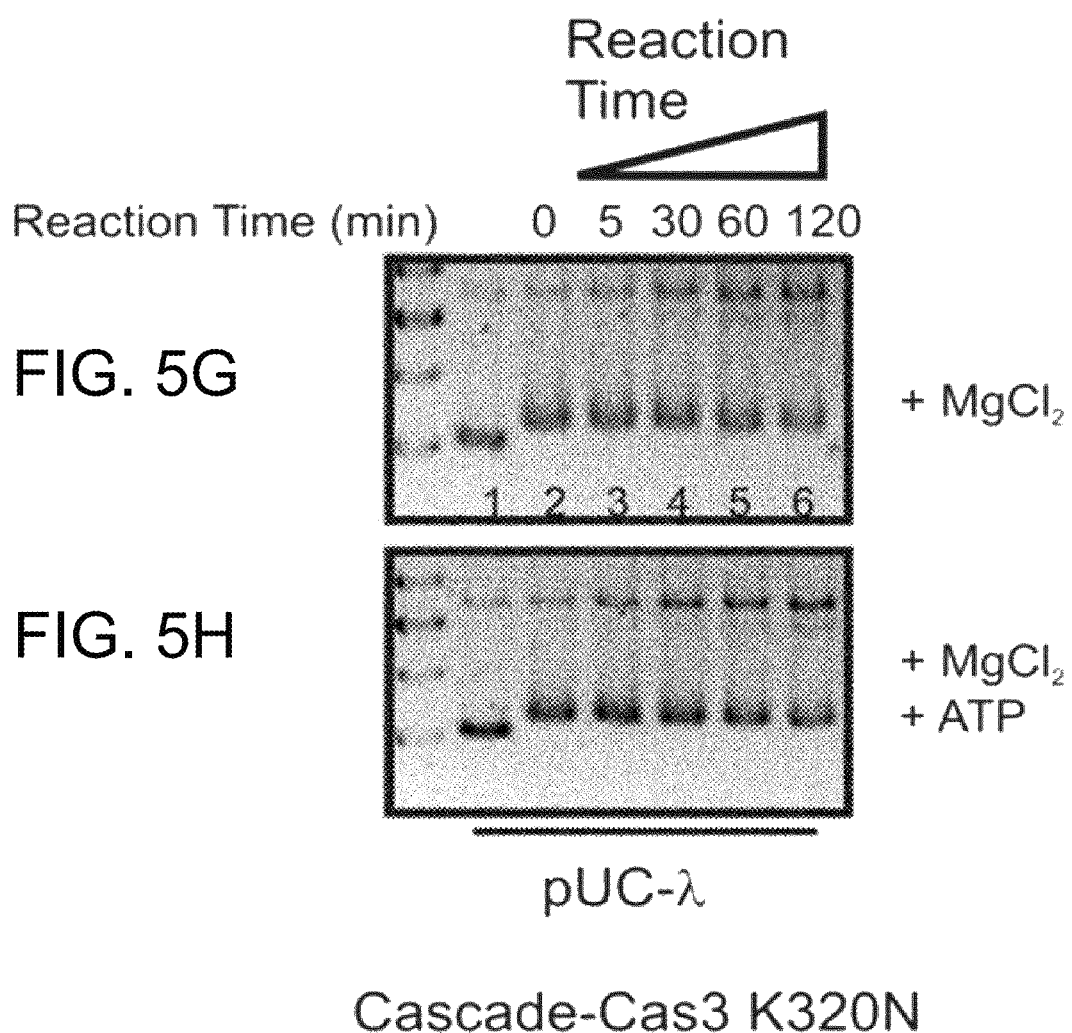

1: Protospacer scanning

2: Protospacer binding

3: Cas3-Cascade complex formation

4: Nicking by Cas3 HD-domain

5a: Cas3 ATP-dependent exo-nuclease activity

5b: Cascade dissociation

6: Full plasmid degradation by Cas3

FIG. 9

```
                PAM    Seed
wildtype   AAGGATGCCAGTGATAAGTGGAATGCCATGTGGGCTGTCAAAA mutant 1   AAGGATGCGAGTGATAAGTGGAATGCCATGTGGGCTGTCAAAA
mutant 2   ------------------------------------GCCATGTGGGCTGTCAAAA
mutant 3   --------------------------------GAATGCCATGTGGGCTGTCAAAA
mutant 4   -------------------------------------------------------
```

MODIFIED CASCADE RIBONUCLEOPROTEINS AND USES THEREOF

This application is a continuation of U.S. patent application Ser. No. 14/997,474, filed 15 Jan. 2016, now pending, which is a continuation of U.S. patent application Ser. No. 14/326,099, filed 8 Jul. 2014, now abandoned, which is a continuation of U.S. patent application Ser. No. 14/240,735, filed 24 Feb. 2014, now abandoned, which is a National Stage Entry of PCT/EP2012/076674, filed 21 Dec. 2012, now expired, which claims the benefit of priority under 35 U.S.C. 119(a)/(b) of United Kingdom Patent Application No. GB 1122458.1, filed 30 Dec. 2011, now expired, the contents of all of which are herein incorporated by reference in their entireties. A certified copy of the foreign priority document (GB 1122458.1) is of record in U.S. patent application Ser. No. 14/240,735.

The present application contains a Sequence Listing that has been submitted electronically in ASCII format and is hereby incorporated by reference in its entirety. The ASCII copy, created on Jan. 9, 2018, is named CBI010-14_ST25.txt and is 119 KB in size.

The invention relates to the field of genetic engineering and more particularly to the area of gene and/or genome modification of organisms, including prokaryotes and eukaryotes. The invention also concerns methods of making site specific tools for use in methods of genome analysis and genetic modification, whether in vivo or in vitro. The invention more particularly relates to the field of ribonucleoproteins which recognise and associate with nucleic acid sequences in a sequence specific way.

Bacteria and archaea have a wide variety of defense mechanisms against invasive DNA. So called CRISPR/Cas defense systems provide adaptive immunity by integrating plasmid and viral DNA fragments in loci of clustered regularly interspaced short palindromic repeats (CRISPR) on the host chromosome. The viral or plasmid-derived sequences, known as spacers, are separated from each other by repeating host-derived sequences. These repetitive elements are the genetic memory of this immune system and each CRISPR locus contains a diverse repertoire of unique 'spacer' sequences acquired during previous encounters with foreign genetic elements.

Acquisition of foreign DNA is the first step of immunization, but protection requires that the CRISPR is transcribed and that these long transcripts are processed into short CRISPR-derived RNAs (crRNAs) that each contains a unique spacer sequence complementary to a foreign nucleic acid challenger.

In addition to the crRNA, genetic experiments in several organisms have revealed that a unique set of CRISPR-associated (Cas) proteins is required for the steps of acquiring immunity, for crRNA biogenesis and for targeted interference. Also, a subset of Cas proteins from phylogenetically distinct CRISPR systems have been shown to assemble into large complexes that include a crRNA.

A recent re-evaluation of the diversity of CRISPR/Cas systems has resulted in a classification into three distinct types (Makarova K. et al (2011) Nature Reviews Microbiology—AOP 9 May 2011; doi:10.1038/nrmicro2577) that vary in cas gene content, and display major differences throughout the CRISPR defense pathway. (The Makarova classification and nomenclature for CRISPR-associated genes is adopted in the present specification.) RNA transcripts of CRISPR loci (pre-crRNA) are cleaved specifically in the repeat sequences by CRISPR associated (Cas) endoribonucleases in type I and type III systems or by RNase III in type II systems; the generated crRNAs are utilized by a Cas protein complex as a guide RNA to detect complementary sequences of either invading DNA or RNA. Cleavage of target nucleic acids has been demonstrated in vitro for the *Pyrococcus furiosus* type III-B system, which cleaves RNA in a ruler-anchored mechanism, and, more recently, in vivo for the *Streptococcus thermophiles* type II system, which cleaves DNA in the complementary target sequence (protospacer). In contrast, for type I systems the mechanism of CRISPR-interference is still largely unknown.

The model organism *Escherichia coli* strain K12 possesses a CRISPR/Cas type I-E (previously known as CRISPR subtype E (Cse)). It contains eight cas genes (cas1, cas2, cas3 and cse1, cse2, cas7, cas5, cas6e) and a downstream CRISPR (type-2 repeats). In *Escherichia coli* K12 the eight cas genes are encoded upstream of the CRISPR locus. Cas1 and Cas2 do not appear to be needed for target interference, but are likely to participate in new target sequence acquisition. In contrast, six Cas proteins: Cse1, Cse2, Cas3, Cas7, Cas5 and Cas6e (previously also known as CasA, CasB, Cas3, CasC/Cse4, CasD and CasE/Cse3 respectively) are essential for protection against lambda phage challenge. Five of these proteins: Cse1, Cse2, Cas7, Cas5 and Cas6e (previously known as CasA, CasB, CasC/Cse4, CasD and CasE/Cse3 respectively) assemble with a crRNA to form a multi-subunit ribonucleoprotein (RNP) referred to as Cascade.

In *E. coli*, Cascade is a 405 kDa ribonucleoprotein complex composed of an unequal stoichiometry of five functionally essential Cas proteins: $Cse1_1Cse2_2Cas7_6Cas5_1Cas6e_1$ (i.e. under previous nomenclature $CasA_1B_2C_6D_1E_1$) and a 61-nt CRISPR-derived RNA. Cascade is an obligate RNP that relies on the crRNA for complex assembly and stability, and for the identification of invading nucleic acid sequences. Cascade is a surveillance complex that finds and binds foreign nucleic acids that are complementary to the spacer sequence of the crRNA.

Jore et al. (2011) entitled "Structural basis for CRISPR RNA-guided DNA recognition by Cascade" Nature Structural & Molecular Biology 18: 529-537 describes how there is a cleavage of the pre-crRNA transcript by the Cas6e subunit of Cascade, resulting in the mature 61 nt crRNA being retained by the CRISPR complex. The crRNA serves as a guide RNA for sequence specific binding of Cascade to double stranded (ds) DNA molecules through base pairing between the crRNA spacer and the complementary protospacer, forming a so-called R-loop. This is known to be an ATP-independent process.

Brouns S. J. J., et al (2008) entitled "Small CRISPR RNAs guide antiviral defense in prokaryotes" Science 321: 960-964 teaches that Cascade loaded with a crRNA requires Cas3 for in vivo phage resistance.

Marraffini L. & Sontheimer E. (2010) entitled "CRISPR interference: RNA-directed adaptive immunity in bacteria and archaea" Nature Reviews Genetics 11: 181-190 is a review article which summarises the state of knowledge in the art in the field. Some suggestions are made about CRISPR-based applications and technologies, but this is mainly in the area of generating phage resistant strains of domesticated bacteria for the dairy industry. The specific cleavage of RNA molecules in vitro by a crRNP complex in *Pyrococcus furiosus* is suggested as something which awaits further development. Manipulation of CRISPR systems is also suggested as a possible way of reducing transmission of antibiotic-resistant bacterial strains in hospitals. The authors stress that further research effort will be needed to explore the potential utility of the technology in these areas.

US2011236530 A1 (Manoury et al.) entitled "Genetic cluster of strains of *Streptococcus thermophilus* having unique rheological properties for dairy fermentation" discloses certain *S. thermophilus* strains which ferment milk so that it is highly viscous and weakly ropy. A specific CRISPR locus of defined sequence is disclosed.

US2011217739 A1 (Terns et al.) entitled "Cas6 polypeptides and methods of use" discloses polypeptides which have Cas6 endoribonuclease activity. The polypeptides cleave a target RNA polynucleotide having a Cas6 recognition domain and cleavage site. Cleavage may be carried out in vitro or in vivo. Microbes such as *E. coli* or *Haloferax volcanii* are genetically modified so as to express Cas6 endoribonuclease activity.

WO2010054154 (Danisco) entitled "Bifidobacteria CRISPR sequences" discloses various CRISPR sequences found in Bifidobacteria and their use in making genetically altered strains of the bacteria which are altered in their phage resistance characteristics.

US2011189776 A1 (Terns et al.) entitled "Prokaryotic RNAi-like system and methods of use" describes methods of inactivating target polynucleotides in vitro or in prokaryotic microbes in vivo. The methods use a psiRNA having a 5' region of 5-10 nucleotides chosen from a repeat from a CRISPR locus immediately upstream of a spacer. The 3' region is substantially complementary to a portion of the target polynucleotide. Also described are polypeptides having endonuclease activity in the presence of psiRNA and target polynucleotide.

EP2341149 A1 (Danisco) entitled "Use of CRISPR associated genes (CAS) describes how one or more Cas genes can be used for modulating resistance of bacterial cells against bacteriophage; particularly bacteria which provide a starter culture or probiotic culture in dairy products.

WO2010075424 (The Regents of the University of California) entitled "Compositions and methods for downregulating prokaryotic genes" discloses an isolated polynucleotide comprising a CRISPR array. At least one spacer of the CRISPR is complementary to a gene of a prokaryote so that is can down-regulate expression of the gene; particularly where the gene is associated with biofuel production.

WO2008108989 (Danisco) entitled "Cultures with improved phage resistance" discloses selecting bacteriophage resistant strains of bacteria and also selecting the strains which have an additional spacer having 100% identity with a region of phage RNA. Improved strain combinations and starter culture rotations are described for use in the dairy industry. Certain phages are described for use as biocontrol agents.

WO2009115861 (Institut Pasteur) entitled "Molecular typing and subtyping of *Salmonella* by identification of the variable nucleotide sequences of the CRISPR loci" discloses methods for detecting and identifying bacterial of the *Salmonella* genus by using their variable nucleotide sequences contained in CRISPR loci.

WO2006073445 (Danisco) entitled "Detection and typing of bacterial strains" describes detecting and typing of bacterial strains in food products, dietary supplements and environmental samples. Strains of *Lactobacillus* are identified through specific CRISPR nucleotide sequences.

Urnov F et al. (2010) entitled "Genome editing with engineered zinc finger nucleases" Nature 11: 636-646 is a review article about zinc finger nucleases and how they have been instrumental in the field of reverse genetics in a range of model organisms. Zinc finger nucleases have been developed so that precisely targeting genome cleavage is possible followed by gene modification in the subsequent repair process. However, zinc finger nucleases are generated by fusing a number of zinc finger DNA-binding domains to a DNA cleavage domain. DNA sequence specificity is achieved by coupling several zinc fingers in series, each recognising a three nucleotide motif. A significant drawback with the technology is that new zinc fingers need to be developed for each new DNA locus which requires to be cleaved. This requires protein engineering and extensive screening to ensure specificity of DNA binding.

In the fields of genetic engineering and genomic research there is an ongoing need for improved agents for sequence/site specific nucleic acid detection and/or cleavage.

The inventors have made a surprising discovery in that certain bacteria expressing Cas3, which has helicase-nuclease activity, express Cas3 as a fusion with Cse1. The inventors have also unexpectedly been able to produce artificial fusions of Cse1 with other nuclease enzymes.

The inventors have also discovered that Cas3-independent target DNA recognition by Cascade marks DNA for cleavage by Cas3, and that Cascade DNA binding is governed by topological requirements of the target DNA.

The inventors have further found that Cascade is unable to bind relaxed target plasmids, but surprisingly Cascade displays high affinity for targets which have a negatively supercoiled (nSC) topology.

Accordingly in a first aspect the present invention provides a clustered regularly interspaced short palindromic repeat (CRISPR)-associated complex for antiviral defence (Cascade), the Cascade protein complex, or portion thereof, comprising at least CRISPR-associated protein subunits:

Cas7 (or COG 1857) having an amino acid sequence of SEQ ID NO:3 or a sequence of at least 18% identity therewith, Cas5 (or COG1688) having an amino acid sequence of SEQ ID NO:4 or a sequence of at least 17% identity therewith, and Cas6 (or COG 1583) having an amino acid sequence of SEQ ID NO:5 or a sequence of at least 16% identity therewith;

and wherein at least one of the subunits includes an additional amino acid sequence providing nucleic acid or chromatin modifying, visualising, transcription activating or transcription repressing activity.

A subunit which includes an additional amino acid sequence having nucleic acid or chromatin modifying, visualising, transcription activating or transcription repressing activity is an example of what may be termed "a subunit linked to at least one functional moiety"; a functional moiety being the polypeptide or protein made up of the additional amino acid sequence. The transcription activating activity may be that leading to activation or upregulation of a desired genes; the transcription repressing activity leading to repressing or downregulation of a desired genes. The selection of the gene being due to the targeting of the cascade complex of the invention with an RNA molecule, as described further below.

The additional amino acid sequence having nucleic acid or chromatin modifying, visualising, transcription activating or transcription repressing activity is preferably formed of contiguous amino acid residues. These additional amino acids may be viewed as a polypeptide or protein which is contiguous and forms part of the Cas or Cse subunit(s) concerned. Such a polypeptide or protein sequence is preferably not normally part of any Cas or Cse subunit amino acid sequence. In other words, the additional amino acid sequence having nucleic acid or chromatin modifying, visualising, transcription activating or transcription repressing activity may be other than a Cas or Cse subunit amino acid sequence, or portion thereof, i.e. may be other than a Cas3 submit amino acid sequence or portion thereof.

The additional amino acid sequence with nucleic acid or chromatin modifying, visualising, transcription activating or transcription repressing activity may, as desired, be obtained or derived from the same organism, e.g. E. coli, as the Cas or Cse subunit(s).

Additionally and/or alternatively to the above, the additional amino acid sequence having nucleic acid or chromatin modifying, visualising, transcription activating or transcription repressing activity may be "heterologous" to the amino acid sequence of the Cas or Cse subunit(s). Therefore, the additional amino acid sequence may be obtained or derived from an organism different from the organism from which the Cas and/or Cse subunit(s) are derived or originate.

Throughout, sequence identity may be determined by way of BLAST and subsequent Cobalt multiple sequence alignment at the National Center for Biotechnology Information webserver, where the sequence in question is compared to a reference sequence (e.g. SEQ ID NO: 3, 4 or 5). The amino acid sequences may be defined in terms of percentage sequence similarity based on a BLOSUM62 matrix or percentage identity with a given reference sequence (e.g. SEQ ID NO:3, 4 or 5). The similarity or identity of a sequence involves an initial step of making the best alignment before calculating the percentage conservation with the reference and reflects a measure of evolutionary relationship of sequences.

Cas7 may have a sequence similarity of at least 31% with SEQ ID NO:3; Cas5 may have a sequence similarity of at least 26% with SEQ ID NO:4. Cas6 may have a sequence similarity of at least 27% with SEQ ID NO:5.

```
For Cse1/CasA (502 AA):
>gi|16130667|ref|NP_417240.1| CRISP RNA (crRNA)
containing Cascade antiviral complex protein
[Escherichia coli str. K-12 substr. MG1655]
                                      [SEQ ID NO: 1]
MNLLIDNWIPVRPRNGGKVQIINLQSLYCSRDQWRLSLPRDDMELAALAL

LVCIGQIIAPAKDDVEFRHRIMNPLTEDEFQQLIAPWIDMFYLNHAEHPF

MQTKGVKANDVTPMEKLLAGVSGATNCAFVNQPGQGEALCGGCTAIALFN

QANQAPGFGGGFKSGLRGGTPVTTFVRGIDLRSTVLLNVLTLPRLQKQFP

NESHTENQPTWIKPIKSNESIPASSIGFVRGLFWQPAHIELCDPIGIGKC

SCCGQESNLRYTGFLKEKFTFTVNGLWPHPHSPCLVTVKKGEVEEKFLAF

TTSAPSWTQISRVVVDKIIQNENGNRVAAVVNQFRNIAPQSPLELIMGGY

RNNQASILERRHDVLMFNQGWQQYGNVINEIVTVGLGYKTALRKALYTFA

EGFKNKDFKGAGVSVHETAERHFYRQSELLIPDVLANVNFSQADEVIADL

RDKLHQLCEMLFNQSVAPYAHHPKLISTLALARATLYKHLRELKPQGGPS

NG

For Cse2/CasB (160 AA):
>gi|16130666|ref|NP_417239.1| CRISP RNA (crRNA)
containing Cascade antiviral complex protein
[Escherichia coli str. K-12 substr. MG1655]
                                      [SEQ ID NO: 2]
MADEIDAMALYRAWQQLDNGSCAQIRRVSEPDELRDIPAFYRLVQPFGWE

NPRHQQALLRMVFCLSAGKNVIRHQDKKSEQTTGISLGRALANSGRINER
```

```
-continued
RIFQLIRADRTADMVQLRRLLTHAEPVLDWPLMARMLTWWGKRERQQLLE

DFVLTTNKNA

For Cas7/CasC/Cse4 (363 AA):
>gi|16130665|ref|NP_417238.1| CRISP RNA (crRNA)
containing Cascade antiviral complex protein
[Escherichia coli str. K-12 substr. MG1655]
                                      [SEQ ID NO: 3]
MSNFINIHVLISHSPSCLNRDDMNMQKDAIFGGKRRVRISSQSLKRAMRK

SGYYAQNIGESSLRTIHLAQLRDVLRQKLGERFDQKIIDKTLALLSGKSV

DEAEKISADAVTPWVVGEIAWFCEQVAKAEADNLDDKKLLKVLKEDIAAI

RVNLQQGVDIALSGRMATSGMMTELGKVDGAMSIAHAITTHQVDSDIDWF

TAVDDLQEQGSAHLGTQEFSSGVFYRYANINLAQLQENLGGASREQALEI

ATHVVHMLATEVPGAKQRTYAAFNPADMVMVNFSDMPLSMANAFEKAVKA

KDGFLQPSIQAFNQYWDRVANGYGLNGAAAQFSLSDVDPITAQVKQMPTL

EQLKSWVRNNGEA

For Cas5/CasD (224 AA):
>gi|90111483|ref|NP_417237.2| CRISP RNA (crRNA)
containing Cascade antiviral complex protein
[Escherichia coli str. K-12 substr. MG1655]
                                      [SEQ ID NO: 4]
MRSYLILRLAGPMQAWGQPTFEGTRPTGRFPTRSGLLGLLGACLGIQRDD

TSSLQALSESVQFAVRCDELILDDRRVSVTGLRDYHTVLGAREDYRGLKS

HETIQTWREYLCDASFTVALWLTPHATMVISELEKAVLKPRYTPYLGRRS

CPLTHPLFLGTCQASDPQKALLNYEPVGGDIYSEESVTGHHLKFTARDEP

MITLPRQFASREWYVIKGGMDVSQ

For Cas6e/CasE (199 AA):
>gi|16130663|ref|NP_417236.1| CRISPR RNA precursor
cleavage enzyme; CRISP RNA (crRNA) containing
Cascade antiviral complex protein [Escherichia
coli str. K-12 substr. MG1655]
                                      [SEQ ID NO: 5]
MYLSKVIIARAWSRDLYQLHQGLWHLFPNRPDAARDFLFHVEKRNTPEGC

HVLLQSAQMPVSTAVATVIKTKQVEFQLQVGVPLYFRLRANPIKTILDNQ

KRLDSKGNIKRCRVPLIKEAEQIAWLQRKLGNAARVEDVHPISERPQYFS

GDGKSGKIQTVCFEGVLTINDAPALIDLVQQGIGPAKSMGCGLLSLAPL
```

In defining the range of sequence variants which fall within the scope of the invention, for the avoidance of doubt, the following are each optional limits on the extent of variation, to be applied for each of SEQ ID NO:1, 2, 3, 4 or 5 starting from the respect broadest range of variants as specified in terms of the respective percentage identity above. The range of variants therefore may therefore include: at least 16%, or at least 17%, or at least 18%, or at least 19%, or at least 20%, or at least 21%, or at least 22%, or at least 23%, or at least 24%, or at least 25%, or at least 26%, or at least 27%, or at least 28%, or at least 29%, or at least 30%, or at least 31%, or at least 32%, or at least 33%, or at least 34%, or at least 35%, or at least 36%, or at least 37%, or at least 38%, or at least 39%, or at least 40%, or at least 41%, or at least 42%, or at least 43%, at least 44%, or at least 45%, or at least 46%, or at least 47%, or at least 48%, or at least 49%, or at least 50%, or at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or at least 65%, or at least 66%, or at least 67%, or at least 68%, or at least 69%, or at least 70%, or at least 71%, at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% amino acid sequence identity.

Throughout, the Makarova et al. (2011) nomenclature is being used in the definition of the Cas protein subunits. Table 2 on page 5 of the Makarova et al. article lists the Cas genes and the names of the families and superfamilies to which they belong. Throughout, reference to a Cas protein or Cse protein subunit includes cross reference to the family or superfamily of which these subunits form part.

Throughout, the reference sequences of the Cas and Cse subunits of the invention may be defined as a nucleotide sequence encoding the amino acid sequence. For example, the amino acid sequence of SEQ ID NO:3 for Cas7 also includes all nucleic acid sequences which encode that amino acid sequence. The variants of Cas7 included within the scope of the invention therefore include nucleotide sequences of at least the defined amino acid percentage identities or similarities with the reference nucleic acid sequence; as well as all possible percentage identities or similarities between that lower limit and 100%.

The Cascade complexes of the invention may be made up of subunits derived or modified from more than one different bacterial or archaeal prokaryote. Also, the subunits from different Cas subtypes may be mixed.

In a preferred aspect, the Cas6 subunit is a Cas6e subunit of SEQ ID NO: 17 below, or a sequence of at least 16% identity therewith.

The sequence of a preferred Cas6e subunit is >gi|16130663|ref|NP_417236.1| CRISPR RNA precursor cleavage enzyme; CRISP RNA (crRNA) containing Cascade antiviral complex protein [*Escherichia coli* str. K-12 substr. MG1655]:

[SEQ ID NO: 17]
MYLSKVIIARAWSRDLYQLHQGLWHLFPNRPDAARDFLFHVEKRNTPEGC

HVLLQSAQMPVSTAVATVIKTKQVEFQLQVGVPLYFRLRANPIKTILDNQ

KRLDSKGNIKRCRVPLIKEAEQIAWLQRKLGNAARVEDVHPISERPQYFS

GDGKSGKIQTVCFEGVLTINDAPALIDLVQQGIGPAKSMGCGLLSLAPL

The Cascade complexes, or portions thereof, of the invention—which comprise at least one subunit which includes an additional amino acid sequence having nucleic acid or chromatin modifying, visualising, transcription activating or transcription repressing activity—may further comprise a Cse2 (or YgcK-like) subunit having an amino acid sequence of SEQ ID NO:2 or a sequence of at least 20% identity therewith, or a portion thereof. Alternatively, the Cse subunit is defined as having at least 38% similarity with SEQ ID NO:2. Optionally, within the protein complex of the invention it is the Cse2 subunit which includes the additional amino acid sequence having nucleic acid or chromatin modifying activity.

Additionally or alternatively, the Cascade complexes of the invention may further comprise a Cse1 (or YgcL-like) subunit having an amino acid sequence of SEQ ID NO: 1 or a sequence of at least 9% identity therewith, or a portion thereof. Optionally within the protein complex of the invention it is the Cse1 subunit which includes the additional amino acid sequence having nucleic acid or chromatin modifying, visualising, transcription activating or transcription repressing activity.

In preferred embodiments, a Cascade complex of the invention is a Type I CRISPR-Cas system protein complex; more preferably a subtype I-E CRISPR-Cas protein complex or it can be based on a Type I-A or Type I-B complex. A Type I-C, D or F complex is possible. In particularly preferred embodiments based on the *E. coli* system, the subunits may have the following stoichiometries: $Cse1_1Cse2_2Cas7_6Cas5_1Cas6_1$ or $Cse1_1Cse2_2Cas7_6Cas5_1Cas6e_1$.

The additional amino acid sequence having nucleic acid or chromatin modifying, visualising, transcription activating or transcription repressing activity may be translationally fused through expression in natural or artificial protein expression systems, or covalently linked by a chemical synthesis step to the at least one subunit; preferably the at least one functional moiety is fused or linked to at least the region of the N terminus and/or the region of the C terminus of at least one of a Cse1, Cse2, Cas7, Cas5, Cas6 or Cas6e subunit. In particularly preferred embodiments, the additional amino acid sequence having nucleic acid or chromatin modifying activity is fused or linked to the N terminus or the C terminus of a Cse1, a Cse2 or a Cas5 subunit; more preferably the linkage is in the region of the N terminus of a Cse1 subunit, the N terminus of a Cse2 subunit, or the N terminus of a Cas7 subunit.

The additional amino acid sequence having nucleic acid or chromatin modifying, activating, repressing or visualising activity may be a protein; optionally selected from a helicase, a nuclease, a nuclease-helicase, a DNA methyltransferase (e.g. Dam), or DNA demethylase, a histone methyltransferase, a histone demethylase, an acetylase, a deacetylase, a phosphatase, a kinase, a transcription (co-) activator, an RNA polymerase submit, a transcription repressor, a DNA binding protein, a DNA structuring protein, a marker protein, a reporter protein, a fluorescent protein, a ligand binding protein (e.g. mCherry or a heavy metal binding protein), a signal peptide (e.g. Tat-signal sequence), a subcellular localisation sequence (e.g. nuclear localisation sequence) or an antibody epitope.

The protein concerned may be a heterologous protein from a species other than the bacterial species from which the Cascade protein subunits have their sequence origin.

When the protein is a nuclease, it may be one selected from a type II restriction endonuclease such as FokI, or a mutant or an active portion thereof. Other type II restriction endonucleases which may be used include EcoR1, EcoRV, BglII, BamHI, BsgI and BspMI. Preferably, one protein complex of the invention may be fused to the N terminal domain of FokI and another protein complex of the invention may be fused to the C terminal domain of FokI. These two protein complexes may then be used together to achieve an advantageous locus specific double stranded cut in a nucleic acid, whereby the location of the cut in the genetic material is at the design and choice of the user, as guided by the RNA component (defined and described below) and due to presence of a so-called "protospacer adjacent motif" (PAM) sequence in the target nucleic acid strand (also described in more detail below).

In a preferred embodiment, a protein complex of the invention has an additional amino acid sequence which is a modified restriction endonuclease, e.g. FokI. The modification is preferably in the catalytic domain. In preferred embodiments, the modified FokI is KKR Sharkey or ELD Sharkey which is fused to the Cse1 protein of the protein complex. In a preferred application of these complexes of the invention, two of these complexes (KKR Sharkey and ELD Sharkey) may be together in combination. A heterodimer pair of protein complexes employing differently modified FokI is has particular advantage in targeted double stranded cutting of nucleic acid. If homodimers are used then it is possible that there is more cleavage at non-target sites due to non-specific activity. A heterodimer approach advantageously increases the fidelity of the cleavage in a sample of material.

The Cascade complex with additional amino acid sequence having nucleic acid or chromatin modifying, visualising, transcription activating or transcription repressing activity defined and described above is a component part of an overall system of the invention which advantageously permits the user to select in a predetermined matter a precise genetic locus which is desired to be cleaved, tagged or otherwise altered in some way, e.g methylation, using any of the nucleic acid or chromatin modifying, visualising, transcription activating or transcription repressing entities defined herein. The other component part of the system is an RNA molecule which acts as a guide for directing the Cascade complex of the invention to the correct locus on DNA or RNA intending to be modified, cut or tagged.

The Cascade complex of the invention preferably also comprises an RNA molecule which comprises a ribonucleotide sequence of at least 50% identity to a desired target nucleic acid sequence, and wherein the protein complex and the RNA molecule form a ribonucleoprotein complex. Preferably the ribonucleoprotein complex forms when the RNA molecule is hybridized to its intended target nucleic acid sequence. The ribonucleoprotein complex forms when the necessary components of Cascade-functional moiety combination and RNA molecule and nucleic acid (DNA or RNA) are present together in suitable physiological conditions, whether in vivo or in vitro. Without wishing to be bound by any particular theory, the inventors believe that in the context of dsDNA, particularly negatively supercoiled DNA, the Cascade complex associating with the dsDNA causes a partial unwinding of the duplex strands which then allows the RNA to associate with one strand; the whole ribonucleoprotein complex then migrates along the DNA strand until a target sequence substantially complementary to at least a portion of the RNA sequence is reached, at which point a stable interaction between RNA and DNA strand occurs, and the function of the functional moiety takes effect, whether by modifying, nuclease cutting or tagging of the DNA at that locus.

In preferred embodiments, a portion of the RNA molecule has at least 50% identity to the target nucleic acid sequence; more preferably at least 95% identity to the target sequence. In more preferred embodiments, the portion of the RNA molecule is substantially complementary along its length to the target DNA sequence; i.e. there is only one, two, three, four or five mismatches which may be contiguous or non-contiguous. The RNA molecule (or portion thereof) may have at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% identity to the target sequence.

The target nucleic acid may be DNA (ss or ds) or RNA.

In other preferred embodiments, the RNA molecule or portion thereof has at least 70% identity with the target nucleic acid. At such levels of identity, the target nucleic acid is preferably dsDNA.

The RNA molecule will preferably require a high specificity and affinity for the target nucleic acid sequence. A dissociation constant ($K_d$) in the range 1 pM to 1 µM, preferably 1-100 nM is desirable as determined by preferably native gel electrophoresis, or alternatively isothermal titration calorimetry, surface plasmon resonance, or fluorescence based titration methods. Affinity may be determined using an electrophoretic mobility shift assay (EMSA), also called gel retardation assay (see Semenova E et al. (2011) Proc. Natl. Acad. Sci. USA 108: 10098-10103).

The RNA molecule is preferably modelled on what are known from nature in prokaryotes as CRISPR RNA (crRNA) molecules. The structure of crRNA molecules is already established and explained in more detail in Jore et al. (2011) Nature Structural & Molecular Biology 18: 529-537. In brief, a mature crRNA of type I-E is often 61 nucleotides long and consists of a 5' "handle" region of 8 nucleotides, the "spacer" sequence of 32 nucleotides, and a 3' sequence of 21 nucleotides which form a hairpin with a tetranucleotide loop. However, the RNA used in the invention does not have to be designed strictly to the design of naturally occurring crRNA, whether in length, regions or specific RNA sequences. What is clear though, is that RNA molecules for use in the invention may be designed based on gene sequence information in the public databases or newly discovered, and then made artificially, e.g. by chemical synthesis in whole or in part. The RNA molecules of the invention may also be designed and produced by way of expression in genetically modified cells or cell free expression systems and this option may include synthesis of some or all of the RNA sequence.

The structure and requirements of crRNA has also been described in Semenova E et al. (2011) Proc. Natl. Acad. Sci. USA 108: 10098-10103. There is a so-called "SEED" portion forming the 5' end of the spacer sequence and which is flanked 5' thereto by the 5' handle of 8 nucleotides. Semenova et al. (2011) have found that all residues of the SEED sequence should be complementary to the target sequence, although for the residue at position 6, a mismatch may be tolerated. Similarly, when designing and making an RNA component of a ribonucleoprotein complex of the invention directed at a target locus (i.e. sequence), the necessary match and mismatch rules for the SEED sequence can be applied.

The invention therefore includes a method of detecting and/or locating a single base change in a target nucleic acid molecule comprising contacting a nucleic acid sample with a ribonucleoprotein complex of the invention as hereinbefore described, or with a Cascade complex and separate RNA component of the invention as hereinbefore described, and wherein the sequence of the RNA component (including when in the ribonucleoprotein complex) is such that it discriminates between a normal allele and a mutant allele by virtue of a single base change at position 6 of a contiguous sequence of 8 nucleotide residues.

In embodiments of the invention, the RNA molecule may have a length in the range of 35-75 residues. In preferred embodiments, the portion of the RNA which is complementary to and used for targeting a desired nucleic acid sequence is 32 or 33 residues long. (In the context of a naturally occurring crRNA, this would correspond to the spacer portion; as shown in FIG. 1 of Semenova et al. (2011)).

A ribonucleoprotein complex of the invention may additionally have an RNA component comprising 8 residues 5' to the RNA sequence which has at least substantial complementarity to the nucleic acid target sequence. (The RNA sequence having at least substantial complementarity to the nucleic acid target sequence would be understood to correspond in the context of a crRNA as being the spacer sequence. The 5' flanking sequence of the RNA would be considered to correspond to the 5' handle of a crRNA. This is shown in FIG. 1 of Semenova et al. (2011)).

A ribonucleoprotein complex of the invention may have a hairpin and tetranucleotide loop forming sequence 3' to the RNA sequence which has at least substantial complementarity to the DNA target sequence. (In the context of crRNA, this would correspond to a 3' handle flanking the spacer sequence as shown in FIG. 1 of Semenova et al. (2011)).

In some embodiments, the RNA may be a CRISPR RNA (crRNA).

The Cascade proteins and complexes of the invention may be characterised in vitro in terms of its activity of association with the RNA guiding component to form a ribonucleoprotein complex in the presence of the target nucleic acid (which may be DNA or RNA). An electrophoretic mobility shift assay (EMSA) may be used as a functional assay for interaction of complexes of the invention with their nucleic acid targets. Basically, Cascade-functional moiety complex of the invention is mixed with nucleic acid targets and the stable interaction of the Cascade-functional moiety complex is monitored by EMSA or by specific readout out the functional moiety, for example endonucleolytic cleavage of target DNA at the desired site. This can be determined by further restriction fragment length analysis using commercially available enzymes with known specificities and cleavage sites in a target DNA molecule.

Visualisation of binding of Cascade proteins or complexes of the invention to DNA or RNA in the presence of guiding RNA may be achieved using scanning/atomic force microscopy (SFM/AFM) imaging and this may provide an assay for the presence of functional complexes of the invention.

The invention also provides a nucleic acid molecule encoding at least one clustered regularly interspaced short palindromic repeat (CRISPR)-associated protein subunit selected from:
  a. a Cse1 subunit having an amino acid sequence of SEQ ID NO: 1 or a sequence of at least 9% identity therewith;
  b. a Cse2 subunit having an amino acid sequence of SEQ ID NO:2 or a sequence of at least 20% identity therewith;
  c. a Cas7 subunit having an amino acid sequence of SEQ ID NO:3 or a sequence of at least 18% identity therewith;
  d. a Cas5 subunit having an amino acid sequence of SEQ ID NO:4 or a sequence of at least 17% identity therewith;
  e. a Cas6 subunit having an amino acid sequence of SEQ ID NO:5 or a sequence of at least 16% identity therewith; and
wherein at least a, b, c, d or e includes an additional amino acid sequence having nucleic acid or chromatin modifying, visualising, transcription activating or transcription repressing activity.

The additional amino acid sequence having nucleic acid or chromatin modifying, visualising, transcription activating or transcription repressing activity is preferably fused to the CRISPR-associated protein subunit.

In the nucleic acids of the invention defined above, the nucleotide sequence may be that which encodes the respective SEQ ID NO: 1, SEQ ID NO:2, SEQ ID NO:3, SEQ ID NO:4 or SEQ ID NO:5, or in defining the range of variant sequences thereto, it may be a sequence hybridisable to that nucleotide sequence, preferably under stringent conditions, more preferably very high stringency conditions. A variety of stringent hybridisation conditions will be familiar to the skilled reader in the field. Hybridization of a nucleic acid molecule occurs when two complementary nucleic acid molecules undergo an amount of hydrogen bonding to each other known as Watson-Crick base pairing. The stringency of hybridization can vary according to the environmental (i.e. chemical/physical/biological) conditions surrounding the nucleic acids, temperature, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Allows Sequences that Share at Least 80% Identity to Hybridize)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Allows Sequences that Share at Least 50% Identity to Hybridize)
  Hybridization: 6×SSC at RT to 55° C. for 16-20 hours
  Wash at least twice: 2×-3×SSC at RT to 55° C. for 20-30 minutes each.

The nucleic acid molecule may be an isolated nucleic acid molecule and may be an RNA or a DNA molecule.

The additional amino acid sequence may be selected from a helicase, a nuclease, a nuclease-helicase (e.g. Cas3), a DNA methyltransferase (e.g. Dam), a DNA demethylase, a histone methyltransferase, a histone demethylase, an acetylase, a deacetylase, a phosphatase, a kinase, a transcription (co-)activator, an RNA polymerase subunit, a transcription repressor, a DNA binding protein, a DNA structuring protein, a marker protein, a reporter protein, a fluorescent protein, a ligand binding protein (e.g. mCherry or a heavy metal binding protein), a signal peptide (e.g. Tat-signal sequence), a subcellular localisation sequence (e.g. nuclear localisation sequence), or an antibody epitope. The additional amino acid sequence may be, or from a different protein from the organism from which the relevant Cascade protein subunit(s) are derived.

The invention includes an expression vector comprising a nucleic acid molecule as hereinbefore defined. One expression vector may contain the nucleotide sequence encoding a single Cascade protein subunit and also the nucleotide sequence encoding the additional amino acid sequence, whereby on expression the subunit and additional sequence are fused. Other expression vectors may comprise nucleotide sequences encoding just one or more Cascade protein subunits which are not fused to any additional amino acid sequence.

The additional amino acid sequence with nucleic acid or chromatin modifying activity may be fused to any of the Cascade subunits via a linker polypeptide. The linker may be of any length up to about 60 or up to about 100 amino acid residues. Preferably the linker has a number of amino acids in the range 10 to 60, more preferably 10-20. The amino acids are preferably polar and/or small and/or charged amino acids (e.g. Gln, Ser, Thr, Pro, Ala, Glu, Asp, Lys, Arg, His, Asn, Cys, Tyr). The linker peptide is preferably designed to obtain the correct spacing and positioning of the fused functional moiety and the subunit of Cascade to which the moiety is fused to allow proper interaction with the target nucleotide.

An expression vector of the invention (with or without nucleotide sequence encoding amino acid residues which on expression will be fused to a Cascade protein subunit) may further comprise a sequence encoding an RNA molecule as hereinbefore defined. Consequently, such expression vectors can be used in an appropriate host to generate a ribonucleoprotein of the invention which can target a desired nucleotide sequence.

Accordingly, the invention also provides a method of modifying, visualising, or activating or repressing transcription of a target nucleic acid comprising contacting the nucleic acid with a ribonucleoprotein complex as hereinbefore defined. The modifying may be by cleaving the nucleic acid or binding to it.

The invention also includes a method of modifying, visualising, or activating or repressing transcription of a target nucleic acid comprising contacting the nucleic acid with a Cascade protein complex as hereinbefore defined, plus an RNA molecule as hereinbefore defined.

In accordance with the above methods, the modification, visualising, or activating or repressing transcription of a target nucleic acid may therefore be carried out in vitro and in a cell free environment; i.e. the method is carried out as a biochemical reaction whether free in solution or whether involving a solid phase. Target nucleic acid may be bound to a solid phase, for example.

In a cell free environment, the order of adding each of the target nucleic acid, the Cascade protein complex and the RNA molecule is at the option of the average skilled person. The three components may be added simultaneously, sequentially in any desired order, or separately at different times and in a desired order. Thus it is possible for the target nucleic acid and RNA to be added simultaneously to a reaction mix and then the Cascade protein complex of the invention to be added separately and later in a sequence of specific method steps.

The modification, visualising, or activating or repressing transcription of a target nucleic acid may be made in situ in a cell, whether an isolated cell or as part of a multicellular tissue, organ or organism. Therefore in the context of whole tissue and organs, and in the context of an organism, the method can be carried out in vivo or it can be carried out by isolating a cell from the whole tissue, organ or organism and then returning the cell treated with ribonucleoprotein complex to its former location, or a different location, whether within the same or a different organism. Thus the method would include allografts, autografts, isografts and xenografts.

In these embodiments, the ribonucleoprotein complex or the Cascade protein complex of the invention requires an appropriate form of delivery into the cell, which will be well known to persons of skill in the art, including microinjection, whether into the cell cytoplasm or into the nucleus.

Also when present separately, the RNA molecule requires an appropriate form of delivery into a cell, whether simultaneously, separately or sequentially with the Cascade protein complex. Such forms of introducing RNA into cells are well known to a person of skill in the art and may include in vitro or ex vivo delivery via conventional transfection methods. Physical methods, such as microinjection and electroporation, as well as calcium co-precipitation, and commercially available cationic polymers and lipids, and cell-penetrating peptides, cell-penetrating particles (gene-gun) may each be used. For example, viruses may be used as delivery vehicles, whether to the cytoplasm and/or nucleus—e.g. via the (reversible) fusion of Cascade protein complex of the invention or a ribonucleoprotein complex of the invention to the viral particle. Viral delivery (e.g. adenovirus delivery) or Agrobacterium-mediated delivery may be used.

The invention also includes a method of modifying visualising, or activating or repressing transcription of a target nucleic acid in a cell, comprising transfecting, transforming or transducing the cell with any of the expression vectors as hereinbefore described. The methods of transfection, transformation or transduction are of the types well known to a person of skill in the art. Where there is one expression vector used to generate expression of a Cascade complex of the invention and when the RNA is added directly to the cell then the same or a different method of transfection, transformation or transduction may be used. Similarly, when there is one expression vector being used to generate expression of a Cascade-functional fusion complex of the invention and when another expression vector is being used to generate the RNA in situ via expression, then the same or a different method of transfection, transformation or transduction may be used.

In other embodiments, mRNA encoding the Cascade complex of the invention is introduced into a cell so that the Cascade complex is expressed in the cell. The RNA which guides the Cascade complex to the desired target sequence is also introduced into the cell, whether simultaneously, separately or sequentially from the mRNA, such that the necessary ribonucleoprotein complex is formed in the cell.

In the aforementioned methods of modifying or visualising a target nucleic acid, the additional amino acid sequence may be a marker and the marker associates with the target nucleic acid; preferably wherein the marker is a protein; optionally a fluorescent protein, e.g. green fluorescent protein (GFP) or yellow fluorescent protein (YFP) or mCherry. Whether in vitro, ex vivo or in vivo, then methods of the invention can be used to directly visualise a target locus in a nucleic acid molecule, preferably in the form of a higher order structure such as a supercoiled plasmid or chromosome, or a single stranded target nucleic acid such as mRNA. Direct visualisation of a target locus may use electron micrography, or fluorescence microscopy.

Other kinds of label may be used to mark the target nucleic acid including organic dye molecules, radiolabels and spin labels which may be small molecules.

In methods of the invention described above, the target nucleic acid is DNA; preferably dsDNA although the target can be RNA; preferably mRNA.

In methods of the invention for modifying, visualising, activating transcription or repressing transcription of a target nucleic acid wherein the target nucleic acid is dsDNA, the additional amino acid sequence with nucleic acid or chromatin modifying activity may be a nuclease or a helicase-nuclease, and the modification is preferably a single stranded or a double stranded break at a desired locus. In this way unique sequence specific cutting of DNA can be engineered by using the Cascade-functional moiety complexes. The chosen sequence of the RNA component of the final ribonucleoprotein complex provides the desired sequence specificity for the action of the additional amino acid sequence.

Therefore, the invention also provides a method of non-homologous end joining of a dsDNA molecule in a cell at a desired locus to remove at least a part of a nucleotide sequence from the dsDNA molecule; optionally to knockout the function of a gene or genes, wherein the method comprises making double stranded breaks using any of the methods of modifying a target nucleic acid as hereinbefore described.

The invention further provides a method of homologous recombination of a nucleic acid into a dsDNA molecule in a cell at a desired locus in order to modify an existing nucleotide sequence or insert a desired nucleotide sequence, wherein the method comprises making a double or single stranded break at the desired locus using any of the methods of modifying a target nucleic acid as hereinbefore described.

The invention therefore also provides a method of modifying, activating or repressing gene expression in an organism comprising modifying, activating transcription or repressing transcription of a target nucleic acid sequence according to any of the methods hereinbefore described, wherein the nucleic acid is dsDNA and the functional moiety is selected from a DNA modifying enzyme (e.g. a demethylase or deacetylase), a transcription activator or a transcription repressor.

The invention additionally provides a method of modifying, activating or repressing gene expression in an organism comprising modifying, activating transcription or repressing transcription of a target nucleic acid sequence according to any of the methods hereinbefore described, wherein the nucleic acid is an mRNA and the functional moiety is a ribonuclease; optionally selected from an endonuclease, a 3' exonuclease or a 5' exonuclease.

In any of the methods of the invention as described above, the cell which is subjected to the method may be a prokaryote. Similarly, the cell may be a eukaryotic cell, e.g. a plant cell, an insect cell, a yeast cell, a fungal cell, a mammalian cell or a human cell. When the cell is of a mammal or human then it can be a stem cell (but may not be any human embryonic stem cell). Such stem cells for use in the invention are preferably isolated stem cells. Optionally in accordance with any method the invention a cell is transfected in vitro.

Preferably though, in any of the methods of the invention, the target nucleic acid has a specific tertiary structure, optionally supercoiled, more preferably wherein the target nucleic acid is negatively supercoiled. Advantageously, the ribonucleoprotein complexes of the invention, whether produced in vitro, or whether formed within cells, or whether formed within cells via expression machinery of the cell, can be used to target a locus which would otherwise be difficult to get access to in order to apply the functional activity of a desired component, whether labelling or tagging of a specific sequence, modification of nucleic acid structure, switching on or off of gene expression, or of modification of the target sequence itself involving single or double stranded cutting followed by insertion of one or more nucleotide residues or a cassette.

The invention also includes a pharmaceutical composition comprising a Cascade protein complex or a ribonucleoprotein complex of the invention as hereinbefore described.

The invention further includes a pharmaceutical composition comprising an isolated nucleic acid or an expression vector of the invention as hereinbefore described.

Also provided is a kit comprising a Casacade protein complex of the invention as hereinbefore described plus an RNA molecule of the invention as hereinbefore described.

The invention includes a Cascade protein complex or a ribonucleoprotein complex or a nucleic acid or a vector, as hereinbefore described for use as a medicament.

The invention allows a variety of possibilities to physically alter DNA of prokaryotic or eukaryotic hosts at a specified genomic locus, or change expression patterns of a gene at a given locus. Host genomic DNA can be cleaved or modified by methylation, visualized by fluorescence, transcriptionally activated or repressed by functional domains such as nucleases, methylases, fluorescent proteins, transcription activators or repressors respectively, fused to suitable Cascade-subunits. Moreover, the RNA-guided RNA-binding ability of Cascade permits the monitoring of RNA trafficking in live cells using fluorescent Cascade fusion proteins, and provides ways to sequester or destroy host mRNAs causing interference with gene expression levels of a host cell.

In any of the methods of the invention, the target nucleic acid may be defined, preferably so if dsDNA, by the presence of at least one of the following nucleotide triplets: 5'-CTT-3', 5'-CAT-3', 5'-CCT-3', or 5'-CTC-3' (or 5'-CUU-3', 5'-CAU-3', 5'-CCU-3', or 5'-CTC-3' if the target is an RNA). The location of the triplet is in the target strand adjacent to the sequence to which the RNA molecule component of a ribonucleoprotein of the invention hybridizes. The triplet marks the point in the target strand sequence at which base pairing with the RNA molecule component of the ribonucleoprotein does not take place in a 5' to 3' (downstream) direction of the target (whilst it takes place upstream of the target sequence from that point subject to the preferred length of the RNA sequence of the RNA molecule component of the ribonucleoprotein of the invention). In the context of a native type I CRISPR system, the triplets correspond to what is known as a "PAM" (protospacer adjacent motif). For ssDNA or ssRNA targets, presence of one of the triplets is not so necessary.

The invention will now be described in detail and with reference to examples and drawings in which:

FIG. 1A through FIG. 1I show the results of gel-shift assays where Cascade binds negatively supercoiled (nSC) plasmid DNA but not relaxed DNA. FIG. 1A: Gel-shift of nSC plasmid DNA with J3-Cascade, containing a targeting (J3) crRNA. pUC-λ was mixed with 2-fold increasing amounts of J3-Cascade, from a pUC-λ: Cascade molar ratio of 1:0.5 up to a 1:256 molar ratio. The first and last lanes contain only pUC-λ. FIG. 1B: Gel-shift as in (A) with R44-Cascade containing a non-targeting (R44) cRNA. FIG. 1C: Gel-shift as in (A) with Nt.BspQI nicked pUC-λ. FIG. 1D: Gel-shift as in (A) with PdmI linearized pUC-λ. FIG. 1E: Fit of the fraction pUC-λ bound to J3-Cascade plotted against the concentration of free J3-Cascade gives the dissociation constant (Kd) for specific binding. FIG. 1F: Fit of the fraction pUC-λ bound to R44-Cascade plotted against the concentration of free R44-Cascade gives the dissociation constant (Kd) for non-specific binding. FIG. 1G: Specific binding of Cascade to the protospacer monitored by restriction analysis, using the unique BsmI restriction site in the protospacer sequence. Lane 1 and 5 contain only pUC-λ. Lane 2 and 6 contain pUC-λ mixed with Cascade. Lane 3 and 7 contain pUC-λ mixed with Cascade and subsequent BsmI addition. Lane 4 and 8 contain pUC-λ mixed with BsmI. FIG. 1H: Gel-shift of pUC-λ bound to Cascade with subsequent Nt.BspQI nicking of one strand of the plasmid. Lane 1 and 6 contain only pUC-λ. Lane 2 and 7 contain pUC-λ mixed with Cascade. Lane 3 and 8 contain pUC-λ mixed with Cascade and subsequent Nt.BspQI nicking. Lane 4 and 9 contain pUC-λ mixed with Cascade, followed by addition of a ssDNA probe complementary to the displaced strand in the R-loop and subsequent nicking with Nt.BspQI. Lane 5 and 10 contain pUC-λ nicked with Nt.BspQI. FIG. 1I: Gel-shift of pUC-λ bound to Cascade with subsequent EcoRI cleavage of both strands of the plasmid. Lane 1 and 6 contain only pUC-λ. Lane 2 and 7 contain pUC-λ mixed with Cascade. Lane 3 and 8 contain pUC-λ mixed with Cascade and subsequent EcoRI cleavage. Lane 4 and 9 contain pUC-λ mixed with Cascade, followed by addition of a ssDNA probe complementary to the displaced strand in the R-loop and subsequent cleavage with EcoRI. Lane 5 and 10 contain pUC-λ cleaved with EcoRI.

FIG. 2, panels A-P, show scanning force micrographs demonstrating how Cascade induces bending of target DNA upon protospacer binding. The figure shows scanning force microscopy images of nSC plasmid DNA with J3-Cascade containing a targeting (J3) crRNA. pUC-λ was mixed with J3-Cascade at a pUC-λ: Cascade ratio of 1:7. Each image shows a 500×500 nm surface area. White dots correspond to Cascade.

FIG. 3A, panels A-I, show how BiFC analysis reveals that Cascade and Cas3 interact upon target recognition. FIG. 3A, panel A: Venus fluorescence of cells expressing CascadeΔCse1 and CRISPR 7Tm, which targets 7 protospacers on the phage λ genome, and Cse1-N155Venus and Cas3-C85Venus fusion proteins. FIG. 3A, panel B: Brightfield image of the cells in (A). FIG. 3A, panel C: Overlay of (A) and (B). FIG. 3A, panel D: Venus fluorescence of phage λ infected cells expressing CascadeΔCse1 and CRISPR 7Tm, and Cse1-N155Venus and Cas3-C85Venus fusion proteins. FIG. 3A, panel E: Brightfield image of the cells in (G). FIG. 3A, panel F: Overlay of (G) and (H). FIG. 3A, panel G: Venus fluorescence of phage λ infected cells expressing CascadeΔCse1 and non-targeting CRISPR R44, and N155Venus and C85Venus proteins. FIG. 3A, panel H: Brightfield image of the cells in (J). FIG. 3A, panel I: Overlay of (J) and (K). FIG. 3B: Average of the fluorescence intensity of 4-7 individual cells of each strain, as determined using the profile tool of LSM viewer (Carl Zeiss).

FIG. 4A and FIG. 4B show Cas3 nuclease and helicase activities during CRISPR-interference. FIG. 4A: Competent BL21-AI cells expressing Cascade, a Cas3 mutant and CRISPR J3 were transformed with pUC-λ. Colony forming units per microgram pUC-λ (cfu/µg DNA) are depicted for each of the strains expressing a Cas3 mutant. Cells expressing wt Cas3 and CRISPR J3 or CRISPR R44 serve as positive and negative controls, respectively. FIG. 4B: BL21-AI cells carrying Cascade, Cas3 mutant, and CRISPR encoding plasmids as well as pUC-λ are grown under conditions that suppress expression of the cas genes and CRISPR. At t=0 expression is induced. The percentage of cells that lost pUC-λ over time is shown, as determined by the ratio of ampicillin sensitive and ampicillin resistant cells.

FIG. 5A through FIG. 5H show how a Cascade-Cas3 fusion complex provides in vivo resistance and has in vitro nuclease activity. FIG. 5A: Coomassie Blue stained SDS-PAGE of purified Cascade and Cascade-Cas3 fusion complex. FIG. 5B: Efficiency of plaquing of phage λ on cells expressing Cascade-Cas3 fusion complex and a targeting (J3) or non-targeting (R44) CRISPR and on cells expressing Cascade and Cas3 separately together with a targeting (J3) CRISPR. FIG. 5C: Gel-shift (in the absence of divalent metal ions) of nSC target plasmid with J3-Cascade-Cas3 fusion complex. pUC-λ was mixed with 2-fold increasing amounts of J3-Cascade-Cas3, from a pUC-λ:J3-Cascade-Cas3 molar ratio of 1:0.5 up to a 1:128 molar ratio. The first and last lane contain only pUC-λ. FIG. 5D: Gel-shift (in the absence of divalent metal ions) of nSC non-target plasmid with J3-Cascade-Cas3 fusion complex. pUC-p7 was mixed with 2-fold increasing amounts of J3-Cascade-Cas3, from a pUC-p7:J3-Cascade-Cas3 molar ratio of 1:0.5 up to a 1:128 molar ratio. The first and last lane contain only pUC-p7. FIG. 5E: Incubation of nSC target plasmid (pUC-λ, left) or nSC non-target plasmid (pUC-p7, right) with J3-Cascade-Cas3 in the presence of 10 mM $MgCl_2$. Lane 1 and 7 contain only plasmid. FIG. 5F: Assay as in (E) in the presence of 2 mM ATP. FIG. 5G: Assay as in (E) with the mutant J3-Cascade-Cas3K320N complex. FIG. 5H: Assay as in (G) in the presence of 2 mM ATP.

Figure 8:
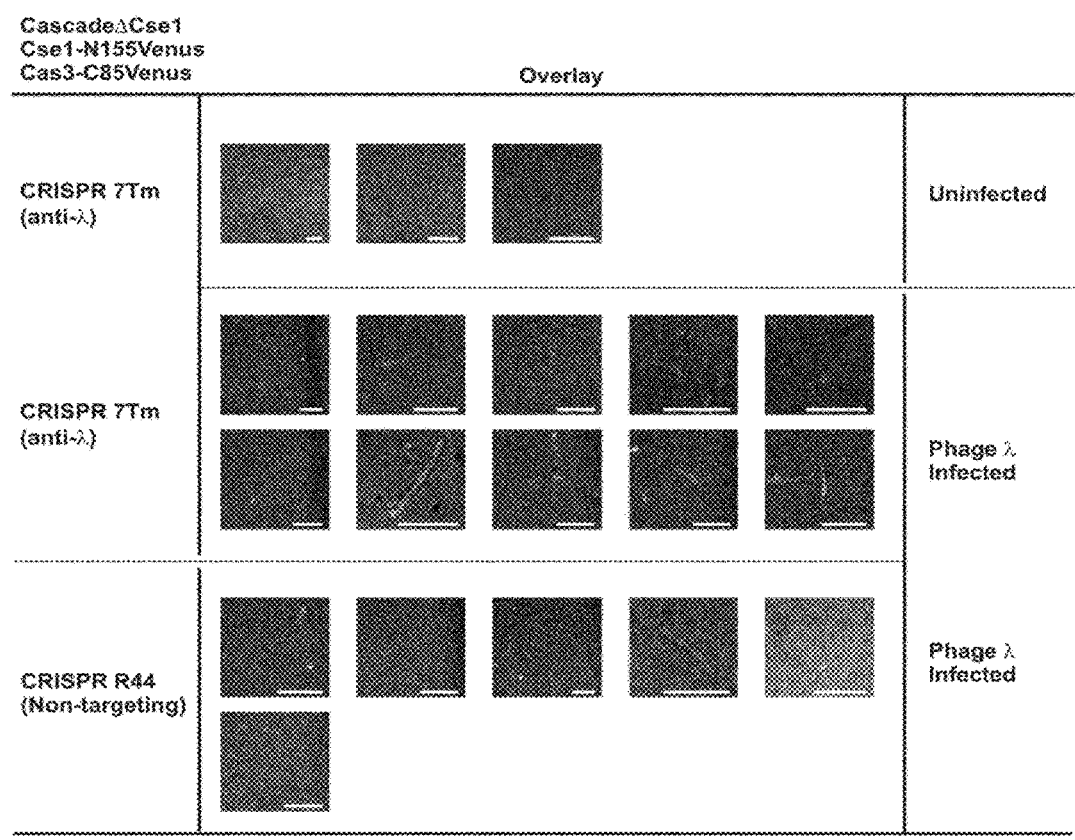

FIG. 8 shows how BiFC analysis reveals that Cascade and Cas3 interact upon target recognition. Overlay of Brightfield image and Venus fluorescence of cells expressing Cascade without Cse1, Cse1-N155Venus and Cas3-C85Venus and either CRISPR 7Tm, which targets 7 protospacers on the phage Lambda genome, or the non-targeting CRISPR R44. Cells expressing CRISPR 7Tm are fluorescent only when infected with phage Lambda, while cells expressing CRISPR R44 are non-fluorescent. The highly intense fluorescent dots (outside cells) are due to light-reflecting salt crystals. White bars correspond to 10 micron.

FIG. 9 shows pUC-λ, sequences of 4 clones [SEQ ID NOs: 39-42] encoding CRISPR J3, Cascade and Cas3 (wt or S483AT485A) indicate that these are escape mutants carrying (partial) deletions of the protospacer or carrying a single point mutation in the seed region, which explains the inability to cure these plasmids.

Figure 10A:
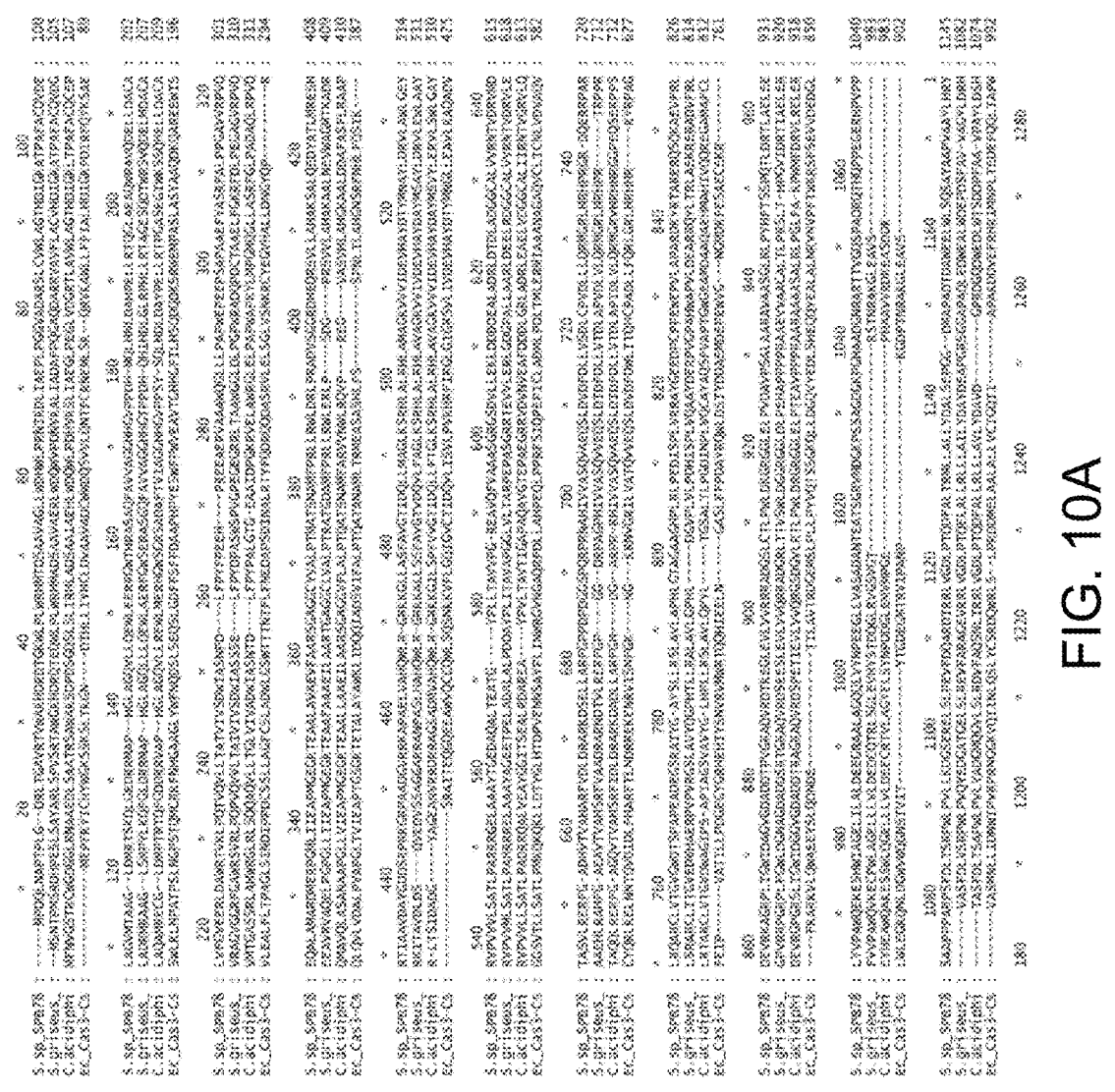

FIG. 10A and FIG. 10B show sequence alignments of cas3 genes from organisms containing the Type I-E CRISPR/Cas system. Alignment of cas3-cse1 genes from *Streptomyces* sp. SPB78 ($1^{st}$ sequence, Accession Number: ZP_07272643.1) [SEQ ID NO: 43], in *Streptomyces griseus* ($2^{nd}$ sequence, Accession Number YP_001825054) [SEQ ID NO: 44], and in *Catenulispora acidiphila* DSM 44928 ($3^{rd}$ sequence, Accession Number YP_003114638) [SEQ ID NO: 45] and an artificial *E. coli* Cas3-Cse1 fusion protein [SEQ ID NO: 46] which includes the polypeptide linker sequence from *S. griseus*.

Figure 11:
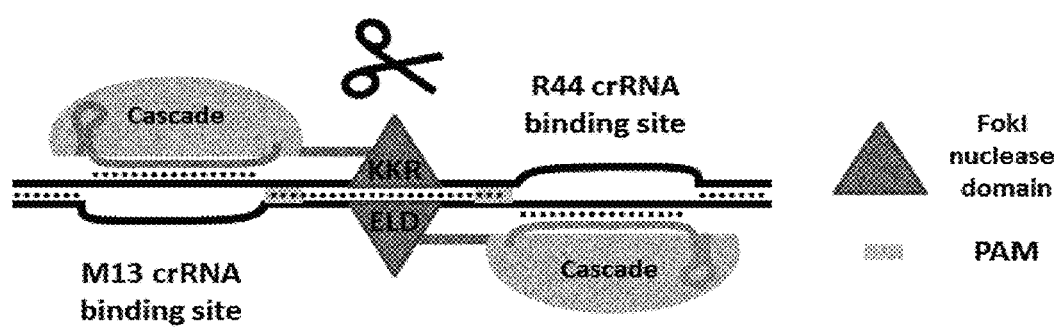

FIG. 11 shows the design of a Cascade$^{KKR/ELD}$ nuclease pair in which FokI nuclease domains are mutated such that only heterodimers consisting of KKR and ELD nuclease domains are and the distance between the opposing binding sites may be varied to determine the optimal distance between a Cascade nuclease pair.

Figure 12:
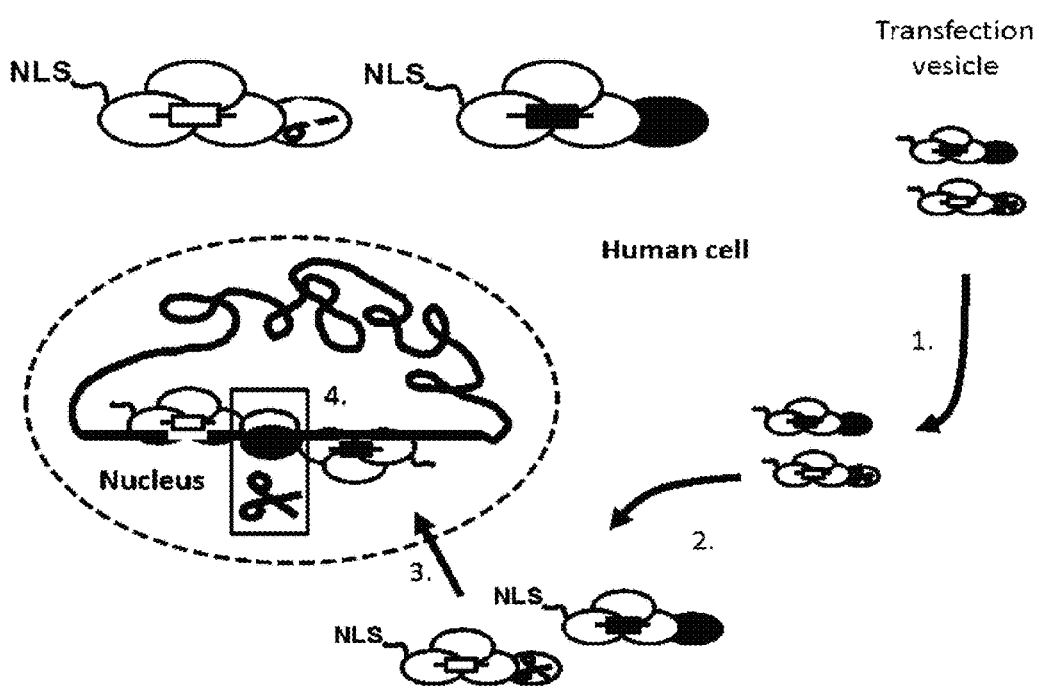

FIG. 12 is a schematic diagram showing genome targeting by a Cascade-FokI nuclease pair.

Figure 13:
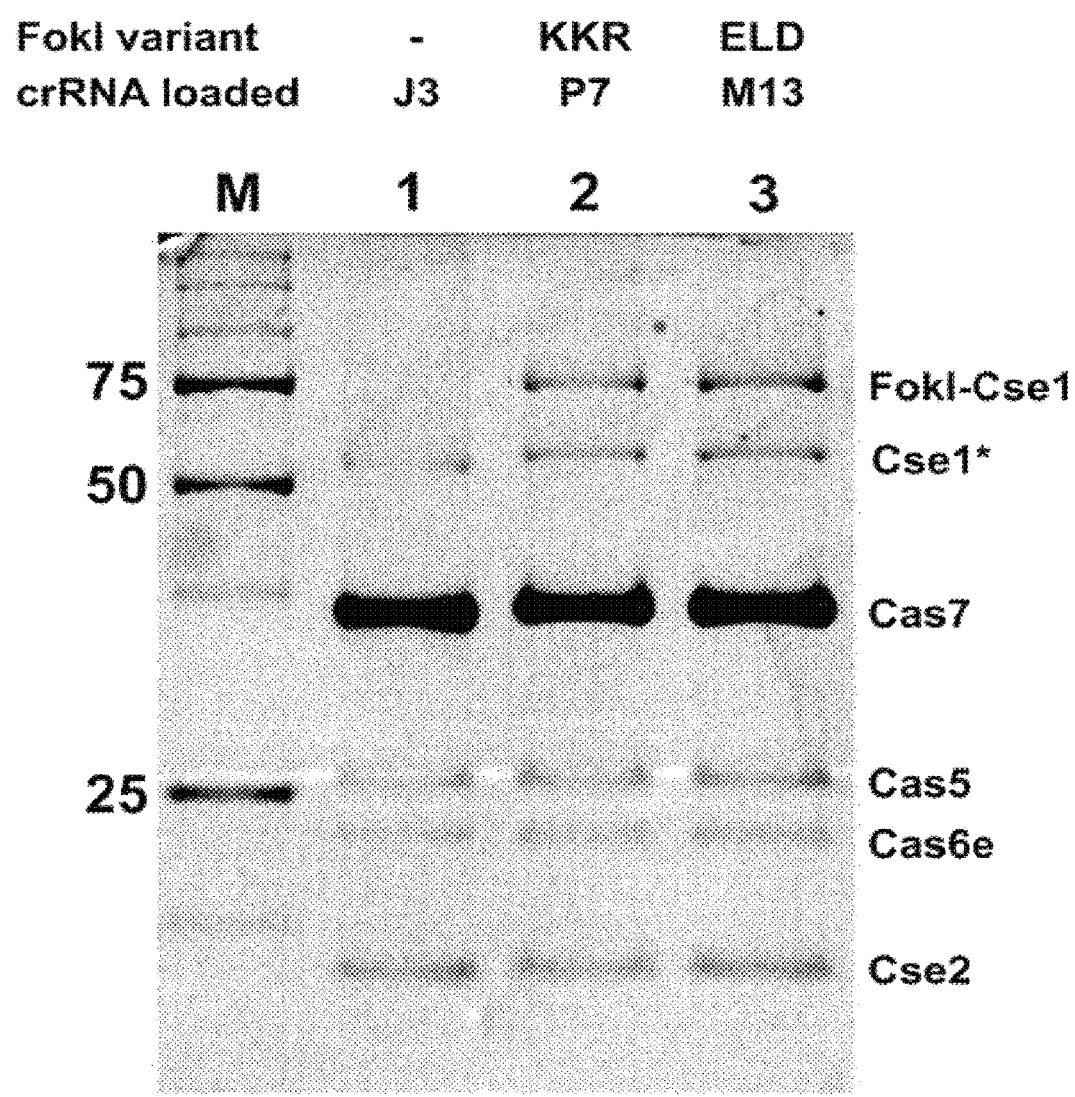

FIG. 13 shows an SDS PAGE gel of Cascade-nuclease complexes.

Figure 14A:
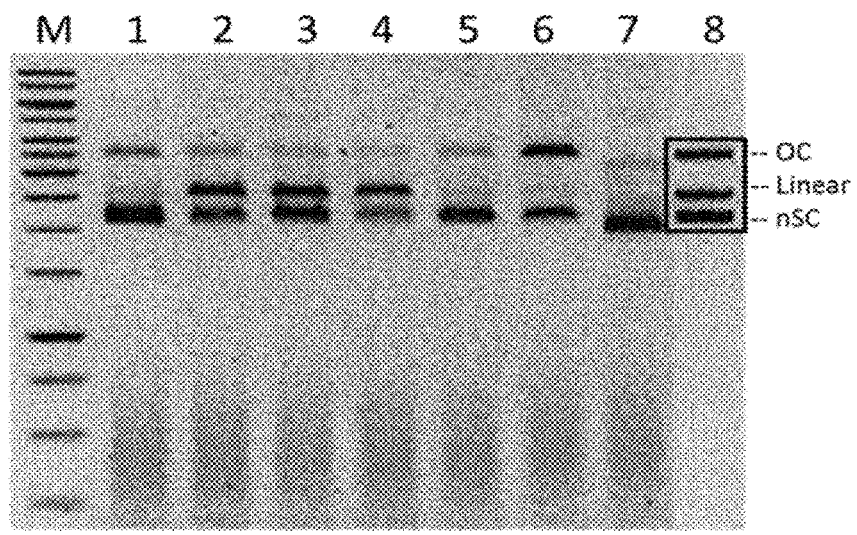
Figure 14B:
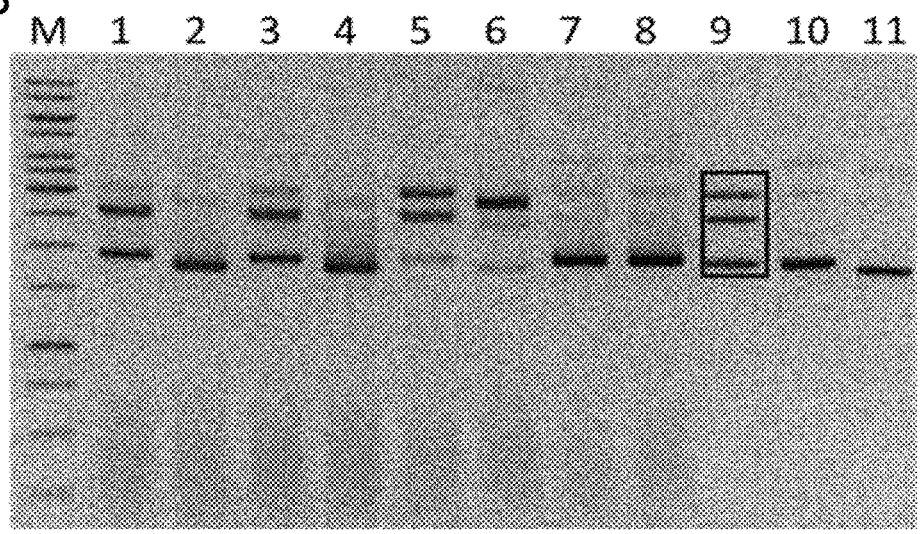

FIG. 14A and FIG. 14B show electrophoresis gels of in vitro cleavage assays of Cascade$^{KKR/ELD}$ on plasmid DNA.

Figure 15A:
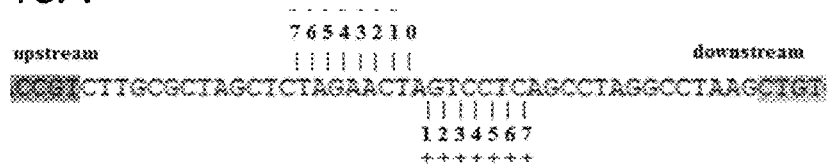
Figure 15B:
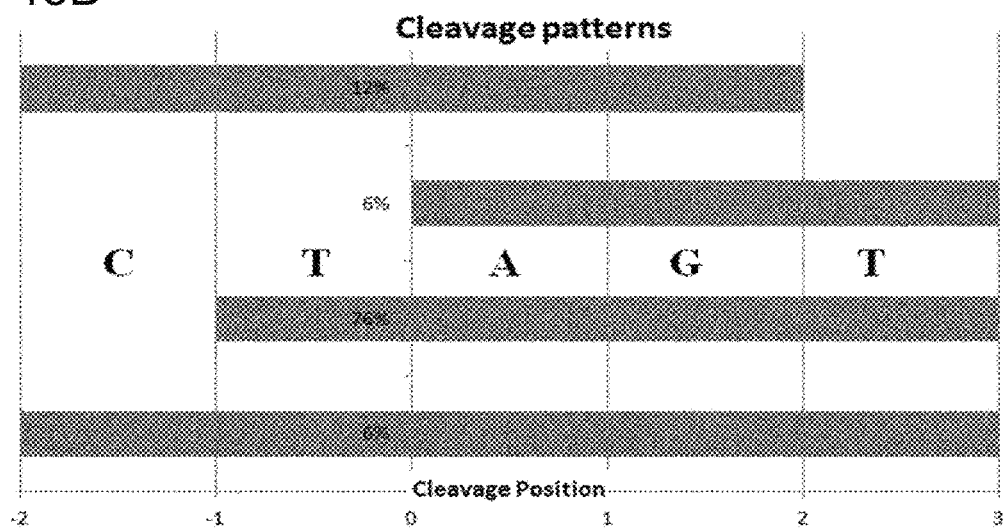

FIG. 15A and FIG. 15B show Cascade$^{KKR/ELD}$ cleavage patterns and frequency [SEQ ID NO: 47].

EXAMPLES

Materials and Methods Used

Strains, Gene Cloning, Plasmids and Vectors

*E. coli* BL21-AI and *E. coli* BL21 (DE3) strains were used throughout. Table 1 lists all plasmids used in this study. The previously described pWUR408, pWUR480, pWUR404 and pWUR547 were used for production of Strep-tag II R44-Cascade, and pWUR408, pWUR514 and pWUR630 were used for production of Strep-tag II J3-Cascade (Jore et al., (2011) Nature Structural & Molecular Biology 18, 529-536; Semenova et al., (2011) Proceedings of the National Academy of Sciences of the United States of America 108, 10098-10103.) pUC-λ (pWUR610) and pUC-p7 (pWUR613) have been described elsewhere (Jore et al., 2011; Semenova et al., 2011). The C85Venus protein is encoded by pWUR647, which corresponds to pET52b (Novagen) containing the synthetic GA1070943 construct (Table 2) (Geneart) cloned between the BamHI and NotI sites. The N155Venus protein is encoded by pWUR648, which corresponds to pRSF1b (Novagen) containing the synthetic GA1070941 construct (Table 2) (Geneart) cloned between the NotI and XhoI sites. The Cas3-C85Venus fusion protein is encoded by pWUR649, which corresponds to pWUR647 containing the Cas3 amplification product using primers BG3186 and BG3213 (Table 3) between the NcoI and BamHI sites. The CasA-N155Venus fusion protein is encoded by pWUR650, which corresponds to pWUR648 containing the CasA amplification product using primers BG3303 and BG3212 (Table 3) between the NcoI and BamHI sites. CRISPR 7Tm is encoded by pWUR651, which corresponds to pACYCDuet-1 (Novagen) containing the synthetic GA1068859 construct (Table 2) (Geneart) cloned between the NcoI and KpnI sites. The Cascade encoding pWUR400, the CascadeΔCse1 encoding WUR401 and the Cas3 encoding pWUR397 were described previously (Jore et al., 2011). The Cas3H74A encoding pWUR652 was constructed using site directed mutagenesis of pWUR397 with primers BG3093, BG3094 (Table 3).

TABLE 1

Plasmids used

| Plasmids | Description and order of genes (5'-3') | Restriction sites | Primers | Source |
|---|---|---|---|---|
| pWUR397 | cas3 in pRSF-1b, no tags | | | 1 |
| pWUR400 | casA-casB-casC-casD-casE in pCDF-1b, no tags | | | 1 |
| pWUR401 | casB-casC-casD-casE in pCDF-1b, no tags | | | 1 |
| pWUR404 | casE in pCDF-1b, no tags | | | 1 |

TABLE 1-continued

Plasmids used

| Plasmids | Description and order of genes (5'-3') | Restriction sites | Primers | Source |
|---|---|---|---|---|
| pWUR408 | casA in pRSF-1b, no tags | | | 1 |
| pWUR480 | casB with Strep-tag II (N-term)-casC-casD in pET52b | | | 1 |
| pWUR514 | casB with Strep-tag II (N-term)-casC-casD-CasE in pET52b | | | 2 |
| pWUR547 | *E. coli* R44 CRISPR, 7x spacer nr. 2, in pACYCDuet-1 | | | 2 |
| pWUR613 | pUC-p7; pUC19 containing R44-protospacer on a 350 bp phage P7 amplicon | | | 2 |
| pWUR630 | CRISPR poly J3, 5x spacer J3 in pACYCDuet-1 | NcoI/KpnI | | This study |
| pWUR610 | pUC-λ; pUC19 containing J3-protospacer on a 350 bp phage λ amplicon | | | 3 |
| pWUR647 | C85Venus; GA1070943 (Table S1) in pET52b | BamHI/NotI | | This study |
| pWUR648 | N155Venus; GA1070941 (Table S1) in pRSF1b | NotI/XhoI | | This study |
| pWUR649 | cas3-C85Venus; pWUR647 containing cas3 amplicon | NcoI/BamHI | BG3186 + BG3213 | This study |
| pWUR650 | casA-N155Venus pWUR648 containing casA amplicon | NcoI/NotI | BG3303 + BG3212 | This study |
| pWUR651 | CRISPR 7Tm; GA1068859 (Table S1) in pACYCDuet-1 | NcoI/KpnI | | This study |
| | casB with Strep-tag II (N-term)-casC-casD-CasE in pCDF-1b | | | This study |
| | cas3-casA fusion | | | This study |
| | cas3H74A-CasA fusion | | | This study |
| | cas3D75A-CasA fusion | | | This study |
| | cas3K320N-CasA fusion | | | This study |
| | cas3D452N-CasA fusion | | | This study |

Source 1 in the table above is Brouns et al (2008) Science 321, 960-964.
Source 2 in the table above is Jore et al (2011) Nature Structural & Molecular Biology 18: 529-537.

TABLE 2

Synthetic Constructs

GA1070943

ACTGGAAAGCGGGCAGTGAAAGGAAGGCCCATGAGGCCAGTTAATTAAGC
GGATCCTGGCGGCGGCAGCGGCGGCGGCAGCGACAAGCAGAAGAACGGCA
TCAAGGCGAACTTCAAGATCCGCCACAACATCGAGGACGGCGGCGTGCAG
CTCGCCGACCACTACCAGCAGAACACCCCCATCGGCGACGGCCCCGTGCT
GCTGCCCGACAACCACTACCTGAGCTACCAGTCCGCCCTGAGCAAAGACC
CCAACGAGAAGCGCGATCACATGGTCCTGCTGGAGTTCGTGACCGCCGCC
GGGATCACTCTCGGCATGGACGAGCTGTACAAGTAAGCGGCCGCGGCGCG
CCTAGGCCTTGACGGCCTTCCTTCAATTCGCCCTATAGTGAG
[SEQ ID NO: 6]

GA1070941

CACTATAGGGCGAATTGGCGGAAGGCCGTCAAGGCCGCATTTAATTAAGC
GGCCGCAGGCGGCGGCAGCGGCGGCGGCAGCATGGTGAGCAAGGGCGAGG

TABLE 2-continued

Synthetic Constructs

```
AGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTA
CGGCAAGCTGACCCTGAAGCTCATCTGCACCACCGGCAAGCTGCCCGTGC
CCTGGCCCACCCTCGTGACCACCCTCGGCTACGGCCTGCAGTGCTTCGCC
CGCTACCCCGACCACATGAAGCAGCACGACTTCTTCAAGTCCGCCATGCC
CGAAGGCTACGTCCAGGAGCGCACCATCTTCTTCAAGGACGACGGCAACT
ACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCA
CAAGCTGGAGTACAACTACAACAGCCACAACGTCTATATCACGGCCTAAC
TCGAGGGCGCGCCCTGGGCCTCATGGGCCTTCCGCTCACTGCCCGCTTTC
CAG [SEQ ID NO: 7]
```

GA1068859

```
CACTATAGGGCGAATTGGCGGAAGGCCGTCAAGGCCGCATGAGCTCCATG
GAAACAAAGAATTAGCTGATCTTTAATAATAAGGAAATGTTACATTAAGG
TTGGTGGGTTGTTTTTATGGGAAAAAATGCTTTAAGAACAAATGTATACT
TTTAGAGAGTTCCCCGCGCCAGCGGGGATAAACCGGGCCGATTGAAGGTC
CGGTGGATGGCTTAAAAGAGTTCCCCGCGCCAGCGGGGATAAACCGCCGC
AGGTACAGCAGGTAGCGCAGATCATCAAGAGTTCCCCGCGCCAGCGGGGA
TAAACCGACTTCTCTCCGAAAAGTCAGGACGCTGTGGCAGAGTTCCCCGC
GCCAGCGGGGATAAACCGCCTACGCGCTGAACGCCAGCGGTGTGGTGAAT
GAGTTCCCCGCGCCAGCGGGGATAAACCGGTGTGGCCATGCACGCCTTTA
ACGGTGAACTGGAGTTCCCCGCGCCAGCGGGGATAAACCGCACGAACTCA
GCCAGAACGACAAACAAAAGGCGAGTTCCCCGCGCCAGCGGGGATAAACC
GGCACCAGTACGCGCCCACGCTGACGGTTTCTGAGTTCCCCGCGCCAGC
GGGGATAAACCGCAGCTCCCATTTTCAAACCCAGGTACCCTGGGCCTCAT
GGGCCTTCCGCTCACTGCCCGCTTTCCAG [SEQ ID NO: 8]
```

GA1047360

```
GAGCTCCCGGGCTGACGGTAATAGAGGCACCTACAGGCTCCGGTAAAACG
GAAACAGCGCTGGCCTATGCTTGGAAACTTATTGATCAACAAATTGCGGA
TAGTGTTATTTTTGCCCTCCCAACACAAGCTACCGCGAATGCTATGCTTA
CGAGAATGGAAGCGAGCGCGAGCCACTTATTTTCATCCCCAAATCTTATT
CTTGCTCATGGCAATTCACGGTTTAACCACCTCTTTCAATCAATAAAATC
ACGCGCGATTACTGAACAGGGGCAAGAAGAAGCGTGGGTTCAGTGTTGTC
AGTGGTTGTCACAAAGCAATAAGAAAGTGTTTCTTGGGCAAATCGGCGTT
TGCACGATTGATCAGGTGTTGATTTCGGTATTGCCAGTTAAACACCGCTT
TATCCGTGGTTTGGGAATTGGTAGATCTGTTTTAATTGTTAATGAAGTTC
ATGCTTACGACACCTATATGAACGGCTTGCTCGAGGCAGTGCTCAAGGCT
CAGGCTGATGTGGGAGGGAGTGTTATTCTTCTTTCCGCAACCCTACCAAT
GAAACAAAAACAGAAGCTTCTGGATACTTATGGTCTGCATACAGATCCAG
TGGAAAATAACTCCGCATATCCACTCATTAACTGGCGAGGTGTGAATGGT
GCGCAACGTTTTGATCTGCTAGCGGATCCGGTACC [SEQ ID NO: 9]
```

TABLE 3

Primers

| | |
|---|---|
| BG3186 | ATAGCGCCATGGAACCTTTTAAATATATATGCCATTA [SEQ ID NO: 10] |
| BG3213 | ACAGTGGGATCCGCTTTGGGATTTGCAGGGATGACTCTGGT [SEQ ID NO: 11] |
| BG3303 | ATAGCGTCATGAATTTGCTTATTGATAACTGGATTCCTGTACG [SEQ ID NO: 12] |
| BG3212 | ACAGTGGCGGCCGCGCCATTTGATGGCCCTCCTTGCGGTTTTAA [SEQ ID NO: 13] |
| BG3076 | CGTATATCAAACTTTCCAATAGCATGAAGAGCAATGAAAAATAAC [SEQ ID NO: 14] |
| BG3449 | ATGATACCGCGAGACCCACGCTC [SEQ ID NO: 15] |
| BG3451 | CGGATAAAGTTGCAGGACCACTTC [SEQ ID NO: 16] |

Protein Production and Purification

Cascade was expressed and purified as described (Jore et al., 2011). Throughout purification a buffer containing 20 mM HEPES pH 7.5, 75 mM NaCl, 1 mM DTT, 2 mM EDTA was used for resuspension and washing. Protein elution was performed in the same buffer containing 4 mM desthiobiotin. The Cascade-Cas3 fusion complex was expressed and purified in the same manner, with washing steps being performed with 20 mM HEPES pH 7.5, 200 mM NaCl and 1 mM DTT, and elution in 20 mM HEPES pH 7.5, 75 mM NaCl, 1 mM DTT containing 4 mM desthiobiotin.

Electrophoretic Mobility Shift Assay

Purified Cascade or Cascade subsomplexes were mixed with pUC-λ in a buffer containing 20 mM HEPES pH 7.5, 75 mM NaCl, 1 mM DTT, 2 mM EDTA, and incubated at 37° C. for 15 minutes. Samples were run overnight on a 0.8% TAE Agarose gel and post-stained with SybR safe (Invitrogen) 1:10000 dilution in TAE for 30 minutes. Cleavage with BsmI (Fermentas) or nicking with Nt.BspQI (New England Biolabs) was performed in the HEPES reaction buffer supplemented with 5 mM $MgCl_2$.

Scanning Force Microscopy

Purified Cascade was mixed with pUC-λ (at a ratio of 7:1, 250 nM Cascade, 35 nM DNA) in a buffer containing 20 mM HEPES pH 7.5, 75 mM NaCl, 0.2 mM DTT, 0.3 mM EDTA and incubated at 37° C. for 15 minutes. Subsequently, for AFM sample preparation, the incubation mixture was diluted 10× in double distilled water and $MgCl_2$ was added at a final concentration of 1.2 mM. Deposition of the protein-DNA complexes and imaging was carried out as described before (Dame et al., (2000) Nucleic Acids Res. 28: 3504-3510).

Fluorescence Microscopy

BL21-AI cells carrying CRISPR en cas gene encoding plasmids, were grown overnight at 37° C. in Luria-Bertani broth (LB) containing ampicillin (100 μg/ml), kanamycin (50 μg/ml), streptomycin (50 μg/ml) and chloramphenicol (34 μg/ml). Overnight culture was diluted 1:100 in fresh antibiotic-containing LB, and grown for 1 hour at 37° C. Expression of cas genes and CRISPR was induced for 1 hour by adding L-arabinose to a final concentration of 0.2% and IPTG to a final concentration of 1 mM. For infection, cells were mixed with phage Lambda at a Multiplicity of Infection (MOI) of 4. Cells were applied to poly-L-lysine covered microscope slides, and analyzed using a Zeiss LSM510 confocal laser scanning microscope based on an Axiovert inverted microscope, with a 40× oil immersion objective (N.A. of 1.3) and an argon laser as the excitation source (514 nm) and detection at 530-600 nm. The pinhole was set at 203 μm for all measurements.

pUC-λ Transformation Studies

LB containing kanamycin (50 μg/ml), streptomycin (50 μg/ml) and chloramphenicol (34 μg/ml) was inoculated from an overnight pre-inoculum and grown to an $OD_{600}$ of 0.3. Expression of cas genes and CRISPR was induced for 45 minutes with 0.2% L-arabinose and 1 mM IPTG. Cells were collected by centrifugation at 4° C. and made competent by resuspension in ice cold buffer containing 100 mM $RbCl_2$, 50 mM $MnCl_2$, 30 mM potassium acetate, 10 mM $CaCl_2$ and 15% glycerol, pH 5.8. After a 3 hour incubation, cells were collected and resuspended in a buffer containing 10 mM MOPS, 10 mM RbCl, 75 mM $CaCl_2$, 15% glycerol, pH 6.8. Transformation was performed by adding 80 ng pUC-λ, followed by a 1 minute heat-shock at 42° C., and 5 minute cold-shock on ice. Next cells were grown in LB for 45 minutes at 37° C. before plating on LB-agar plates containing 0.2% L-arabinose, 1 mM IPTG, ampicillin (100 μg/ml), kanamycin (50 μg/ml), streptomycin (50 μg/ml) and chloramphenicol (34 μg/ml).

Plasmid curing was analyzed by transforming BL21-AI cells containing cas gene and CRISPR encoding plasmids with pUC-λ, while growing the cells in the presence of 0.2% glucose to suppress expression of the T7-polymerase gene. Expression of cas genes and CRISPR was induced by collecting the cells and re-suspension in LB containing 0.2% arabinose and 1 mM IPTG. Cells were plated on LB-agar containing either streptomycin, kanamycin and chloramphenicol (non-selective for pUC-λ) or ampicillin, streptomycin, kanamycin and chloramphenicol (selective for pUC-λ). After overnight growth the percentage of plasmid loss can be calculated from the ratio of colony forming units on the selective and non-selective plates.

Phage Lambda Infection Studies

Host sensitivity to phage infection was tested using a virulent phage Lambda ($\lambda_{vir}$), as in (Brouns et al (2008) Science 321, 960-964.). The sensitivity of the host to infection was calculated as the efficiency of plaquing (the plaque count ratio of a strain containing an anti-λ CRISPR to that of the strain containing a non-targeting R44 CRISPR) as described in Brouns et al (2008).

Example 1

Cascade Exclusively Binds Negatively Supercoiled Target DNA

Figure 1E:
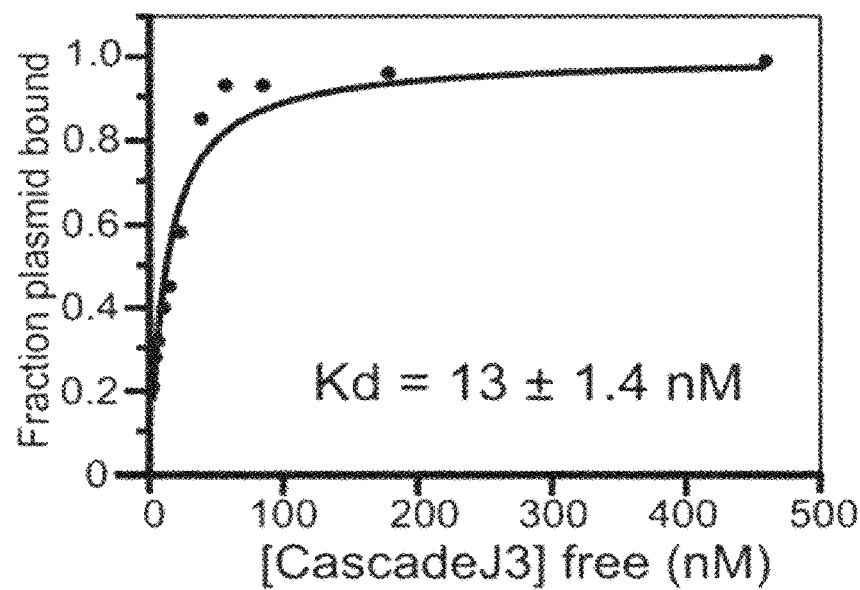
Figure 1F:
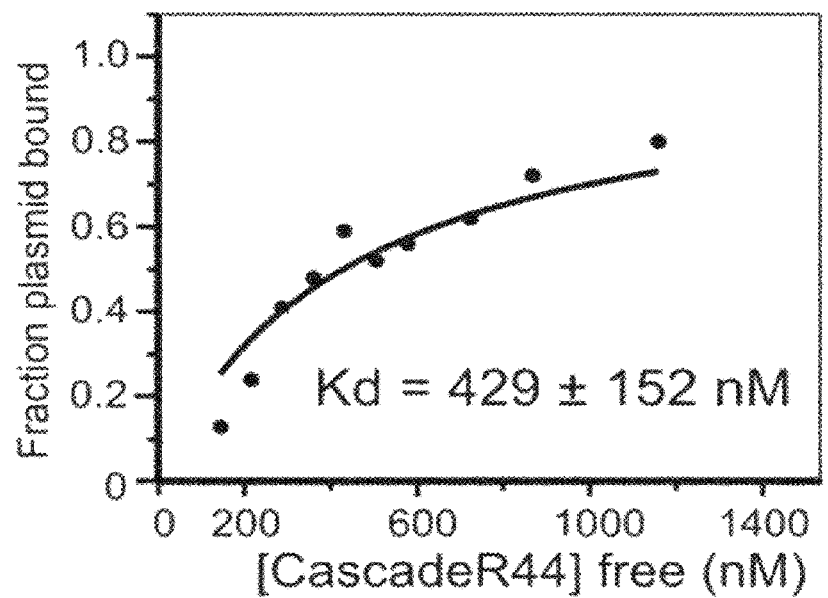

The 3 kb pUC19-derived plasmid denoted pUC-λ, contains a 350 bp DNA fragment corresponding to part of the J gene of phage λ, which is targeted by J3-Cascade (Cascade associated with crRNA containing spacer J3 (Westra et al (2010) Molecular Microbiology 77, 1380-1393). The electrophoretic mobility shift assays show that Cascade has high affinity only for negatively supercoiled (nSC) target plasmid. At a molar ratio of J3-Cascade to pUC-λ of 6:1 all nSC plasmid was bound by Cascade, (see FIG. 1A), while Cascade carrying the non-targeting crRNA R44 (R44-Cascade) displayed non-specific binding at a molar ratio of 128:1 (see FIG. 1B). The dissociation constant (Kd) of nSC pUC-λ was determined to be 13±1.4 nM for J3-Cascade (see FIG. 1E) and 429±152 nM for R44-Cascade (see FIG. 1F).

J3-Cascade was unable to bind relaxed target DNA with measurable affinity, such as nicked (see FIG. 1C) or linear pUC-λ (see FIG. 1D), showing that Cascade has high affinity for larger DNA substrates with a nSC topology.

To distinguish non-specific binding from specific binding, the BsmI restriction site located within the protospacer was used. While adding BsmI enzyme to pUC-λ gives a linear product in the presence of R44-Cascade (see FIG. 1G, lane 4), pUC-λ is protected from BsmI cleavage in the presence of J3-Cascade (see FIG. 1G, lane 7), indicating specific binding to the protospacer. This shows that Cas3 is not required for in vitro sequence specific binding of Cascade to a protospacer sequence in a nSC plasmid.

Figure 1H:
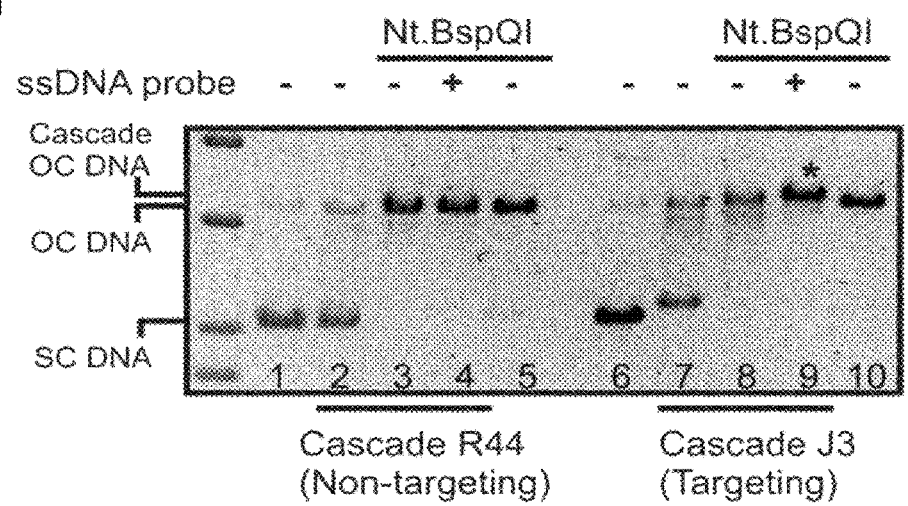
Figure 1I:
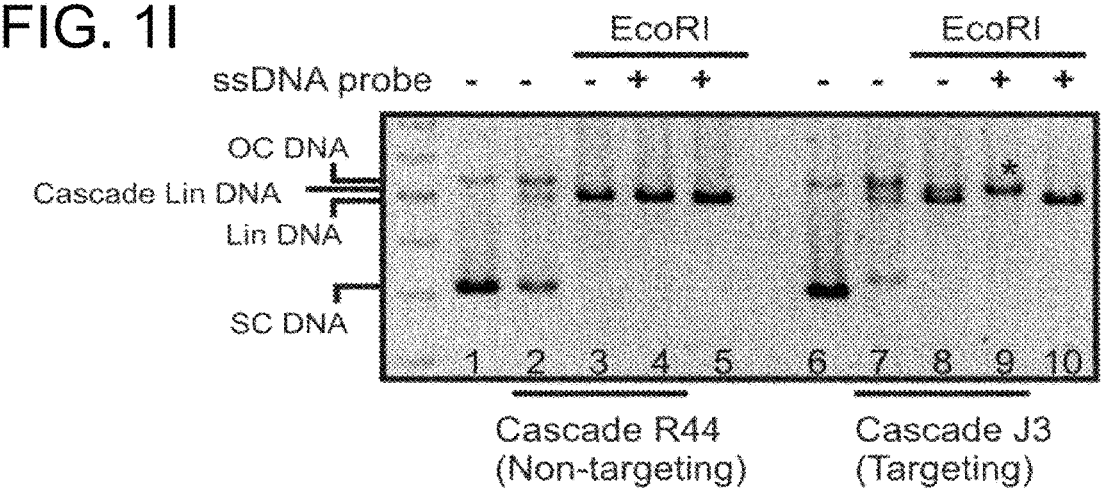

Cascade binding to nSC pUC-λ was followed by nicking with Nt.BspQI, giving rise to an OC topology. Cascade is released from the plasmid after strand nicking, as can be seen from the absence of a mobility shift (see FIG. 1H, compare lane 8 to lane 10). In contrast, Cascade remains bound to its DNA target when a ssDNA probe complementary to the displaced strand is added to the reaction before DNA nicking by Nt.BspQI (see FIG. 1H, lane 9). The probe artificially stabilizes the Cascade R-loop on relaxed target DNA. Similar observations are made when both DNA strands of pUC-λ are cleaved after Cascade binding (see FIG. 1I, lane 8 and lane 9).

Example 2

Cascade Induces Bending of Bound Target DNA

Figure 2:
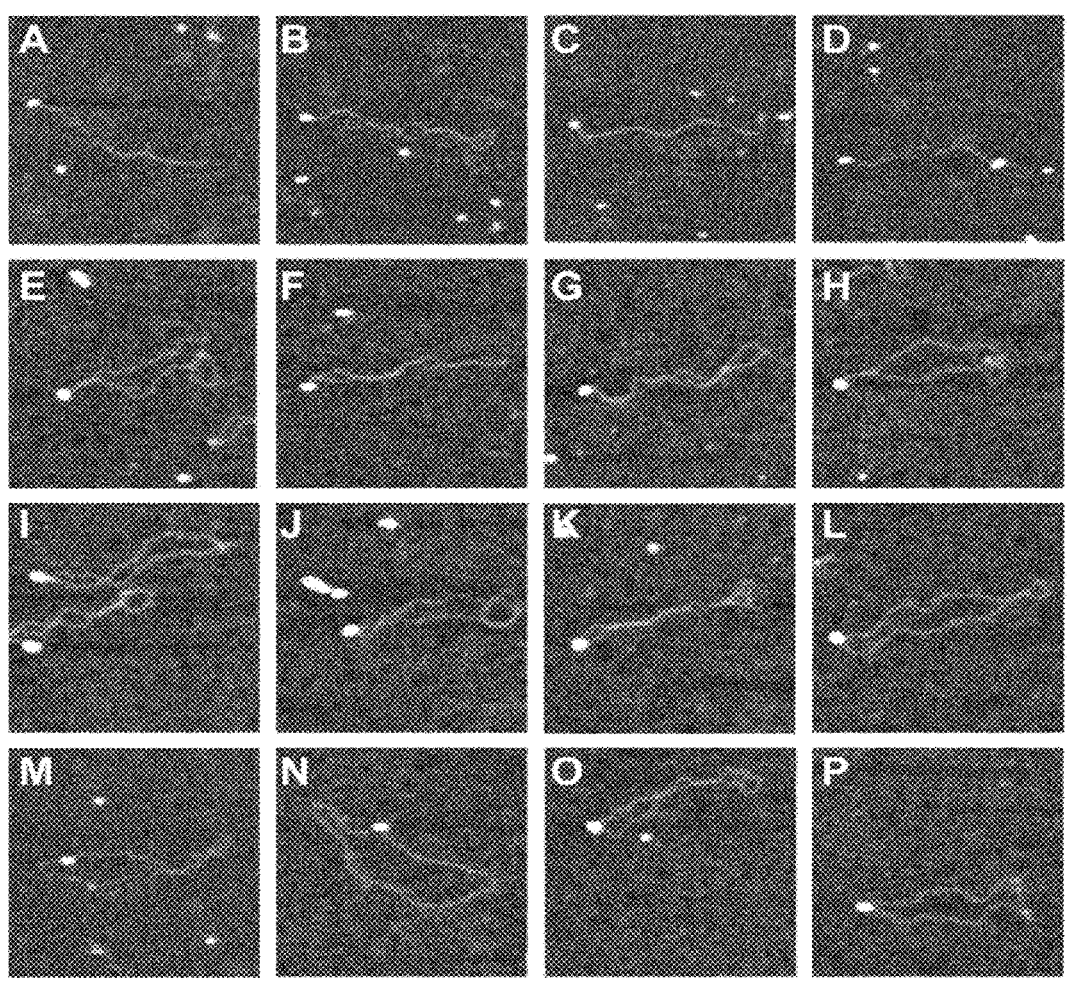

Complexes formed between purified Cascade and pUC-λ were visualized. Specific complexes containing a single bound J3-Cascade complex were formed, while unspecific R44-Cascade yields no DNA bound complexes in this assay under identical conditions. Out of 81 DNA molecules observed 76% were found to have J3-Cascade bound (see FIG. 2, panels A-P). Of these complexes in most cases Cascade was found at the apex of a loop (86%), whereas a small fraction only was found at non-apical positions (14%). These data show that Cascade binding causes bending and possibly wrapping of the DNA, probably to facilitate local melting of the DNA duplex.

Example 3

Naturally Occurring Fusions of Cas3 and Cse1: Cas3 Interacts with Cascade Upon Protospacer Recognition FIG. 10 shows sequence analysis of cas3 genes from organisms containing the Type I-E CRISPR/Cas system reveals that Cas3 and Cse1 occur as fusion proteins in *Streptomyces* sp. SPB78 (Accession Number: ZP_07272643.1), in *Streptomyces griseus* (Accession Number YP_001825054), and in *Catenulispora acidiphila* DSM 44928 (Accession Number YP_003114638).

Example 4

Bimolecular Fluorescence Complementation (BiFC) Shows how a Cse1 Fusion Protein Forming Part of Cascade Continues to Interact with Cas3

BiFC experiments were used to monitor interactions between Cas3 and Cascade in vivo before and after phage λ infection. BiFC experiments rely on the capacity of the non-fluorescent halves of a fluorescent protein, e.g., Yellow Fluorescent Protein (YFP) to refold and to form a fluorescent molecule when the two halves occur in close proximity. As such, it provides a tool to reveal protein-protein interactions, since the efficiency of refolding is greatly enhanced if the local concentrations are high, e.g., when the two halves of the fluorescent protein are fused to interaction partners. Cse1 was fused at the C-terminus with the N-terminal 155 amino acids of Venus (Cse1-N155Venus), an improved version of YFP (Nagai et al (2002) Nature Biotechnology 20, 87-90). Cas3 was C-terminally fused to the C-terminal 85 amino acids of Venus (Cas3-C85Venus).

BiFC analysis reveals that Cascade does not interact with Cas3 in the absence of invading DNA (FIG. 3A, FIG. 3B, FIG. 3C, FIG. 3P and FIG. 8). Upon infection with phage λ, however, cells expressing CascadeΔCse1, Cse1-N155Venus and Cas3-C85Venus are fluorescent if they co-express the anti-λ CRISPR 7Tm (FIG. 3D, FIG. 3E, FIG. 3F, FIG. 3P and FIG. 8). When they co-express a non-targeting CRISPR R44 (FIG. 3G, FIG. 3H, FIG. 3I, FIG. 3P and FIG. 8), the cells remain non-fluorescent. This shows that Cascade and Cas3 specifically interact during infection upon protospacer recognition and that Cse1 and Cas3 are in close proximity of each other in the Cascade-Cas3 binary effector complex.

These results also show quite clearly that a fusion of Cse1 with an heterologous protein does not disrupt the ribonucleoprotein formation of Cascade and crRNA, nor does it disrupt the interaction of Cascade and Cas3 with the target phage DNA, even when the Cas3 itself is also a fusion protein.

Example 5

Figure 5A:
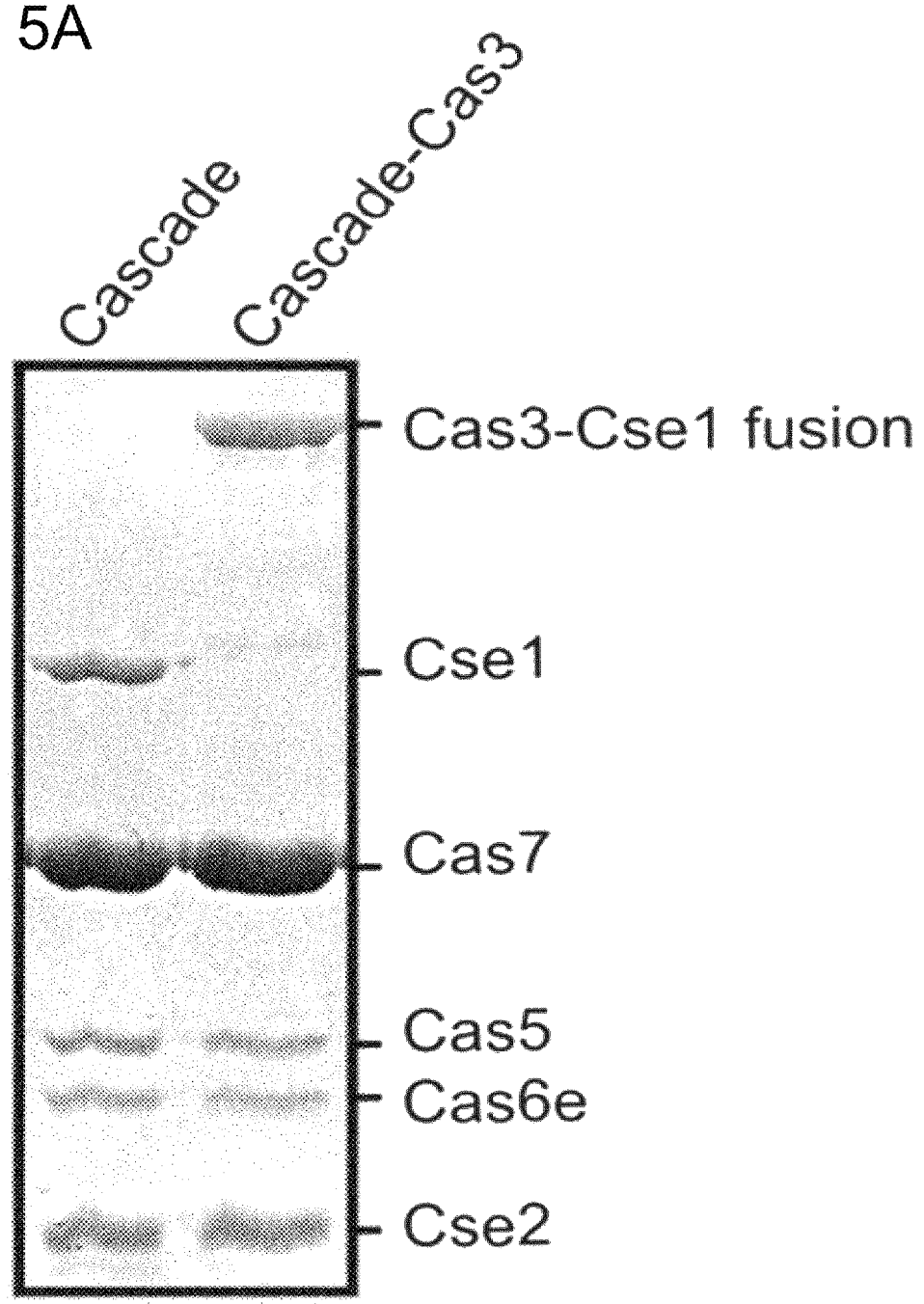
Figure 5B:
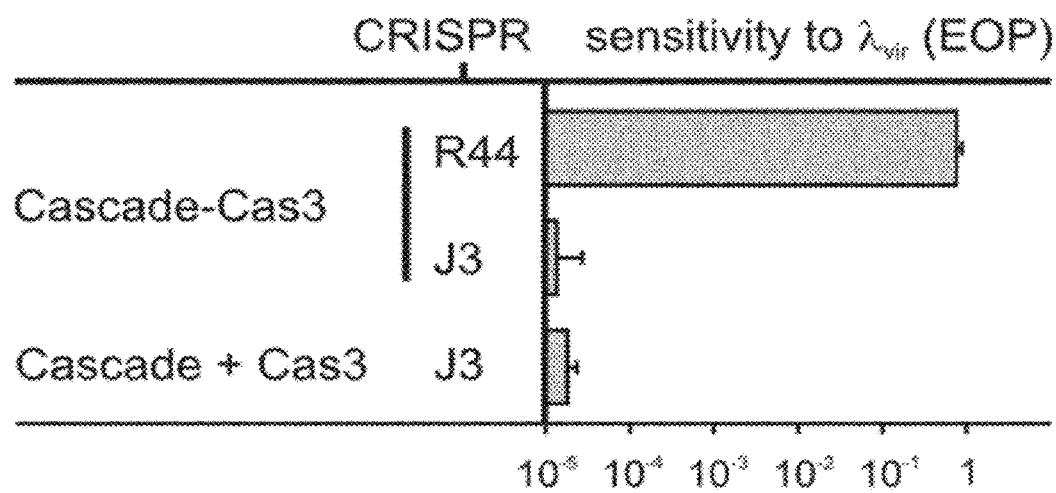

Preparing a Designed Cas3-Cse1 Fusion Gives a Protein with In Vivo Functional Activity Providing in vitro evidence for Cas3 DNA cleavage activity required purified and active Cas3. Despite various solubilization strategies, Cas3 overproduced (Howard et al (2011) Biochem. J. 439, 85-95) in *E. coli* BL21 is mainly present in inactive aggregates and inclusion bodies. Cas3 was therefore produced as a Cas3-Cse1 fusion protein, containing a linker identical to that of the Cas3-Cse1 fusion protein in *S. griseus* (see FIG. 10). When co-expressed with CascadeΔCse1 and CRISPR J3, the fusion-complex was soluble and was obtained in high purity with the same apparent stoichiometry as Cascade (FIG. 5A). When functionality of this complex was tested for providing resistance against phage λ infection, the efficiency of plaquing (eop) on cells expressing the fusion-complex J3-Cascade-Cas3 was identical as on cells expressing the separate proteins (FIG. 5B).

Since the J3-Cascade-Cas3 fusion-complex was functional in vivo, in vitro DNA cleavage assays were carried out using this complex. When J3-Cascade-Cas3 was incubated with pUC-λ in the absence of divalent metals, plasmid binding was observed at molar ratios similar to those observed for Cascade (FIG. 5C), while a-specific binding to a non-target plasmid (pUC-p7, a pUC19 derived plasmid of the same size as pUC-λ, but lacking a protospacer) occurred only at high molar ratios (FIG. 5D), indicating that a-specific DNA binding of the complex is also similar to that of Cascade alone.

Interestingly, the J3-Cascade-Cas3 fusion complex displays magnesium dependent endonuclease activity on nSC target plasmids. In the presence of 10 mM $Mg^{2+}$ J3-Cascade-Cas3 nicks nSC pUC-λ (FIG. 5E, lane 3-7), but no cleavage is observed for substrates that do not contain the target sequence (FIG. 5E, lane 9-13), or that have a relaxed topology. No shift of the resulting OC band is observed, in line with previous observations that Cascade dissociates spontaneously after cleavage, without requiring ATP-dependent Cas3 helicase activity. Instead, the helicase activity of Cas3 appears to be involved in exonucleolytic plasmid degradation. When both magnesium and ATP are added to the reaction, full plasmid degradation occurred (FIG. 5H).

The inventors have found that Cascade alone is unable to bind protospacers on relaxed DNA. In contrast, the inventors have found that Cascade efficiently locates targets in negatively supercoiled DNA, and subsequently recruits Cas3 via the Cse1 subunit. Endonucleolytic cleavage by the Cas3 HD-nuclease domain causes spontaneous release of Cascade from the DNA through the loss of supercoiling, remobilizing Cascade to locate new targets. The target is then progressively unwound and cleaved by the joint ATP-dependent helicase activity and HD-nuclease activity of Cas3, leading to complete target DNA degradation and neutralization of the invader.

Figure 6:
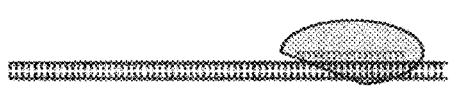
FIG. 6 is a schematic diagram showing a model of the CRISPR-interference type I pathway in *E. coli*.
Figure 6:
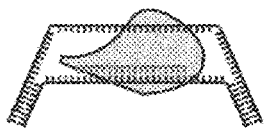
Figure 6:
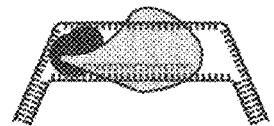
Figure 6:
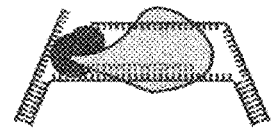
Figure 6:
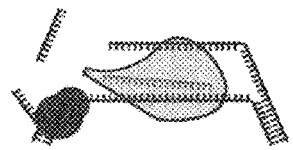
Figure 6:
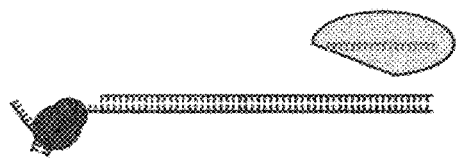
Figure 6:
Figure 7:
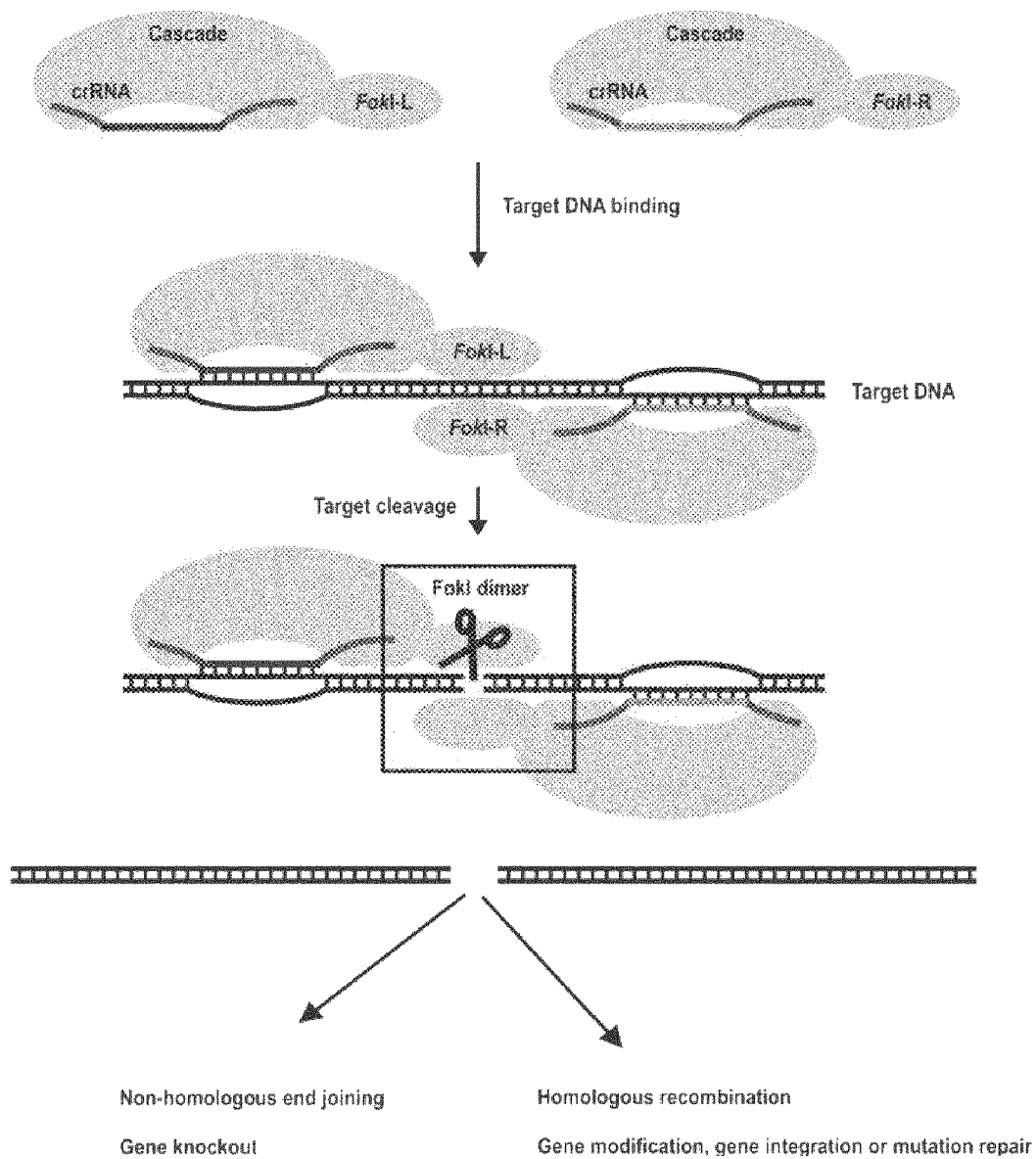
FIG. 7 is a schematic diagram showing how a Cascade-FokI fusion embodiment of the invention is used to create FokI dimers which cuts dsDNA to produce blunt ends as part of a process of non-homologous end joining or homologous recombination.

Referring to FIG. 6 and without wishing to be bound to any particular theory, a mechanism of operation for the CRISPR-interference type I pathway in *E. coli* may involve (1) First, Cascade carrying a crRNA scans the nSC plasmid DNA for a protospacer, with adjacent PAM. Whether during this stage strand separation occurs is unknown. (2) Sequence specific protospacer binding is achieved through basepairing between the crRNA and the complementary strand of the DNA, forming an R-loop. Upon binding, Cascade induces bending of the DNA. (3) The Cse1 subunit of Cascade recruits Cas3 upon DNA binding. This may be achieved by Cascade conformational changes that take place upon nucleic acid binding. (4) The HD-domain (darker part) of Cas3 catalyzes $Mg^{2+}$-dependent nicking of the displaced strand of the R-loop, thereby altering the topology of the target plasmid from nSC to relaxed OC. (5a and 5b) The plasmid relaxation causes spontaneous dissociation of Cascade. Meanwhile Cas3 displays ATP-dependent exonuclease activity on the target plasmid, requiring the helicase domain for target dsDNA unwinding and the HD-nuclease domain for successive cleavage activity. (6) Cas3 degrades the entire plasmid in an ATP-dependent manner as it processively moves along, unwinds and cleaves the target dsDNA.

Example 6

Preparation of Artificial Cas-Strep Tag Fusion Proteins and Assembly of Cascade Complexes Cascade complexes are produced and purified as described in Brouns et al (2008) Science 321: 960-4 (2008), using the expression plasmids listed in Supplementary Table 3 of Jore et al (2011) Nature Structural & Molecular Biology 18: 529-537. Cascade is routinely purified with an N-terminal Strep-tag II fused to CasB (or CasC in CasCDE). Size exclusion chromatography (Superdex 200 HR 10/30 (GE)) is performed using 20 mM Tris-HCl (pH 8.0), 0.1 M NaCl, 1 mM dithiotreitol. Cascade preparations (~0.3 mg) are incubated with DNase I (Invitrogen) in the presence of 2.5 mM $MgCl_2$ for 15 min at 37° C. prior to size exclusion analysis. Co-purified nucleic acids are isolated by extraction using an equal volume of phenol:chloroform:isoamylalcohol (25:24:1) pH 8.0 (Fluka), and incubated with either DNase I (Invitrogen) supplemented with 2.5 mM $MgCl_2$ or RNase A (Fermentas) for 10 min at 37° C. Cas subunit proteins fused to the amino acid sequence of Strep-Tag are produced.

Plaque assays showing the biological activity of the Strep-Tag Cascade subunits are performed using bacteriophage Lambda and the efficiency of plaquing (EOP) was calculated as described in Brouns et al (2008).

For purification of crRNA, samples are analyzed by ion-pair reversed-phased-HPLC on an Agilent 1100 HPLC with $UV_{260\ nm}$. detector (Agilent) using a DNAsep column 50 mm×4.6 mm I. D. (Transgenomic, San Jose, Calif.). The chromatographic analysis is performed using the following buffer conditions: A) 0.1 M triethylammonium acetate (TEAA) (pH 7.0) (Fluka); B) buffer A with 25% LC MS grade acetonitrile (v/v) (Fisher). crRNA is obtained by injecting purified intact Cascade at 75° C. using a linear gradient starting at 15% buffer B and extending to 60% B in 12.5 min, followed by a linear extension to 100% B over 2 min at a flow rate of 1.0 ml/min. Hydrolysis of the cyclic phosphate terminus was performed by incubating the HPLC-purified crRNA in a final concentration of 0.1 M HCl at 4° C. for 1 hour. The samples are concentrated to 5-10 µl on a vacuum concentrator (Eppendorf) prior to ESI-MS analysis.

Electrospray Ionization Mass spectrometry analysis of crRNA is performed in negative mode using an UHR-TOF mass spectrometer (maXis) or an HCT Ultra PTM Discovery instrument (both Bruker Daltonics), coupled to an online capillary liquid chromatography system (Ultimate 3000, Dionex, UK). RNA separations are performed using a monolithic (PS-DVB) capillary column (200 µm×50 mm I.D., Dionex, UK). The chromatography is performed using the following buffer conditions: C) 0.4 M 1,1,1,3,3,3,-Hexafluoro-2-propanol (HFIP, Sigma-Aldrich) adjusted with triethylamine (TEA) to pH 7.0 and 0.1 mM TEAA, and D) buffer C with 50% methanol (v/v) (Fisher). RNA analysis is performed at 50° C. with 20% buffer D, extending to 40% D in 5 min followed by a linear extension to 60% D over 8 min at a flow rate of 2 µl/min.

Cascade protein is analyzed by native mass spectrometry in 0.15 M ammonium acetate (pH 8.0) at a protein concentration of 5 µM. The protein preparation is obtained by five sequential concentration and dilution steps at 4° C. using a centrifugal filter with a cut-off of 10 kDa (Millipore). Proteins are sprayed from borosilicate glass capillaries and analyzed on a LCT electrospray time-of-flight or modified quadrupole time-of-flight instruments (both Waters, UK) adjusted for optimal performance in high mass detection (see Tahallah N et al (2001) Rapid Commun Mass Spectrom 15: 596-601 (2001) and van den Heuvel, R. H. et al. Anal Chem 78: 7473-83 (2006). Exact mass measurements of the individual Cas proteins were acquired under denaturing conditions (50% acetonitrile, 50% MQ, 0.1% formic acid). Sub-complexes in solution were generated by the addition of 2-propanol to the spray solution to a final concentration of 5% (v/v). Instrument settings were as follows; needle voltage ~1.2 kV, cone voltage ~175 V, source pressure 9 mbar. Xenon was used as the collision gas for tandem mass spectrometric analysis at a pressure of 1.5 $10^{-2}$ mbar. The collision voltage varied between 10-200 V.

Electrophoretic mobility shift assays (EMSA) are used to demonstrate the functional activity of Cascade complexes for target nucleic acids. EMSA is performed by incubating Cascade, CasBCDE or CasCDE with 1 nM labelled nucleic acid in 50 mM Tris-Cl pH 7.5, 100 mM NaCl. Salmon sperm DNA (Invitrogen) is used as competitor. EMSA reactions are incubated at 37° C. for 20-30 min prior to electrophoresis on 5% polyacrylamide gels. The gels are dried and analyzed using phosphor storage screens and a PMI phosphor imager (Bio-Rad). Target DNA binding and cleavage activity of Cascade is tested in the presence of 1-10 mM Ca, Mg or Mn-ions.

DNA targets are gel-purified long oligonucleotides (Isogen Life Sciences or Biolegio), listed in Supplementary Table 3 of Jore et al (2011). The oligonucleotides are end-labeled using $\gamma^{32}$P-ATP (PerkinElmer) and T4 kinase (Fermentas). Double-stranded DNA targets are prepared by annealing complementary oligonucleotides and digesting remaining ssDNA with Exonuclease I (Fermentas). Labelled RNA targets are in vitro transcribed using T7 Maxiscript or T7 Mega Shortscript kits (Ambion) with $\alpha^{32}$P-CTP (PerkinElmer) and removing template by DNase I (Fermentas) digestion. Double stranded RNA targets are prepared by annealing complementary RNAs and digesting surplus ssRNA with RNase T1 (Fermentas), followed by phenol extraction.

Plasmid mobility shift assays are performed using plasmid pWUR613 containing the R44 protospacer. The fragment containing the protospacer is PCR-amplified from bacteriophage P7 genomic DNA using primers BG3297 and BG 3298 (see Supplementary Table 3 of Jore et al (2011). Plasmid (0.4 µg) and Cascade were mixed in a 1:10 molar ratio in a buffer containing 5 mM Tris-HCl (pH 7.5) and 20 mM NaCl and incubated at 37° C. for 30 minutes. Cascade proteins were then removed by proteinase K treatment (Fluka) (0.15 U, 15 min, 37° C.) followed by phenol/chloroform extraction. RNA-DNA complexes were then treated with RNaseH (Promega) (2 U, 1 h, 37° C.).

Strep-Tag-Cas protein subunit fusions which form Cascade protein complexes or active sub-complexes with the RNA component (equivalent to a crRNA), have the expected biological and functional activity of scanning and specific attachment and cleavage of nucleic acid targets. Fusions of the Cas subunits with the amino acid chains of fluorescent dyes also form Cascade complexes and sub-complexes with the RNA component (equivalent to crRNA) which retains biological and functional activity and allows visualisation of the location of a target nucleic acid sequence in ds DNA for example.

Example 7

A Cascade-Nuclease Pair and Test of Nuclease Activity In Vitro

Six mutations designated "Sharkey" have been introduced by random mutagenesis and screening to improve nuclease activity and stability of the non-specific nuclease domain from *Flavobacterium okeanokoites* restriction enzyme FokI (see Guo, J., et al. (2010) J. Mol. Biol. 400: 96-107). Other mutations have been introduced that reduce off-target cleavage activity. This is achieved by engineering electrostatic interactions at the FokI dimer interface of a ZFN pair, creating one FokI variant with a positively charged interface (KKR, E490K, I538K, H537R) and another with a negatively charged interface (ELD, Q486E, I499L, N496D) (see Doyon, Y., et al. (2011) Nature Methods 8: 74-9). Each of these variants is catalytically inactive as a homodimer, thereby reducing the frequency of off-target cleavage.

Cascade-Nuclease Design

We translationally fused improved FokI nucleases to the N-terminus of Cse1 to generate variants of Cse1 being FokI$^{KKR}$-Cse1 and FokI$^{ELD}$-Cse1, respectively. These two variants are co-expressed with Cascade subunits (Cse2, Cas7, Cas5 and Cas6e), and one of two distinct CRISPR plasmids with uniform spacers. This loads the Cascade$^{KKR}$ complex with uniform P7-crRNA, and the Cascade$^{ELD}$ complex with uniform M13 g8-crRNA. These complexes are purified using the N-terminally StrepII-tagged Cse2 as described in Jore, M. M., et al., (2011) Nat. Struct. Mol. Biol. 18(5): 529-536. Furthermore an additional purification step can be carried out using an N-terminally HIS-tagged FokI, to ensure purifying full length and intact Cascade-nuclease fusion complexes.

The nucleotide and amino acid sequences of the fusion proteins used in this example were as follows:

>nucleotide sequence of FokI-(Sharkey-ELD)-Cse1 [SEQ ID NO: 18]

```
ATGGCTCAACTGGTTAAAAGCGAACTGGAAGAGAAAAAAGTGAACTGCGCCAC

AAACTGAAATATGTGCCGCATGAATATATCGAGCTGATTGAAATTGCACGTAATC

CGACCCAGGATCGTATTCTGGAAATGAAAGTGATGGAATTTTTTATGAAAGTGTA
```

-continued

```
CGGCTATCGCGGTGAACATCTGGGTGGTAGCCGTAAACCGGATGGTGCAATTTAT

ACCGTTGGTAGCCCGATTGATTATGGTGTTATTGTTGATACCAAAGCCTATAGCG

GTGGTTATAATCTGCCGATTGGTCAGGCAGATGAAATGGAACGTTATGTGGAAG

AAAATCAGACCCGTGATAAACATCTGAATCCGAATGAATGGTGGAAAGTTTATC

CGAGCAGCGTTACCGAGTTTAAATTCCTGTTTGTTAGCGGTCACTTCAAAGGCAA

CTATAAAGCACAGCTGACCCGTCTGAATCATATTACCAATTGTAATGGTGCAGTT

CTGAGCGTTGAAGAACTGCTGATTGGTGGTGAAATGATTAAAGCAGGCACCCTG

ACCCTGGAAGAAGTTCGTCGCAAATTTAACAATGGCGAAATCAACTTTGCGGAT

CCCACCAACCGCGCGAAAGGCCTGGAAGCGGTGAGCGTGGCGAGCatgaatttgct tattgataactggattcctgtacgcccgcgaaacgggggaaagtccaaatcataaatctgcaatcgctatactgcagtagagatcagt ggcgattaagtttgccccgtgacgatatggaactggccgctttagcactgctggtttgcattgggcaaattatcgccccggcaaaagatg acgttgaatttcgacatcgcataatgaatccgctcactgaagatgagtttcaacaactcatcgcgccgtggatagatatgttctaccttaat cacgcagaacatcccttatgcagaccaaaggtgtcaaagcaaatgatgtgactccaatggaaaaactgttggctggggtaagcggcg cgacgaattgtgcatttgtcaatcaaccggggcagggtgaagcattatgtggtggatgcactgcgattgcgttattcaaccaggcgaat caggcaccaggttttggtggtggttttaaaagcggtttacgtggaggaacacctgtaacaacgttcgtacgtgggatcgatcttcgttcaa cggtgttactcaatgtcctcacattacctcgtcttcaaaaacaatttcctaatgaatcacatacggaaaaccaacctacctggattaaacct atcaagtccaatgagtctatacctgatcgtcaattgggtttgtccgtggtctattctggcaaccagcgcatattgaattatgcgatcccatt gggattggtaaatgttcttgctgtggacaggaaagcaatttgcgttataccggttttcttaaggaaaaatttaccttacagttaatgggctat ggccccatccgcattccccttgtctggtaacagtcaagaaagggggaggttgaggaaaaatttcttgctttcaccacctccgcaccatcat ggacacaaatcagccgagttgtggtagataagattattcaaaatgaaaatggaaatcgcgtggcggcggttgtgaatcaattcagaaat attgcgccgcaaagtcctcttgaattgattatgggggatatcgtaataatcaagcatctattcttgaacgcgtcatgatgtgttgatgttt aatcaggggtggcaacaatacggcaatgtgataaacgaaatagtgactgttggtttgggatataaaacagccttacgcaaggcgttata tacctttgcagaagggtttaaaaataaagacttcaaaggggccggagtctctgttcatgagactgcagaaaggcatttctatcgacagag tgaattattaattcccgatgtactggcgaatgttaatttttcccaggctgatgaggtaatagctgatttacgagacaaacttcatcaattgtgt gaaatgctatttaatcaatctgtagctccctatgcacatcatcctaaattaataagcacattagcgcttgcccgcgccacgctatacaaaca tttacgggagttaaaaccgcaaggagggccatcaaatggctga
```

\>protein sequence of FokI-(Sharkey-ELD)-Cse1

[SEQ ID NO: 19]

MAQLVKSELEEKKSELRHKLKYVPHEYIELIEIARNPTQDRILEMKVMEFFMKVYGY

RGEHLGGSRKPDGAIYTVGSPIDYGVIVDTKAYSGGYNLPIGQADEMERYVEENQTR

DKHLNPNEWWKVYPSSVTEFKFLFVSGHFKGNYKAQLTRLNHITNCNGAVLSVEEL

LIGGEMIKAGTLTLEEVRRKFNNGEINFADPTNRAKGLEAVSVASMNLLIDNWIPVRP

RNGGKVQIINLQSLYCSRDQWRLSLPRDDMELAALALLVCIGQIIAPAKDDVEFRHRI

MNPLTEDEFQQLIAPWIDMFYLNHAEHPFMQTKGVKANDVTPMEKLLAGVSGATN

CAFVNQPGQGEALCGGCTAIALFNQANQAPGFGGGFKSGLRGGTPVTTFVRGIDLRS

TVLLNVLTLPRLQKQFPNESHTENQPTWIKPIKSNESIPASSIGFVRGLFWQPAHIELC

DPIGIGKCSCCGQESNLRYTGFLKEKFTFTVNGLWPHPHSPCLVTVKKGEVEEKFLAF

TTSAPSWTQISRVVVDKIIQNENGNRVAAVVNQFRNIAPQSPLELIMGGYRNNQASIL

ERRHDVLMFNQGWQQYGNVINEIVTVGLGYKTALRKALYTFAEGFKNKDFKGAGV

SVHETAERHFYRQSELLIPDVLANVNFSQADEVIADLRDKLHQLCEMLFNQSVAPYA

HHPKLISTLALARATLYKHLRELKPQGGPSNG*

>nucleotide sequence of FokI-(Sharkey-KKR)-Cse1 [SEQ ID NO: 20]

ATGGCTCAACTGGTTAAAAGCGAACTGGAAGAGAAAAAAAGTGAACTGCGCCAC

AAACTGAAATATGTGCCGCATGAATATATCGAGCTGATTGAAATTGCACGTAATC

CGACCCAGGATCGTATTCTGGAAATGAAAGTGATGGAATTTTTTATGAAAGTGTA

CGGCTATCGCGGTGAACATCTGGGTGGTAGCCGTAAACCGGATGGTGCAATTTAT

ACCGTTGGTAGCCCGATTGATTATGGTGTTATTGTTGATACCAAAGCCTATAGCG

GTGGTTATAATCTGCCGATTGGTCAGGCAGATGAAATGCAGCGTTATGTGAAAG

AAAATCAGACCCGCAACAAACATATTAACCCGAATGAATGGTGGAAAGTTTATC

CGAGCAGCGTTACCGAGTTTAAATTCCTGTTTGTTAGCGGTCACTTCAAAGGCAA

CTATAAAGCACAGCTGACCCGTCTGAATCGTAAAACCAATTGTAATGGTGCAGTT

CTGAGCGTTGAAGAACTGCTGATTGGTGGTGAAATGATTAAAGCAGGCACCCTG

ACCCTGGAAGAAGTTCGTCGCAAATTTAACAATGGCGAAATCAACTTTGCGGAT

CCCACCAACCGCGCGAAAGGCCTGGAAGCGGTGAGCGTGGCGAGCatgaatttgct tattgataactggattcctgtacgcccgcgaaacgggggaaagtccaaatcataaatctgcaatcgctatactgcagtagagatcagt ggcgattaagtttgccccgtgacgatatggaactggccgctttagcactgctggtttgcattgggcaaattatcgccccggcaaaagatg acgttgaatttcgacatcgcataatgaatccgctcactgaagatgagtttcaacaactcatcgcgccgtggatagatatgttctaccttaat cacgcagaacatcccttatgcagaccaaaggtgtcaaagcaaatgatgtgactccaatggaaaaactgttggctggggtaagcggcg cgacgaattgtgcatttgtcaatcaaccggggcagggtgaagcattatgtggtggatgcactgcgattgcgttattcaaccaggcgaat caggcaccaggttttggtggtggttttaaaagcggtttacgtggaggaacacctgtaacaacgttcgtacgtgggatcgatcttcgttcaa cggtgttactcaatgtcctcacattacctcgtcttcaaaaacaatttcctaatgaatcacatacggaaaaccaacctacctggattaaacct atcaagtccaatgagtctataccgcttcgtcaattgggtttgtccgtggtctattctggcaaccagcgcatattgaattatgcgatcccatt gggattggtaaatgttcttgctgtggacaggaaagcaatttgcgttataccggttttcttaaggaaaaatttacctttacagttaatgggctat ggccccatccgcattccccttgtctggtaacagtcaagaaaaggggaggttgaggaaaaatttcttgctttcaccacctccgcaccatcat ggacacaaatcagccgagttgtggtagataagattattcaaaatgaaaatggaaatcgcgtggcggcggttgtgaatcaattcagaaat attgcgccgcaaagtcctcttgaattgattatgggggatatcgtaataatcaagcatctattcttgaacggcgtcatgatgtgttgatgttt aatcaggggtggcaacaatacggcaatgtgataaacgaaatagtgactgttggtttgggatataaaacagccttacgcaaggcgttata taccttttgcagaagggtttaaaaataaagacttcaaaggggccggagtctctgttcatgagactgcagaaaggcatttctatcgacagag tgaattattaattcccgatgtactggcgaatgttaattttcccaggctgatgaggtaatagctgatttacgagacaaacttcatcaattgtgt gaaatgctatttaatcaatctgtagctccctatgcacatcatcctaaattaataagcacattagcgcttgcccgcgccacgctatacaaaca tttacgggagttaaaaccgcaaggagggccatcaaatggctga >protein sequence of FokI-(Sharkey-KKR)-Cse1 [SEQ ID NO: 21]

MAQLVKSELEEKKSELRHKLKYVPHEYIELIEIARNPTQDRILEMKVMEFFMKVYGY

RGEHLGGSRKPDGAIYTVGSPIDYGVIVDTKAYSGGYNLPIGQADEMQRYVKENQT

RNKHINPNEWWKVYPSSVTEFKFLFVSGHFKGNYKAQLTRLNRKTNCNGAVLSVEE

LLIGGEMIKAGTLTLEEVRRKFNNGEINFADPTNRAKGLEAVSVASMNLLIDNWIPV

RPRNGGKVQIINLQSLYCSRDQWRLSLPRDDMELAALALLVCIGQIIAPAKDDVEFR

HRIMNPLTEDEFQQLIAPWIDMFYLNHAEHPFMQTKGVKANDVTPMEKLLAGVSGA

TNCAFVNQPGQGEALCGGCTAIALFNQANQAPGFGGGFKSGLRGGTPVTTFVRGIDL

RSTVLLNVLTLPRLQKQFPNESHTENQPTWIKPIKSNESIPASSIGFVRGLFWQPAHIEL

CDPIGIGKCSCCGQESNLRYTGFLKEKFTFTVNGLWPHPHSPCLVTVKKGEVEEKFL

-continued

AFTTSAPSWTQISRVVVDKIIQNENGNRVAAVVNQFRNIAPQSPLELIMGGYRNNQA

SILERRHDVLMFNQGWQQYGNVINEIVTVGLGYKTALRKALYTFAEGFKNKDFKGA

GVSVHETAERHFYRQSELLIPDVLANVNFSQADEVIADLRDKLHQLCEMLFNQSVAP

YAHHPKLISTLALARATLYKHLRELKPQGGPSNG*

>nucleotide sequence of His$_6$-Dual-monopartite NLS SV40-FokI-(Sharkey-KKR)-Cse1 ("His$_6$" disclosed as SEQ ID NO: 48)

[SEQ ID NO: 22]

ATGcatcaccatcatcaccac*CCGAAAAAAAGCGCAAAGTGGATCCGAAGAAAAAACGTAAAG*

*TTGAAGATCCGAAAGACATGGCTCAACTGGTTAAAAGCGAACTGGAAGAGAAAA*

*AAAGTGAACTGCGCCACAAACTGAAATATGTGCCGCATGAATATATCGAGCTGA*

*TTGAAATTGCACGTAATCCGACCCAGGATCGTATTCTGGAAATGAAAGTGATGG*

*AATTTTTTATGAAAGTGTACGGCTATCGCGGTGAACATCTGGGTGGTAGCCGTAA*

*ACCGGATGGTGCAATTTATACCGTTGGTAGCCCGATTGATTATGGTGTTATTGTT*

*GATACCAAAGCCTATAGCGGTGGTTATAATCTGCCGATTGGTCAGGCAGATGAA*

*ATGCAGCGTTATGTGAAAGAAAATCAGACCCGCAACAAACATATTAACCCGAAT*

*GAATGGTGGAAAGTTTATCCGAGCAGCGTTACCGAGTTTAAATTCCTGTTTGTTA*

*GCGGTCACTTCAAAGGCAACTATAAAGCACAGCTGACCCGTCTGAATCGTAAAA*

*CCAATTGTAATGGTGCAGTTCTGAGCGTTGAAGAACTGCTGATTGGTGGTGAAAT*

*GATTAAAGCAGGCACCCTGACCCTGGAAGAAGTTCGTCGCAAATTTAACAATGG*

*CGAAATCAACTTTGC*GGATCCCACCAACCGCGCGAAAGGCCTGGAAGCGGTG*

*AGCGTGGCGAGC*atgaatttgcttattgataactggattcctgtacgcccgcgaaacggggggaaagtccaaatcataaat ctgcaatcgctatactgcagtagagatcagtggcgattaagtttgccccgtgacgatatggaactggccgctttagcactgctggtttgc attgggcaaattatcgccccggcaaaagatgacgttgaatttcgacatcgcataatgaatccgctcactgaagatgagtttcaacaactc atcgcgccgtggatagatatgttctaccttaatcacgcagaacatccctttatgcagaccaaaggtgtcaaagcaaatgatgtgactcca atggaaaaactgttggctggggtaageggcgcgacgaattgtgcatttgtcaatcaaccggggcagggtgaagcattatgtggtggat gcactgcgattgcgttattcaaccaggcgaatcaggcaccaggttttggtggtggttttaaaagcggtttacgtggaggaacacctgtaa caacgttcgtacgtgggatcgatcttcgttcaacggtgttactcaatgtcctcacattacctcgtcttcaaaaacaatttcctaatgaatcac atacggaaaaccaacctacctggattaaacctatcaagtccaatgagtctatacctgcttcgtcaattgggtttgtccgtggtctattctgg caaccagcgcatattgaattatgcgatcccattgggattggtaaatgttcttgctgtggacaggaaagcaatttgcgttataccggttttctt aaggaaaaatttaccttttacagttaatgggctatggccccatccgcattcccttgtctggtaacagtcaagaaaggggaggttgaggaa aaatttcttgctttcaccacctccgcaccatcatggacacaaatcagccgagttgtggtagataagattattcaaaatgaaaatggaaatc gcgtggcggcggttgtgaatcaattcagaaatattgcgccgcaaagtcctcttgaattgattatgggggatatcgtaataatcaagcat ctattcttgaacggcgtcatgatgtgttgatgttttaatcaggggtggcaacaatacggcaatgtgataaacgaaatagtgactgttggtttg ggatataaaacagccttacgcaaggcgttatataccttttgcagaagggtttaaaaataaagacttcaaaggggccggagtctctgttcat gagactgcagaaaggcatttctatcgacagagtgaattattaattcccgatgtactggcgaatgttaattttcccaggctgatgaggtaat agctgatttacgagacaaacttcatcaattgtgtgaaatgctatttaatcaatctgtagctccctatgcacatcatcctaaattaataagcaca ttagcgcttgcccgcgccacgctatacaaacatttacgggagttaaaaccgcaaggaggggccatcaaatggctga >protein sequence of His$_6$-Dual-monopartite NLS SV40-FokI-(Sharkey-KKR)-Cse1 ("His$_6$" disclosed as SEQ ID NO: 48)

[SEQ ID NO: 23]

MHHHHHHPKKKRKVDPKKKRKVEDPKDMAQLVKSELEEKKSELRHKLKYVPHEYI

ELIEIARNPTQDRILEMKVMEFFMKVYGYRGEHLGGSRKPDGAIYTVGSPIDYGVIVD

TKAYSGGYNLPIGQADEMQRYVKENQTRNKHINPNEWWKVYPSSVTEFKFLFVSGH

FKGNYKAQLTRLNRKTNCNGAVLSVEELLIGGEMIKAGTLTLEEVRRKFNNGEINFA

DPTNRAKGLEAVSVASMNLLIDNWIPVRPRNGGKVQIINLQSLYCSRDQWRLSLPRD

DMELAALALLVCIGQIIAPAKDDVEFRHRIMNPLTEDEFQQLIAPWIDMFYLNHAEHP

FMQTKGVKANDVTPMEKLLAGVSGATNCAFVNQPGQGEALCGGCTAIALFNQANQ

APGFGGGFKSGLRGGTPVTTFVRGIDLRSTVLLNVLTLPRLQKQFPNESHTENQPTWI

KPIKSNESIPASSIGFVRGLFWQPAHIELCDPIGIGKCSCCGQESNLRYTGFLKEKFTFT

VNGLWPHPHSPCLVTVKKGEVEEKFLAFTTSAPSWTQISRVVVDKIIQNENGNRVAA

VVNQFRNIAPQSPLELIMGGYRNNQASILERRHDVLMFNQGWQQYGNVINEIVTVGL

GYKTALRKALYTFAEGFKNKDFKGAGVSVHETAERHFYRQSELLIPDVLANVNFSQ

ADEVIADLRDKLHQLCEMLFNQSVAPYAHHPKLISTLALARATLYKHLRELKPQGGP

SNG*

>nucleotide sequence of His$_6$-Dual-monopartite NLS SV40-FokI (Sharkey-ELD)-Cse1 ("His$_6$" disclosed as SEQ ID NO: 48)

[SEQ ID NO: 24]

ATGcatcaccatcatcaccac*CCGAAAAAAAAGCGCAAAGTGGATCCGAAGAAAAAACGTAAAG*

*TTGAAGATCCGAAAGA*CATGGCTCAACTGGTTAAAAGCGAACTGGAAGAGAAAAA

AAGTGAACTGCGCCACAAACTGAAATATGTGCCGCATGAATATATCGAGCTGAT

TGAAATTGCACGTAATCCGACCCAGGATCGTATTCTGGAAATGAAAGTGATGGA

ATTTTTTATGAAAGTGTACGGCTATCGCGGTGAACATCTGGGTGGTAGCCGTAAA

CCGGATGGTGCAATTTATACCGTTGGTAGCCCGATTGATTATGGTGTTATTGTTG

ATACCAAAGCCTATAGCGGTGGTTATAATCTGCCGATTGGTCAGGCAGATGAAA

TGGAACGTTATGTGGAAGAAAATCAGACCCGTGATAAACATCTGAATCCGAATG

AATGGTGGAAAGTTTATCCGAGCAGCGTTACCGAGTTTAAATTCCTGTTTGTTAG

CGGTCACTTCAAAGGCAACTATAAAGCACAGCTGACCCGTCTGAATCATATTACC

AATTGTAATGGTGCAGTTCTGAGCGTTGAAGAACTGCTGATTGGTGGTGAAATGA

TTAAAGCAGGCACCCTGACCCTGGAAGAAGTTCGTCGCAAATTTAACAATGGCG

AAATCAACTTTGCGGATCCCACCAACCGCGCGAAAGGCCTGGAAGCGGTGAG

CGTGGCGAGCatgaatttgcttattgataactggattcctgtacgccgcgaaacgggggggaaagtccaaatcataaatctg caatcgctatactgcagtagagatcagtggcgattaagtttgccccgtgacgatatggaactggccgctttagcactgctggtttgcattg ggcaaattatcgccccggcaaaagatgacgttgaatttcgacatcgcataatgaatccgctcactgaagatgagtttcaacaactcatcg cgccgtggatagatatgttctaccttaatcacgcagaacatcccctttatgcagaccaaaggtgtcaaagcaaatgatgtgactccaatgg aaaaactgttggctggggtaagcggcgcgacgaattgtgcatttgtcaatcaaccggggcagggtgaagcattatgtggtggatgcac tgcgattgcgttattcaaccaggcgaatcaggcaccaggttttggtggtggttttaaaagcggtttacgtggaggaacacctgtaacaac gttcgtacgtgggatcgatcttcgttcaacggtgttactcaatgtcctcacattacctcgtcttcaaaaacaatttcctaatgaatcacatacg gaaaaccaacctacctggattaaacctatcaagtccaatgagtctataccgcttcgtcaattgggttttgtccgtggtctattctggcaacc agcgcatattgaattatgcgatcccattgggattggtaaatgttcttgctgtggacaggaaagcaatttgcgttataccggttttcttaagga aaaatttacctttacagttaatgggctatggccccatccgcattccccttgtctggtaacagtcaagaagggggaggttgaggaaaaattt cttgctttcaccacctccgcaccatcatggacacaaatcagccgagttgtggtagataagattattcaaaatgaaatggaaatcgcgtg gcggcggttgtgaatcaattcagaaatattgcgccgcaaagtcctcttgaattgattatgggggggatatcgtaataatcaagcatctattct tgaacgcgtcatgatgtgttgatgtttaatcaggggtggcaacaatacggcaatgtgataaacgaaatagtgactgttggtttgggatat aaaacagccttacgcaaggcgttatatacctttgcagaagggtttaaaaataaagacttcaaaggggccggagtctctgttcatgagact gcagaaaggcatttctatcgacagagtgaattattaattcccgatgtactggcgaatgttaattttttcccaggctgatgaggtaatagctga

```
tttacgagacaaacttcatcaattgtgtgaaatgctattaatcaatctgtagctccctatgcacatcatcctaaattaataagcacattagcg cttgcccgcgccacgctatacaaacatttacgggagttaaaaccgcaaggagggccatcaaatggctga
```

>protein sequence of His$_6$-Dual-monopartite NLS SV40-FokI-(Sharkey-ELD)-Cse1 ("His$_6$" disclosed as SEQ ID NO: 48)

[SEQ ID NO: 25]

```
MHHHHHHPKKKRKVDPKKKRKVEDPKDMAQLVKSELEEKKSELRHKLKYVPHEYI

ELIEIARNPTQDRILEMKVMEFFMKVYGYRGEHLGGSRKPDGAIYTVGSPIDYGVIVD

TKAYSGGYNLPIGQADEMERYVEENQTRDKHLNPNEWWKVYPSSVTEFKFLFVSGH

FKGNYKAQLTRLNHITNCNGAVLSVEELLIGGEMIKAGTLTLEEVRRKFNNGEINFA

DPTNRAKGLEAVSVASMNLLIDNWIPVRPRNGGKVQIINLQSLYCSRDQWRLSLPRD

DMELAALALLVCIGQIIAPAKDDVEFRHRIMNPLTEDEFQQLIAPWIDMFYLNHAEHP

FMQTKGVKANDVTPMEKLLAGVSGATNCAFVNQPGQGEALCGGCTAIALFNQANQ

APGFGGGFKSGLRGGTPVTTFVRGIDLRSTVLLNVLTLPRLQKQFPNESHTENQPTWI

KPIKSNESIPASSIGFVRGLFWQPAHIELCDPIGIGKCSCCGQESNLRYTGFLKEKFTFT

VNGLWPHPHSPCLVTVKKGEVEEKFLAFTTSAPSWTQISRVVVDKIIQNENGNRVAA

VVNQFRNIAPQSPLELIMGGYRNNQASILERRHDVLMFNQGWQQYGNVINEIVTVGL

GYKTALRKALYTFAEGFKNKDFKGAGVSVHETAERHFYRQSELLIPDVLANVNFSQ

ADEVIADLRDKLHQLCEMLFNQSVAPYAHHPKLISTLALARATLYKHLRELKPQGGP

SNG*
```

DNA Cleavage Assay

The specificity and activity of the complexes was tested using an artificially constructed target plasmid as a substrate. This plasmid contains M13 and P7 binding sites on opposing strands such that both FokI domains face each other (see FIG. 11). The distance between the Cascade binding sites varies between 25 and 50 basepairs with 5 bp increments. As the binding sites of Cascade need to be flanked by any of four known PAM sequences (5'-protospacer-CTT/CAT/CTC/CCT-3' this distance range gives sufficient flexibility to design such a pair for almost any given sequence.

The sequences of the target plasmids used are as follows. The number indicated the distance between the M13 and P7 target sites. Protospacers are shown in bold, PAMs underlined:

Sequences of the target plasmids. The number indicates the distance between the M13 and P7 target sites. (protospacers in bold, PAMs underlined)

>50 bp

[SEQ ID NO: 26]
```
gaattcACAACGGTGAGCAAGTCACTGTTGGCAAGCCAGGATCTGAACAA

TACCGTCTTGCTTTCGAGCGCTAGCTCTAGAACTAGTCCTCAGCCTAGGC

CTCGTTCCGAAGCTGTCTTTCGCTGCTGAGGGTGACGATCCCGCATAGGC

GGCCTTTAACTCggatcc
```

>45 bp

[SEQ ID NO: 27]
```
gaattcACAACGGTGAGCAAGTCACTGTTGGCAAGCCAGGATCTGAACAA

TACCGTCTTTTCGAGCGCTAGCTCTAGAACTAGTCCTCAGCCTAGGCCTC

GTTCAAGCTGTCTTTCGCTGCTGAGGGTGACGATCCCGCATAGGCGGCCT

TTAACTCggatcc
```

>40 bp

[SEQ ID NO: 28]
```
gaattcACAACGGTGAGCAAGTCACTGTTGGCAAGCCAGGATCTGAACAA

TACCGTCTTCGAGCGCTAGCTCTAGAACTAGTCCTCAGCCTAGGCCTCGA

AGCTGTCTTTCGCTGCTGAGGGTGACGATCCCGCATAGGCGGCCTTTAAC

TCggatcc
```

>35 bp

[SEQ ID NO: 29]
```
gaattcACAACGGTGAGCAAGTCACTGTTGGCAAGCCAGGATCTGAACAA

TACCGTCTTGCGCTAGCTCTAGAACTAGTCCTCAGCCTAGGCCTAAGCTG

TCTTTCGCTGCTGAGGGTGACGATCCCGCATAGGCGGCCTTTAACTCgga tcc
```

>30 bp

[SEQ ID NO: 30]
```
gaattcACAACGGTGAGCAAGTCACTGTTGGCAAGCCAGGATCTGAACAA

TACCGTCTTGCTAGCTCTAGAACTAGTCCTCAGCCTAGGAAGCTGTCTTT

CGCTGCTGAGGGTGACGATCCCGCATAGGCGGCCTTTAACTCggatcc
```

>25 bp

[SEQ ID NO: 31]
```
gaattcACAACGGTGAGCAAGTCACTGTTGGCAAGCCAGGATCTGAACAA

TACCGTCTTCTCTAGAACTAGTCCTCAGCCTAGGAAGCTGTCTTTCGCTG

CTGAGGGTGACGATCCCGCATAGGCGGCCTTTAACTCggatcc
```

Cleavage of the target plasmids was analysed on agarose gels, where negatively supercoiled (nSC) plasmid can be distinguished from linearized- or nicked plasmid. The cleavage site of the Cascade$^{KKR/ELD}$ pair in a target vector was determined by isolating linear cleavage products from an agarose gel and filling in the recessed 3' ends left by FokI cleavage with the Klenow fragment of E. coli DNA polymerase to create blunt ends. The linear vector was self-ligated, transformed, amplified, isolated and sequenced. Filling in of recessed 3' ends and re-ligation will lead to extra nucleotides in the sequence that represents the overhang left by FokI cleavage. By aligning the sequence reads to the original sequence, the cleavage sites can be found on a clonal level and mapped. Below, the additional bases incorporated into the sequence after filling in recessed 3' ends left by FokI cleavage are underlined:

```
                      FokI cleavage
5' CTTGCGCTAGCTCTAGAA ↘ CTAGTCCTCAGCCTAGGCCTAAG 3'

3' GAACGCGATCGAGATCTTGATC AGGAGTCGGATCCGGATTC 5'

3' fill in, ligation
5' CTTGCGCTAGCTCTAGAA????-CTAGTCCTCAGCCTAGGC-
CTAAG 3'

3' GAACGCGATCGAGATCTTGATC-????CAGGAGTCGGATCCGGA

TTC 5'
```

Reading from top to bottom, the 5'-3' sequences above are SEQ ID NOs: 32-35, respectively.

Cleavage of a Target Locus in Human Cells

The human CCR5 gene encodes the C-C chemokine receptor type 5 protein, which serves as the receptor for the human immunodeficiency virus (HIV) on the surface of white blood cells. The CCR5 gene is targeted using a pair of Cascade$^{KKR/ELD}$ nucleases in addition to an artificial GFP locus. A suitable binding site pair is selected on the coding region of CCR5. Two separate CRISPR arrays containing uniform spacers targeting each of the binding sites are constructed using DNA synthesis (Geneart).

The human CCR5 target gene selection and CRISPR designs used are as follows:

```
>Part of genomic human CCR5 sequence, containing
whole ORF (position 347-1446).
                                    [SEQ ID NO: 36]
GGTGGAACAAGATGGATTATCAAGTGTCAAGTCCAATCTATGACATCAAT

TATTATACATCGGAGCCCTGCCAAAAAATCAATGTGAAGCAAATCGCAGC

CCGCCTCCTGCCTCCGCTCTACTCACTGGTGTTCATCTTTGGTTTTGTGG

GCAACATGCTGGTCATCCTCATCCTGATAAACTGCAAAAGGCTGAAGAGC

ATGACTGACATCTACCTGCTCAACCTGGCCATCTCTGACCTGTTTTTCCT

TCTTACTGTCCCCTTCTGGGCTCACTATGCTGCCGCCCAGTGGGACTTTG

GAAATACAATGTGTCAACTCTTGACAGGGCTCTATTTTATAGGCTTCTTC

TCTGGAATCTTCTTCATCATCCTCCTGACAATCGATAGGTACCTGGCTGT

CGTCCATGCTGTGTTTGCTTTAAAAGCCAGGACGGTCACCTTTGGGGTGG

TGACAAGTGTGATCACTTGGGTGGTGGCTGTGTTTGCGTCTCTCCCAGGA

ATCATCTTTACCAGATCTCAAAAAGAAGGTCTTCATTACACCTGCAGCTC

TCATTTTCCATACAGTCAGTATCAATTCTGGAAGAATTTCCAGACATTAA

AGATAGTCATCTTGGGGCTGGTCCTGCCGCTGCTTGTCATGGTCATCTGC

TACTCGGGAATCCTAAAAACTCTGCTTCGGTGTCGAAATGAGAAGAAGAG

GCACAGGGCTGTGAGGCTTATCTTCACCATCATGATTGTTTATTTTCTCT

TCTGGGCTCCCTACAACATTGTCCTTCTCCTGAACACCTTCCAGGAATTC
```

```
TTTGGCCTGAATAATTGCAGTAGCTCTAACAGGTTGGACCAAGCTATGCA

GGTGACAGAGACTCTTGGGATGACGCACTGCTGCATCAACCCCATCATCT

ATGCCTTTGTCGGGGAGAAGTTCAGAAACTACCTCTTAGTCTTCTTCCAA

AAGCACATTGCCAAACGCTTCTGCAAATGCTGTTCTATTTTCCAGCAAGA

GGCTCCCGAGCGAGCAAGCTCAGTTTACACCCGATCCACTGGGGAGCAGG

AAATATCTGTGGGCTTGTGACACGGACTCAAGTGGGCTGGTGACCCAGTC
```

Red1/2: chosen target sites (distance: 34 bp, PAM 5'-CTT-3'). "Red 1 is first appearing underlined sequence in the above. Red2 is the second underlined sequence.

```
>CRISPR array red1 (italics = spacers, bold =
repeats)
                                    [SEQ ID NO: 37]
ccatggTAATACGACTCACTATAGGGAGAATTAGCTGATCTTTAATAATA

AGGAAATGTTACATTAAGGTTGGTGGGTTGTTTTTATGGGAAAAAATGCT

TTAAGAACAAATGTATACTTTTAGAGAGTTCCCCGCGCCAGCGGGGATAA

ACCGCAAACACAGCATGGACGACAGCCAGGTACCTAGAGTTCCCCGCGCC

AGCGGGGATAAACCGCAAACACAGCATGGACGACAGCCAGGTACCTAGAG

TTCCCCGCGCCAGCGGGGATAAACCGCAAACACAGCATGGACGACAGCCA

GGTACCTAGAGTTCCCCGCGCCAGCGGGGATAAACCGAAAACAAAAGGCT

CAGTCGGAAGACTGGGCCTTTTGTTTTAACCCCTTGGGGCCTCTAAACGG

GTCTTGAGGGGTTTTTTGggtacc

>CRISPR array red2 (italics: spacers, bold:
repeats)
                                    [SEQ ID NO: 38]
ccatggTAATACGACTCACTATAGGGAGAATTAGCTGATCTTTAATAATA

AGGAAATGTTACATTAAGGTTGGTGGGTTGTTTTTATGGGAAAAAATGCT

TTAAGAACAAATGTATACTTTTAGAGAGTTCCCCGCGCCAGCGGGGATAA

ACCGTGTGATCACTTGGGTGGTGGCTGTGTTTGCGTGAGTTCCCCGCGCC

AGCGGGGATAAACCGTGTGATCACTTGGGTGGTGGCTGTGTTTGCGTGAG

TTCCCCGCGCCAGCGGGGATAAACCGTGTGATCACTTGGGTGGTGGCTGT

GTTTGCGTGAGTTCCCCGCGCCAGCGGGGATAAACCGAAAACAAAAGGCT

CAGTCGGAAGACTGGGCCTTTTGTTTTAACCCCTTGGGGCCTCTAAACGG

GTCTTGAGGGGTTTTTTGggtacc
```

Delivery of Cascade$^{KKR/ELD}$ into the Nucleus of Human Cells

Cascade is very stable as a multi-subunit protein-RNA complex and is easily produced in mg quantities in E. coli. Transfection or micro-injection of the complex in its intact form as purified from E. coli is used as methods of delivery (see FIG. 12). As shown in FIG. 12, Cascade-FokI nucleases are purified from E. coli and encapsulated in protein transfection vesicles. These are then fused with the cell membrane of human HepG2 cells releasing the nucleases in the cytoplasm (step 2). NLS sequences are then be recognized by importin proteins, which facilitate nucleopore passage (step 3). Cascade$^{KKR}$ (open rectangle) and Cascade$^{ELD}$ (filled rectangle) will then find and cleave their target site (step 4.), inducing DNA repair pathways that will alter the target site leading to desired changes. Cascade$^{KKR/ELD}$ nucleases need to act only once and require no permanent presence in the cell encoded on DNA.

To deliver Cascade into human cells, protein transfection reagents are used from various sources including Pierce, NEB, Fermentas and Clontech. These reagents have recently been developed for the delivery of antibodies, and are useful to transfect a broad range of human cell lines with efficiencies up to 90%. Human HepG2 cells are transfected. Also, other cell lines including CHO-K1, COS-7, HeLa, and non-embryonic stem cells, are transfected.

To import the Cascade$^{KKR/ELD}$ nuclease pair into the nucleus, a tandem monopartite nuclear localisation signal (NLS) from the large T-antigen of simian virus 40 (SV40) is fused to the N-terminus of FokI. This ensures import of only intact Cascade$^{ELD/KKR}$ into the nucleus. (The nuclear pore complex translocates RNA polymerases (550 kDa) and other large protein complexes). As a check prior to transformations, the nuclease activity of the Cascade$^{KKR/ELD}$ nuclease pair is checked in vitro using purified complexes and CCR5 PCR amplicons to exclude transfecting non-productive Cascade$^{KKR/ELD}$ nuclease pairs.

Surveyor Assay

Transfected cells are cultivated and passaged for several days. The efficiency of in vivo target DNA cleavage is then assessed by using the Surveyor assay of Guschin, D. Y., et al (2010) Methods Mol. Biol., 649: 247-256. Briefly, PCR amplicons of the target DNA locus will be mixed 1:1 with PCR amplicons from untreated cells. These are heated and allowed to anneal, giving rise to mismatches at target sites that have been erroneously repaired by NHEJ. A mismatch nuclease is then used to cleave only mismatched DNA molecules, giving a maximum of 50% of cleavage when target DNA cleavage by Cascade$^{KKR/ELD}$ is complete. This procedure was then followed up by sequencing of the target DNA amplicons of treated cells. The assay allows for rapid assessment and optimization of the delivery procedure.

Production of Cascade-Nuclease Pairs

The Cascade-nuclease complexes were constructed as explained above. Affinity purification from E. coli using the StrepII-tagged Cse2 subunit yields a complex with the expected stoichiometry when compared to native Cascade. Referring to FIG. 13, this shows the stoichiometry of native Cascade (1), Cascade$^{KKR}$ with P7 CrRNA and Cascade$^{ELD}$ with M13 CrRNA 24 h after purification using only Streptactin. Bands in native Cascade (1) are from top to bottom: Cse1, Cas7, Cas5, Cas6e, Cse2. Cascade$^{KKR/ELD}$ show the FokI-Cse1 fusion band and an additional band representing Cse1 with a small part of FokI as a result of proteolytic degradation.

Apart from an intact FokI-Cse1 fusion protein, we observed that a fraction of the FokI-Cse1-fusion protein is proteolytically cleaved, resulting in a Cse1 protein with only the linker and a small part of FokI attached to it (as confirmed by Mass Spectrometry, data not shown). In most protein isolations the fraction of degraded fusion protein is approximately 40%. The isolated protein is stably stored in the elution buffer (20 mM HEPES pH 7.5, 75 mM NaCl, 1 mM DTT, 4 mM desthiobiotin) with additional 0.1% Tween 20 and 50% glycerol at −20° C. Under these storage conditions, integrity and activity of the complex have been found stable for at least three weeks (data not shown).

Introduction of a His$_6$-Tag (SEQ ID NO: 48) and NLS to the Cascade-Nuclease

The Cascade nuclease fusion design was modified to incorporate a Nucleolar Localization Signal (NLS) to enable transport into the nucleus of eukaryotic cells. For this a tandem monopartite NLS from the large T-antigen of Simian Virus SV40 (sequence: PKKKRKVDPKKKRKV) (SEQ ID NO: 49) was translationally fused to the N-terminus of the FokI-Cse1 fusion protein, directly preceded by a His$_6$-tag at the N-terminus. The His$_6$-tag (sequence: MHHHHHH) ("His$_6$" disclosed as SEQ ID NO: 48 and "MHHHHHH" disclosed as SEQ ID NO: 50) allows for an additional Ni$^{2+}$-resin affinity purification step after StrepII purification. This additional step ensures the isolation of only full-length Cascade-nuclease fusion complex, and increases the efficiency of cleavage by eliminating the binding of non-intact Cascade complexes to the target site forming an unproductive nuclease pair.

In Vitro Cleavage Assay

Cascade$^{KKR/ELD}$ activity and specificity was assayed in vitro as described above. FIG. 14A and FIG. 14B show plasmids with distances between protospacers of 25-50 bp (5 bp increments, lanes 1-6) incubated with Cascade$^{KKR/ELD}$ for 30 minutes at 37° C. Lane 10 contains the target plasmid in its three possible topologies: the lowest band represents the initial, negatively supercoiled (nSC) form of the plasmid, the middle band represents the linearized form (cleaved by XbaI), whilst the upper band represents the open circular (OC) form (after nicking with Nt.BbrCI). Lane 7 shows incubation of a plasmid with both binding sites removed (negative control). Therefore FIG. 14A shows a typical cleavage assay using various target plasmids in which the binding sites are separated by 25 to 50 base pairs in 5 bp increments (lanes 1 to 6). These plasmids with distances of 25-50 bp were incubated with Cascade$^{KKR/ELD}$ carrying anti P7 and M13 crRNA respectively. A plasmid containing no binding sites served as a control (lane 7). The original plasmid exists in negatively supercoiled form (nSC, control lane 8), and nicked or linearized products are clearly distinguishable. Upon incubation a linear cleavage product is formed when binding sites were separated by 30, 35 and 40 base pairs (lanes 2, 3, 4). At 25, 45 and 50 base pairs distance (lanes 1, 5, 6), the target plasmid appeared to be incompletely cleaved leading to the nicked form (OC). These results show the best cleavage in plasmids with distances between 30 and 40 bp, giving sufficient flexibility when designing a crRNA pair for any given locus. Both shorter and longer distances result in increased nicking activity while creating less DSBs. There is very little activity on a plasmid where the two protospacers have been removed, showing target specificity (lane 7).

Cleavage Conditions

To assess the optimal buffer conditions for cleavage assays, and to estimate whether activity of the complex is expected at physiological conditions, the following two buffers were selected: (1) NEB4 (New England Biolabs, 50 mM potassium acetate, 20 mM Tris-acetate, 10 mM magnesium acetate, 1 mM dithiothreitol, pH 7.9) and (2) Buffer O (Fermentas, 50 mM Tris-HCl, 10 mM MgCl$_2$, 100 mM NaCl, 0.1 mg/mL BSA, pH 7.5). Of the two, NEB4 is recommended for optimal activity of the commercial intact FokI enzyme. Buffer O was chosen from a quick screen to give good activity and specificity (data not shown). FIG. 14B shows incubation with different buffers and different incubation times. Lanes 1-4 have been incubated with Fermentas Buffer O (lane 1, 2 for 15 minutes, lane 3, 4 for 30 minutes), lanes 5, 6 have been incubated with NEB4 (30 minutes). Lanes 1, 3, 5 used the target plasmid with 35 bp spacing, lanes 2, 4, 6 used the non-target plasmid (no binding sites). Lanes 7, 8 have been incubated with only Cascade$^{KKR}$ or Cascade$^{ELD}$ respectively (buffer O). Lane 9 is the topology marker as in (A). Lane 10 and 11 show the target and non-target plasmid incubated without addition of Cascade. Therefore in FIG. 14B, activity was tested on the target plasmid with 35 base pairs distance (lane 1, 3, 5) and a non-target control plasmid (lane 2, 4, 6). There was a high amount of unspecific nicking and less cleavage in NEB4 (lane 5,6), whilst buffer O shows only activity in the target plasmid with a high amount of specific cleavage and little nicking (lane 1-4). The difference is likely caused by the NaCl concentration in buffer O, higher ionic strength weakens protein-protein interactions, leading to less nonspecific activity. Incubation of 15 or 30 minutes shows little difference in both target and non-target plasmid (lane 1,2 or 3, 4 respectively). Addition of only one type of Cascade (P7$^{KKR}$ or M13$^{ELD}$) does not result in cleavage activity (lane 7, 8) as expected. This experiment shows that specific Cascade nuclease activity by a designed pair occurs when the NaCl concentration is at least 100 mM, which is near the physiological saline concentration inside cells (137 mM NaCl). The Cascade nuclease pair is expected to be fully active in vivo, in eukaryotic cells, while displaying negligible off-target cleavage activity.

Cleavage Site

The site of cleavage in the target plasmid with a spacing of 35 bp (pTarget35) was determined. FIG. 15 shows how sequencing reveals up- and downstream cleavage sites by Cascade$^{KKR/ELD}$ in the target plasmid with 35 base pair spacing. In FIG. 15A) is shown the target region within pTarget35 with annotated potential cleavage sites. Parts of the protospacers are indicated in red and blue. B) The bar chart shows four different cleavage patterns and their relative abundance within sequenced clones. The blue bars represent the generated overhang, while the left and right border of each bar represents the left and right cleavage site (see B for annotation).

FIG. 15A shows the original sequence of pTarget35, with numbered cleavage sites from −7 to +7 where 0 lies in the middle between the two protospacers (indicated in red and blue). Seventeen clones were sequenced and these all show cleavage around position 0, creating varying overhangs between 3 and 5 bp (see FIG. 15B). Overhangs of 4 are most abundant (cumulatively 88%), while overhangs of 3 and 5 occur only once (6% each). The cleavage occurred exactly as expected with no clones showing off target cleavage.

Cleaving a Target Locus in Human Cells.

Cascade$^{KKR/ELD}$ nucleases were successfully modified to contain an N-terminal His$_6$-tag (SEQ ID NO: 48) followed by a dual mono-partite Nucleolar Localisation Signal. These modified Cascade nuclease fusion proteins were co-expressed with either one of two synthetically constructed CRISPR arrays, each targeting a binding site in the human CCR5 gene. First the activity of this new nuclease pair is validated in vitro by testing the activity on a plasmid containing this region of the CCR5 gene. The nuclease pair is transfected to a human cell line, e.g. HeLa cell line. Efficiency of target cleavage is assessed using the Surveyor assay as described above.

The invention claimed is:

1. A Type I CRISPR-Cas system protein complex, comprising:
   an artificial fusion protein comprising a FokI fused to the N-terminus of a Cse1 protein subunit, wherein the designed fusion protein further comprises a linker polypeptide between the FokI and the Cse1 protein subunit;
   a Cas6 protein subunit;
   a Cas5 protein subunit;
   a Cse2 protein subunit;
   a Cas7 protein subunit; and
   a CRISPR-derived RNA (crRNA) comprising a spacer sequence complementary to a target nucleic acid.

2. The Type I CRISPR-Cas system protein complex of claim 1, wherein the artificial fusion protein further comprises an N-terminal nuclear localization signal.

3. The Type I CRISPR-Cas system protein complex of claim 1, wherein the artificial fusion further comprises an N-terminal His$_6$-tag.

4. The Type I CRISPR-Cas system protein complex claim of 1, wherein at least one of the Cas6 protein subunit, the Cas5 protein subunit, the Cse2 protein subunit, or the Cas7 protein subunit further comprises a N-terminal nuclear localization signal.

5. The Type I CRISPR-Cas system protein complex of claim 1, wherein at least one of the Cas6 protein subunit, the Cas5 protein subunit, the Cse2 protein subunit, or the Cas7 protein subunit further comprises an N-terminal Strep-tag.

6. The Type I CRISPR-Cas system protein complex claim 1, wherein at least one of the Cas6 protein subunit, the Cas5 protein subunit, the Cse2 protein subunit, or the Cas7 protein subunit further comprises an N-terminal His$_6$-tag.

7. The Type I CRISPR-Cas system protein complex of claim 1, wherein the FokI comprises a KKR Sharkey nuclease domain.

8. The Type I CRISPR-Cas system protein complex of claim 1, wherein the FokI comprises an ELD Sharkey nuclease domain.

9. The Type I CRISPR-Cas system protein complex of claim 1, further comprising a target DNA complementary to the spacer sequence.

10. The Type I CRISPR-Cas system protein complex of claim 9, wherein the target DNA is in genomic DNA.

11. An *Escherichia coli* cell, comprising:
    the Type I CRISPR-Cas system protein complex of claim 1.

* * * * *

UNITED STATES PATENT AND TRADEMARK OFFICE
CERTIFICATE OF CORRECTION

PATENT NO.        : 10,435,678 B2
APPLICATION NO.   : 15/802413
DATED             : October 8, 2019
INVENTOR(S)       : Stan Johan Jozef Brouns and John Van Der Oost Page 1 of 1

It is certified that error appears in the above-identified patent and that said Letters Patent is hereby corrected as shown below:

In the Specification

In Column 18, Line 30, delete "E. coll", and insert --E. coli--

In the Claims

In Claim 1, Column 121, Line 43, delete "designed", and insert --artificial--
In Claim 4, Column 121, Line 61, delete "a N-terminal", and insert --an N-terminal--
In Claim 6, Column 122, Line 43, delete "complex claim 1", and insert --complex of claim 1--

Signed and Sealed this
Fourteenth Day of January, 2020

Andrei Iancu
*Director of the United States Patent and Trademark Office*

UNITED STATES PATENT AND TRADEMARK OFFICE
CERTIFICATE OF CORRECTION

PATENT NO.        : 10,435,678 B2
APPLICATION NO.   : 15/802413
DATED             : October 8, 2019
INVENTOR(S)       : Stan Johan Jozef Brouns and John Van Der Oost It is certified that error appears in the above-identified patent and that said Letters Patent is hereby corrected as shown below:

In the Specification

Column 17, Line 47 delete:
"FIG. 3A, panel E: Brightfield image of the cells in (G)."
And insert:
--FIG. 3A, panel E: Brightfield image of the cells in (D).--

Column 17, Line 48 delete:
"FIG. 3A, panel F: Overlay of (G) and (H)."
And insert:
--FIG. 3A, panel F: Overlay of (D) and (E).--

Figure 3A:
Figure 3B:
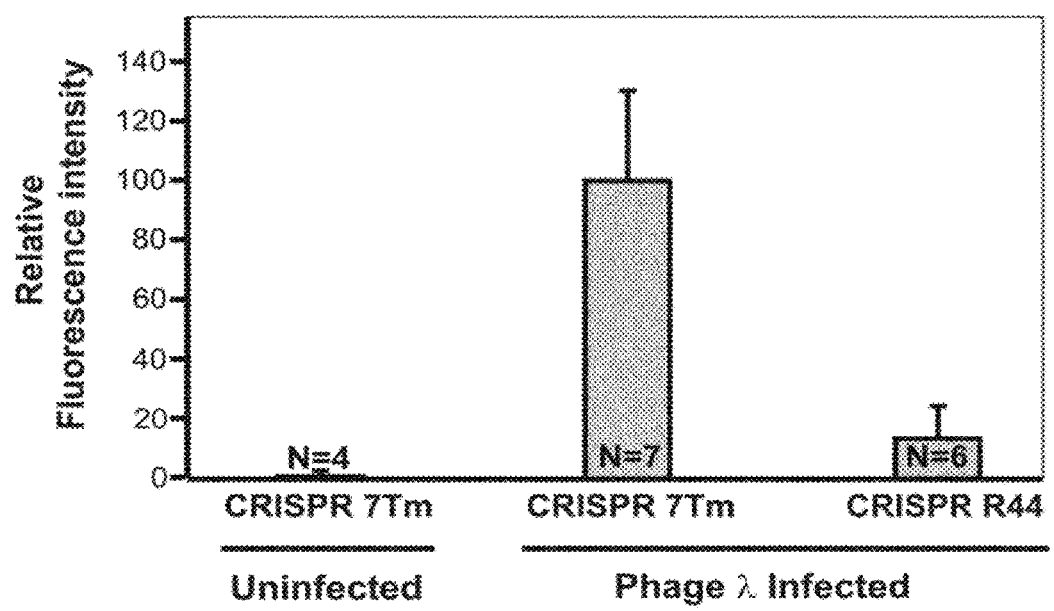
Figure 4A:
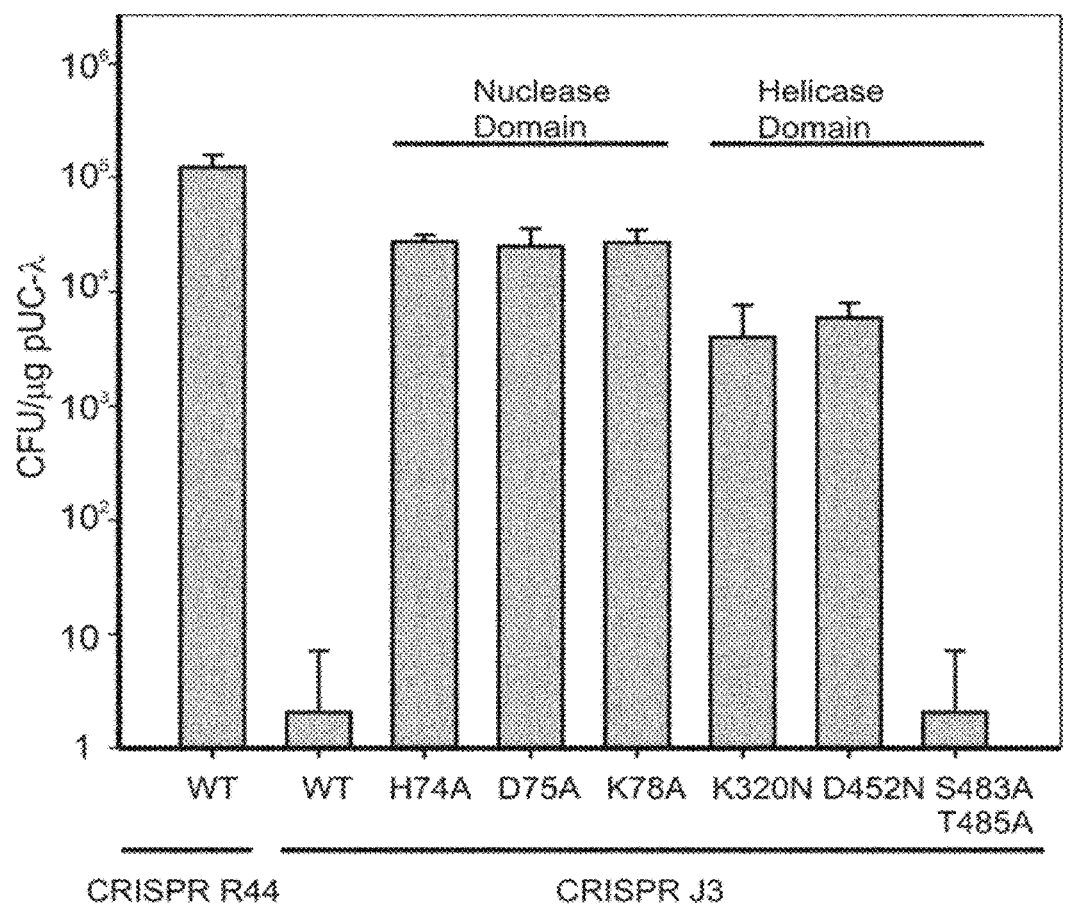
Figure 4B:
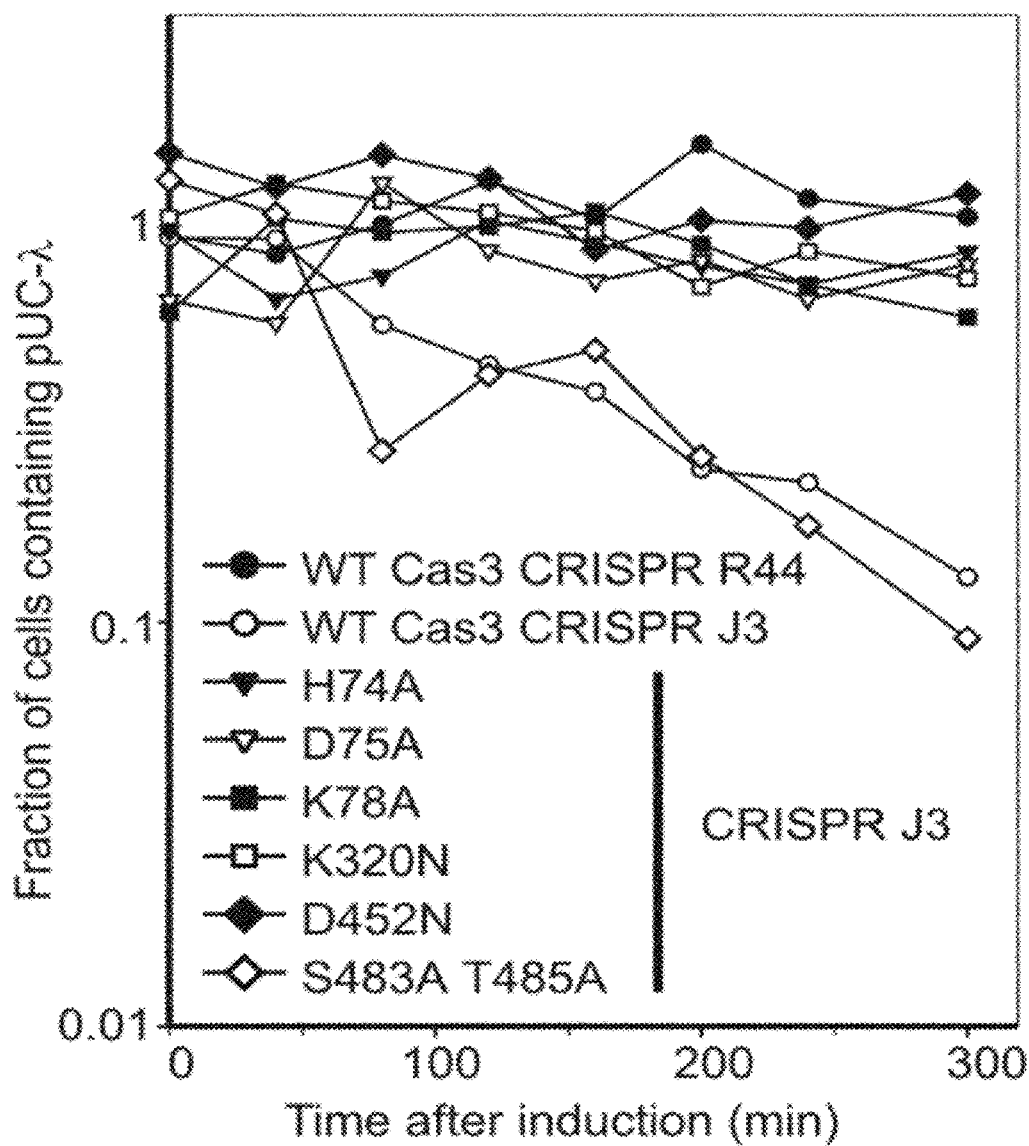

Column 17, Lines 51-53 delete:
"FIG. 3A, panel H: Brightfield image of the cells in (J). FIG. 3A, panel I: Overlay of (J) and (K)."
And insert:
--FIG. 3A, panel H: Brightfield image of the cells in (H). FIG. 3A, panel I: Overlay of (G) and (H).--

Column 24, Line 54-55 delete:
"Cas3 in the absence of invading DNA (FIG. 3A, FIG. 3B, FIG. 3C, FIG. 3P and FIG. 8)."
And insert:
--Cas3 in the absence of invading DNA (FIG. 3A, FIG. 3B, and FIG. 8)--

Column 24, Line 58-60 delete:
"anti-λ CRISPR 7Tm (FIG. 3D, FIG. 3E, FIG. 3F, FIG. 3P, and FIG. 8). When they co-express a non-targeting CRISPR R44 (FIG. 3G, FIG. 3H, FIG. 3I, FIG. 3P and FIG. 8),"
And insert:
--anti-λ CRISPR 7Tm (FIG. 3A panel D, FIG. 3A panel E, FIG. 3A panel F, FIG. 3B, and FIG. 8). When they co-express a non-targeting CRISPR R44 (FIG. 3A panel G, FIG. 3A panel H, FIG. 3A panel I, FIG. 3B and FIG. 8)--

Signed and Sealed this
Ninth Day of July, 2024

*Katherine Kelly Vidal*
Katherine Kelly Vidal
*Director of the United States Patent and Trademark Office*

SEQUENCE LISTING

```
<160> NUMBER OF SEQ ID NOS: 50

<210> SEQ ID NO 1
<211> LENGTH: 502
<212> TYPE: PRT
<213> ORGANISM: Escherichia coli

<400> SEQUENCE: 1

Met Asn Leu Leu Ile Asp Asn Trp Ile Pro Val Arg Pro Arg Asn Gly
1               5                   10                  15

Gly Lys Val Gln Ile Ile Asn Leu Gln Ser Leu Tyr Cys Ser Arg Asp
            20                  25                  30

Gln Trp Arg Leu Ser Leu Pro Arg Asp Asp Met Glu Leu Ala Ala Leu
        35                  40                  45

Ala Leu Leu Val Cys Ile Gly Gln Ile Ile Ala Pro Ala Lys Asp Asp
    50                  55                  60

Val Glu Phe Arg His Arg Ile Met Asn Pro Leu Thr Glu Asp Glu Phe
65                  70                  75                  80

Gln Gln Leu Ile Ala Pro Trp Ile Asp Met Phe Tyr Leu Asn His Ala
                85                  90                  95

Glu His Pro Phe Met Gln Thr Lys Gly Val Lys Ala Asn Asp Val Thr
            100                 105                 110

Pro Met Glu Lys Leu Leu Ala Gly Val Ser Gly Ala Thr Asn Cys Ala
        115                 120                 125

Phe Val Asn Gln Pro Gly Gln Gly Glu Ala Leu Cys Gly Gly Cys Thr
    130                 135                 140

Ala Ile Ala Leu Phe Asn Gln Ala Asn Gln Ala Pro Gly Phe Gly Gly
145                 150                 155                 160

Gly Phe Lys Ser Gly Leu Arg Gly Gly Thr Pro Val Thr Thr Phe Val
                165                 170                 175

Arg Gly Ile Asp Leu Arg Ser Thr Val Leu Leu Asn Val Leu Thr Leu
            180                 185                 190
```

Pro Arg Leu Gln Lys Gln Phe Pro Asn Glu Ser His Thr Glu Asn Gln
            195                 200                 205

Pro Thr Trp Ile Lys Pro Ile Lys Ser Asn Glu Ser Ile Pro Ala Ser
            210                 215                 220

Ser Ile Gly Phe Val Arg Gly Leu Phe Trp Gln Pro Ala His Ile Glu
225                 230                 235                 240

Leu Cys Asp Pro Ile Gly Ile Gly Lys Cys Ser Cys Cys Gly Gln Glu
                245                 250                 255

Ser Asn Leu Arg Tyr Thr Gly Phe Leu Lys Glu Lys Phe Thr Phe Thr
            260                 265                 270

Val Asn Gly Leu Trp Pro His Pro His Ser Pro Cys Leu Val Thr Val
            275                 280                 285

Lys Lys Gly Glu Val Glu Glu Lys Phe Leu Ala Phe Thr Thr Ser Ala
290                 295                 300

Pro Ser Trp Thr Gln Ile Ser Arg Val Val Asp Lys Ile Ile Gln
305                 310                 315                 320

Asn Glu Asn Gly Asn Arg Val Ala Ala Val Val Asn Gln Phe Arg Asn
                325                 330                 335

Ile Ala Pro Gln Ser Pro Leu Glu Leu Ile Met Gly Gly Tyr Arg Asn
            340                 345                 350

Asn Gln Ala Ser Ile Leu Glu Arg Arg His Asp Val Leu Met Phe Asn
            355                 360                 365

Gln Gly Trp Gln Gln Tyr Gly Asn Val Ile Asn Glu Ile Val Thr Val
            370                 375                 380

Gly Leu Gly Tyr Lys Thr Ala Leu Arg Lys Ala Leu Tyr Thr Phe Ala
385                 390                 395                 400

Glu Gly Phe Lys Asn Lys Asp Phe Lys Gly Ala Gly Val Ser Val His
                405                 410                 415

Glu Thr Ala Glu Arg His Phe Tyr Arg Gln Ser Glu Leu Leu Ile Pro
            420                 425                 430

Asp Val Leu Ala Asn Val Asn Phe Ser Gln Ala Asp Glu Val Ile Ala
            435                 440                 445

Asp Leu Arg Asp Lys Leu His Gln Leu Cys Glu Met Leu Phe Asn Gln
            450                 455                 460

Ser Val Ala Pro Tyr Ala His His Pro Lys Leu Ile Ser Thr Leu Ala
465                 470                 475                 480

Leu Ala Arg Ala Thr Leu Tyr Lys His Leu Arg Glu Leu Lys Pro Gln
                485                 490                 495

Gly Gly Pro Ser Asn Gly
            500

<210> SEQ ID NO 2
<211> LENGTH: 160
<212> TYPE: PRT
<213> ORGANISM: Escherichia coli

<400> SEQUENCE: 2

Met Ala Asp Glu Ile Asp Ala Met Ala Leu Tyr Arg Ala Trp Gln Gln
1               5                   10                  15

Leu Asp Asn Gly Ser Cys Ala Gln Ile Arg Arg Val Ser Glu Pro Asp
                20                  25                  30

Glu Leu Arg Asp Ile Pro Ala Phe Tyr Arg Leu Val Gln Pro Phe Gly
            35                  40                  45

Trp Glu Asn Pro Arg His Gln Gln Ala Leu Leu Arg Met Val Phe Cys

Leu Ser Ala Gly Lys Asn Val Ile Arg His Gln Asp Lys Lys Ser Glu
65                  70                  75                  80

Gln Thr Thr Gly Ile Ser Leu Gly Arg Ala Leu Ala Asn Ser Gly Arg
                85                  90                  95

Ile Asn Glu Arg Arg Ile Phe Gln Leu Ile Arg Ala Asp Arg Thr Ala
            100                 105                 110

Asp Met Val Gln Leu Arg Arg Leu Leu Thr His Ala Glu Pro Val Leu
        115                 120                 125

Asp Trp Pro Leu Met Ala Arg Met Leu Thr Trp Trp Gly Lys Arg Glu
    130                 135                 140

Arg Gln Gln Leu Leu Glu Asp Phe Val Leu Thr Thr Asn Lys Asn Ala
145                 150                 155                 160

<210> SEQ ID NO 3
<211> LENGTH: 363
<212> TYPE: PRT
<213> ORGANISM: Escherichia coli

<400> SEQUENCE: 3

Met Ser Asn Phe Ile Asn Ile His Val Leu Ile Ser His Ser Pro Ser
1               5                   10                  15

Cys Leu Asn Arg Asp Asp Met Asn Met Gln Lys Asp Ala Ile Phe Gly
            20                  25                  30

Gly Lys Arg Arg Val Arg Ile Ser Ser Gln Ser Leu Lys Arg Ala Met
        35                  40                  45

Arg Lys Ser Gly Tyr Tyr Ala Gln Asn Ile Gly Glu Ser Ser Leu Arg
    50                  55                  60

Thr Ile His Leu Ala Gln Leu Arg Asp Val Leu Arg Gln Lys Leu Gly
65                  70                  75                  80

Glu Arg Phe Asp Gln Lys Ile Ile Asp Lys Thr Leu Ala Leu Leu Ser
                85                  90                  95

Gly Lys Ser Val Asp Glu Ala Glu Lys Ile Ser Ala Asp Ala Val Thr
            100                 105                 110

Pro Trp Val Val Gly Ile Ala Trp Phe Cys Glu Gln Val Ala Lys
        115                 120                 125

Ala Glu Ala Asp Asn Leu Asp Asp Lys Lys Leu Leu Lys Val Leu Lys
    130                 135                 140

Glu Asp Ile Ala Ala Ile Arg Val Asn Leu Gln Gln Gly Val Asp Ile
145                 150                 155                 160

Ala Leu Ser Gly Arg Met Ala Thr Ser Gly Met Met Thr Glu Leu Gly
                165                 170                 175

Lys Val Asp Gly Ala Met Ser Ile Ala His Ala Ile Thr Thr His Gln
            180                 185                 190

Val Asp Ser Asp Ile Asp Trp Phe Thr Ala Val Asp Asp Leu Gln Glu
        195                 200                 205

Gln Gly Ser Ala His Leu Gly Thr Gln Glu Phe Ser Ser Gly Val Phe
    210                 215                 220

Tyr Arg Tyr Ala Asn Ile Asn Leu Ala Gln Leu Gln Glu Asn Leu Gly
225                 230                 235                 240

Gly Ala Ser Arg Glu Gln Ala Leu Glu Ile Ala Thr His Val His
                245                 250                 255

Met Leu Ala Thr Glu Val Pro Gly Ala Lys Gln Arg Thr Tyr Ala Ala
            260                 265                 270

```
Phe Asn Pro Ala Asp Met Val Met Val Asn Phe Ser Asp Met Pro Leu
                275                 280                 285

Ser Met Ala Asn Ala Phe Glu Lys Ala Val Lys Ala Lys Asp Gly Phe
    290                 295                 300

Leu Gln Pro Ser Ile Gln Ala Phe Asn Gln Tyr Trp Asp Arg Val Ala
305                 310                 315                 320

Asn Gly Tyr Gly Leu Asn Gly Ala Ala Ala Gln Phe Ser Leu Ser Asp
                325                 330                 335

Val Asp Pro Ile Thr Ala Gln Val Lys Gln Met Pro Thr Leu Glu Gln
                340                 345                 350

Leu Lys Ser Trp Val Arg Asn Asn Gly Glu Ala
            355                 360
```

<210> SEQ ID NO 4
<211> LENGTH: 224
<212> TYPE: PRT
<213> ORGANISM: Escherichia coli

<400> SEQUENCE: 4

```
Met Arg Ser Tyr Leu Ile Leu Arg Leu Ala Gly Pro Met Gln Ala Trp
1               5                   10                  15

Gly Gln Pro Thr Phe Glu Gly Thr Arg Pro Thr Gly Arg Phe Pro Thr
                20                  25                  30

Arg Ser Gly Leu Leu Gly Leu Leu Gly Ala Cys Leu Gly Ile Gln Arg
            35                  40                  45

Asp Asp Thr Ser Ser Leu Gln Ala Leu Ser Glu Ser Val Gln Phe Ala
        50                  55                  60

Val Arg Cys Asp Glu Leu Ile Leu Asp Asp Arg Arg Val Ser Val Thr
65                  70                  75                  80

Gly Leu Arg Asp Tyr His Thr Val Leu Gly Ala Arg Glu Asp Tyr Arg
                85                  90                  95

Gly Leu Lys Ser His Glu Thr Ile Gln Thr Trp Arg Glu Tyr Leu Cys
                100                 105                 110

Asp Ala Ser Phe Thr Val Ala Leu Trp Leu Thr Pro His Ala Thr Met
            115                 120                 125

Val Ile Ser Glu Leu Glu Lys Ala Val Leu Lys Pro Arg Tyr Thr Pro
130                 135                 140

Tyr Leu Gly Arg Arg Ser Cys Pro Leu Thr His Pro Leu Phe Leu Gly
145                 150                 155                 160

Thr Cys Gln Ala Ser Asp Pro Gln Lys Ala Leu Leu Asn Tyr Glu Pro
                165                 170                 175

Val Gly Gly Asp Ile Tyr Ser Glu Glu Ser Val Thr Gly His His Leu
                180                 185                 190

Lys Phe Thr Ala Arg Asp Glu Pro Met Ile Thr Leu Pro Arg Gln Phe
            195                 200                 205

Ala Ser Arg Glu Trp Tyr Val Ile Lys Gly Gly Met Asp Val Ser Gln
210                 215                 220
```

<210> SEQ ID NO 5
<211> LENGTH: 199
<212> TYPE: PRT
<213> ORGANISM: Escherichia coli

<400> SEQUENCE: 5

```
Met Tyr Leu Ser Lys Val Ile Ile Ala Arg Ala Trp Ser Arg Asp Leu
1               5                   10                  15
```

Tyr Gln Leu His Gln Gly Leu Trp His Leu Phe Pro Asn Arg Pro Asp
            20                  25                  30

Ala Ala Arg Asp Phe Leu Phe His Val Glu Lys Arg Asn Thr Pro Glu
        35                  40                  45

Gly Cys His Val Leu Leu Gln Ser Ala Gln Met Pro Val Ser Thr Ala
    50                  55                  60

Val Ala Thr Val Ile Lys Thr Lys Gln Val Glu Phe Gln Leu Gln Val
65                  70                  75                  80

Gly Val Pro Leu Tyr Phe Arg Leu Arg Ala Asn Pro Ile Lys Thr Ile
                85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
        115                 120                 125

Lys Leu Gly Asn Ala Ala Arg Val Glu Asp Val His Pro Ile Ser Glu
    130                 135                 140

Arg Pro Gln Tyr Phe Ser Gly Asp Gly Lys Ser Gly Lys Ile Gln Thr
145                 150                 155                 160

Val Cys Phe Glu Gly Val Leu Thr Ile Asn Asp Ala Pro Ala Leu Ile
                165                 170                 175

Asp Leu Val Gln Gln Gly Ile Gly Pro Ala Lys Ser Met Gly Cys Gly
            180                 185                 190

Leu Leu Ser Leu Ala Pro Leu
            195

<210> SEQ ID NO 6
<211> LENGTH: 392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
actggaaagc gggcagtgaa aggaaggccc atgaggccag ttaattaagc ggatcctggc      60
ggcggcagcg gcggcggcag cgacaagcag aagaacggca tcaaggcgaa cttcaagatc     120
cgccacaaca tcgaggacgg cggcgtgcag ctcgccgacc actaccagca gaacaccccc     180
atcggcgacg gccccgtgct gctgcccgac aaccactacc tgagctacca gtccgccctg     240
agcaaagacc ccaacgagaa gcgcgatcac atggtcctgc tggagttcgt gaccgccgcc     300
gggatcactc tcggcatgga cgagctgtac aagtaagcgg ccgcggcgcg cctaggcctt     360
gacggccttc cttcaattcg ccctatagtg ag                                    392

<210> SEQ ID NO 7
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cactataggg cgaattggcg gaaggccgtc aaggccgcat ttaattaagc ggccgcaggc      60
ggcggcagcg gcggcggcag catggtgagc aagggcgagg agctgttcac cggggtggtg     120
cccatcctgg tcgagctgga cggcgacgta aacggccaca agttcagcgt gtccggcgag     180
ggcgagggcg atgccaccta cggcaagctg accctgaagc tcatctgcac caccggcaag     240

```
ctgcccgtgc cctggcccac cctcgtgacc accctcggct acggcctgca gtgcttcgcc        300
cgctaccccg accacatgaa gcagcacgac ttcttcaagt ccgccatgcc cgaaggctac        360
gtccaggagc gcaccatctt cttcaaggac gacggcaact acaagacccg cgccgaggtg        420
aagttcgagg gcgacaccct ggtgaaccgc atcgagctga agggcatcga cttcaaggag        480
gacggcaaca tcctggggca caagctggag tacaactaca acagccacaa cgtctatatc        540
acggcctaac tcgagggcgc gccctgggcc tcatgggcct tccgctcact gcccgctttc        600
cag                                                                      603
```

```
<210> SEQ ID NO 8
<211> LENGTH: 679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cactataggg cgaattggcg gaaggccgtc aaggccgcat gagctccatg gaaacaaaga         60
attagctgat ctttaataat aaggaaatgt tacattaagg ttggtgggtt gtttttatgg        120
gaaaaaatgc tttaagaaca aatgtatact tttagagagt tccccgcgcc agcggggata        180
aaccgggccg attgaaggtc cggtggatgg cttaaaagag ttccccgcgc cagcggggat        240
aaaccgccgc aggtacagca ggtagcgcag atcatcaaga gttccccgcg ccagcgggga        300
taaaccgact tctctccgaa aagtcaggac gctgtggcag agttccccgc gccagcgggg        360
ataaaccgcc tacgcgctga acgccagcgg tgtggtgaat gagttccccg cgccagcggg        420
gataaaccgg tgtggccatg cacgccttta acggtgaact ggagttcccc gcgccagcgg        480
ggataaaccg cacgaactca gccagaacga caaacaaaag gcgagttccc cgcgccagcg        540
gggataaacc ggcaccagta cgcgccccac gctgacggtt tctgagttcc ccgcgccagc        600
ggggataaac cgcagctccc attttcaaac ccaggtaccc tgggcctcat gggccttccg        660
ctcactgccc gctttccag                                                    679
```

```
<210> SEQ ID NO 9
<211> LENGTH: 685
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gagctcccgg gctgacggta atagaggcac ctacaggctc cggtaaaacg gaaacagcgc         60
tggcctatgc ttggaaactt attgatcaac aaattgcgga tagtgttatt tttgccctcc        120
caacacaagc taccgcgaat gctatgctta cgagaatgga agcgagcgcg agccacttat        180
tttcatcccc aaatcttatt cttgctcatg gcaattcacg gtttaaccac ctctttcaat        240
caataaaatc acgcgcgatt actgaacagg ggcaagaaga agcgtgggtt cagtgttgtc        300
agtggttgtc acaaagcaat aagaaagtgt tccttgggca atcggcgtt tgcacgattg        360 atcaggtgtt gatttcggta ttgccagtta acaccgcctt tatccgtggt ttgggaattg        420
gtagatctgt tttaattgtt aatgaagttc atgcttacga cacctatatg aacggcttgc        480
tcgaggcagt gctcaaggct caggctgatg tgggagggag tgttattctt ctttccgcaa        540
```

```
ccctaccaat gaaacaaaaa cagaagcttc tggatactta tggtctgcat acagatccag    600
tggaaaataa ctccgcatat ccactcatta actggcgagg tgtgaatggt gcgcaacgtt    660
ttgatctgct agcggatccg gtacc                                          685
```

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
atagcgccat ggaaccttt aaatatatat gccatta                               37
```

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
acagtgggat ccgctttggg atttgcaggg atgactctgg t                         41
```

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
atagcgtcat gaatttgctt attgataact ggattcctgt acg                       43
```

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
acagtggcgg ccgcgccatt tgatggccct ccttgcggtt ttaa                      44
```

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
cgtatatcaa actttccaat agcatgaaga gcaatgaaaa ataac                     45
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgataccgc gagacccacg ctc                                             23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggataaagt tgcaggacca cttc                                            24

<210> SEQ ID NO 17
<211> LENGTH: 199
<212> TYPE: PRT
<213> ORGANISM: Escherichia coli

<400> SEQUENCE: 17

Met Tyr Leu Ser Lys Val Ile Ile Ala Arg Ala Trp Ser Arg Asp Leu
1               5                   10                  15

Tyr Gln Leu His Gln Gly Leu Trp His Leu Phe Pro Asn Arg Pro Asp
            20                  25                  30

Ala Ala Arg Asp Phe Leu Phe His Val Glu Lys Arg Asn Thr Pro Glu
        35                  40                  45

Gly Cys His Val Leu Leu Gln Ser Ala Gln Met Pro Val Ser Thr Ala
    50                  55                  60

Val Ala Thr Val Ile Lys Thr Lys Gln Val Glu Phe Gln Leu Gln Val
65                  70                  75                  80

Gly Val Pro Leu Tyr Phe Arg Leu Arg Ala Asn Pro Ile Lys Thr Ile
                85                  90                  95

Leu Asp Asn Gln Lys Arg Leu Asp Ser Lys Gly Asn Ile Lys Arg Cys
            100                 105                 110

Arg Val Pro Leu Ile Lys Glu Ala Glu Gln Ile Ala Trp Leu Gln Arg
        115                 120                 125

Lys Leu Gly Asn Ala Ala Arg Val Glu Asp Val His Pro Ile Ser Glu
    130                 135                 140

Arg Pro Gln Tyr Phe Ser Gly Asp Gly Lys Ser Gly Lys Ile Gln Thr
145                 150                 155                 160

Val Cys Phe Glu Gly Val Leu Thr Ile Asn Asp Ala Pro Ala Leu Ile
                165                 170                 175

Asp Leu Val Gln Gln Gly Ile Gly Pro Ala Lys Ser Met Gly Cys Gly
            180                 185                 190

Leu Leu Ser Leu Ala Pro Leu
        195

<210> SEQ ID NO 18
<211> LENGTH: 2154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggctcaac tggttaaaag cgaactggaa gagaaaaaaa gtgaactgcg ccacaaactg     60
aaatatgtgc cgcatgaata tatcgagctg attgaaattg cacgtaatcc gacccaggat    120

```
cgtattctgg aaatgaaagt gatggaattt tttatgaaag tgtacggcta tcgcggtgaa      180
catctgggtg gtagccgtaa accggatggt gcaatttata ccgttggtag cccgattgat      240
tatggtgtta ttgttgatac caaagcctat agcggtggtt ataatctgcc gattggtcag      300
gcagatgaaa tggaacgtta tgtggaagaa atcagaccc gtgataaaca tctgaatccg        360
aatgaatggt ggaaagttta tccgagcagc gttaccgagt ttaaattcct gtttgttagc      420
ggtcacttca aaggcaacta taagcacag ctgacccgtc tgaatcatat taccaattgt         480
aatggtgcag ttctgagcgt tgaagaactg ctgattggtg gtgaaatgat taaagcaggc      540
accctgaccc tggaagaagt tcgtcgcaaa tttaacaatg gcgaaatcaa ctttgcggat      600
cccaccaacc gcgcgaaagg cctggaagcg gtgagcgtgg cgagcatgaa tttgcttatt      660
gataactgga ttcctgtacg cccgcgaaac gggggggaaag tccaaatcat aaatctgcaa    720
tcgctatact gcagtagaga tcagtggcga ttaagtttgc cccgtgacga tatggaactg    780
gccgctttag cactgctggt ttgcattggg caaattatcg ccccggcaaa agatgacgtt      840
gaatttcgac atcgcataat gaatccgctc actgaagatg agtttcaaca actcatcgcg     900
ccgtggatag atatgttcta ccttaatcac gcagaacatc cctttatgca gaccaaaggt     960
gtcaaagcaa atgatgtgac tccaatggaa aaactgttgg ctggggtaag cggcgcgacg     1020
aattgtgcat ttgtcaatca accggggcag ggtgaagcat tatgtggtgg atgcactgcg    1080
attgcgttat tcaaccaggc gaatcaggca ccaggttttg gtggtggttt taaaagcggt    1140
ttacgtggag gaacacctgt aacaacgttc gtacgtggga tcgatcttcg ttcaacggtg    1200
ttactcaatg tcctcacatt acctcgtctt caaaaacaat ttcctaatga atcacatacg     1260
gaaaaccaac ctacctggat taaacctatc aagtccaatg agtctatacc tgcttcgtca    1320
attgggtttg tccgtggtct attctggcaa ccagcgcata ttgaattatg cgatcccatt     1380
gggattggta atgttcttg ctgtggacag gaaagcaatt tgcgttatac cggttttctt       1440
aaggaaaaat ttaccttac agttaatggg ctatggcccc atccgcattc cccttgtctg      1500
gtaacagtca agaaggggga ggttgaggaa aaatttcttg cttttcaccac ctccgcacca    1560 tcatggacac aaatcagccg agttgtggta gataagatta ttcaaaatga aaatggaaat    1620
cgcgtggcgg cggttgtgaa tcaattcaga atattgcgc cgcaaagtcc tcttgaattg    1680
attatggggg gatatcgtaa taatcaagca tctattcttg aacggcgtca tgatgtgttg    1740
atgtttaatc aggggtggca acaatacggc aatgtgataa acgaaatagt gactgttggt    1800
ttgggatata aaacagcctt acgcaaggcg ttatatacct ttgcagaagg gtttaaaaat    1860
aaagacttca aaggggccgg agtctctgtt catgagactg cagaaaggca tttctatcga    1920
cagagtgaat tattaattcc cgatgtactg gcgaatgtta tttttcccca ggctgatgag    1980
gtaatagctg atttacgaga caaacttcat caattgtgtg aaatgctatt taatcaatct    2040
gtagctccct atgcacatca tcctaaatta ataagcacat tagcgcttgc ccgcgccacg    2100
ctatacaaac atttacggga gttaaaaccg caaggagggc catcaaatgg ctga          2154
```

<210> SEQ ID NO 19
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

-continued

```
Met Ala Gln Leu Val Lys Ser Glu Leu Glu Lys Lys Ser Glu Leu
1               5                   10                  15

Arg His Lys Leu Lys Tyr Val Pro His Glu Tyr Ile Glu Leu Ile Glu
                20                  25                  30

Ile Ala Arg Asn Pro Thr Gln Asp Arg Ile Leu Glu Met Lys Val Met
                35                  40                  45

Glu Phe Phe Met Lys Val Tyr Gly Tyr Arg Gly Glu His Leu Gly Gly
        50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Glu Arg Tyr Val Glu Glu Asn Gln
                100                 105                 110

Thr Arg Asp Lys His Leu Asn Pro Asn Glu Trp Trp Lys Val Tyr Pro
            115                 120                 125

Ser Ser Val Thr Glu Phe Lys Phe Leu Phe Val Ser Gly His Phe Lys
            130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe Ala Asp Pro Thr Asn Arg Ala Lys Gly Leu
            195                 200                 205

Glu Ala Val Ser Val Ala Ser Met Asn Leu Leu Ile Asp Asn Trp Ile
210                 215                 220

Pro Val Arg Pro Arg Asn Gly Lys Val Gln Ile Ile Asn Leu Gln
225                 230                 235                 240

Ser Leu Tyr Cys Ser Arg Asp Gln Trp Arg Leu Ser Leu Pro Arg Asp
            245                 250                 255

Asp Met Glu Leu Ala Ala Leu Ala Leu Leu Val Cys Ile Gly Gln Ile
            260                 265                 270

Ile Ala Pro Ala Lys Asp Asp Val Glu Phe Arg His Arg Ile Met Asn
            275                 280                 285

Pro Leu Thr Glu Asp Glu Phe Gln Gln Leu Ile Ala Pro Trp Ile Asp
290                 295                 300

Met Phe Tyr Leu Asn His Ala Glu His Pro Phe Met Gln Thr Lys Gly
305                 310                 315                 320

Val Lys Ala Asn Asp Val Thr Pro Met Glu Lys Leu Leu Ala Gly Val
            325                 330                 335

Ser Gly Ala Thr Asn Cys Ala Phe Val Asn Gln Pro Gly Gln Gly Glu
            340                 345                 350

Ala Leu Cys Gly Gly Cys Thr Ala Ile Ala Leu Phe Asn Gln Ala Asn
            355                 360                 365

Gln Ala Pro Gly Phe Gly Gly Phe Lys Ser Gly Leu Arg Gly Gly
            370                 375                 380

Thr Pro Val Thr Thr Phe Val Arg Gly Ile Asp Leu Arg Ser Thr Val
385                 390                 395                 400

Leu Leu Asn Val Leu Thr Leu Pro Arg Leu Gln Lys Gln Phe Pro Asn
                405                 410                 415
```

Glu Ser His Thr Glu Asn Gln Pro Thr Trp Ile Lys Pro Ile Lys Ser
                420                 425                 430

Asn Glu Ser Ile Pro Ala Ser Ser Ile Gly Phe Val Arg Gly Leu Phe
            435                 440                 445

Trp Gln Pro Ala His Ile Glu Leu Cys Asp Pro Ile Gly Ile Gly Lys
    450                 455                 460

Cys Ser Cys Cys Gly Gln Glu Ser Asn Leu Arg Tyr Thr Gly Phe Leu
465                 470                 475                 480

Lys Glu Lys Phe Thr Phe Val Asn Gly Leu Trp Pro His Pro His
                485                 490                 495

Ser Pro Cys Leu Val Thr Val Lys Lys Gly Glu Val Glu Lys Phe
            500                 505                 510

Leu Ala Phe Thr Thr Ser Ala Pro Ser Trp Thr Gln Ile Ser Arg Val
        515                 520                 525

Val Val Asp Lys Ile Ile Gln Asn Glu Asn Gly Asn Arg Val Ala Ala
530                 535                 540

Val Val Asn Gln Phe Arg Asn Ile Ala Pro Gln Ser Pro Leu Glu Leu
545                 550                 555                 560

Ile Met Gly Gly Tyr Arg Asn Asn Gln Ala Ser Ile Leu Glu Arg Arg
                565                 570                 575

His Asp Val Leu Met Phe Asn Gln Gly Trp Gln Gln Tyr Gly Asn Val
            580                 585                 590

Ile Asn Glu Ile Val Thr Val Gly Leu Gly Tyr Lys Thr Ala Leu Arg
        595                 600                 605

Lys Ala Leu Tyr Thr Phe Ala Glu Gly Phe Lys Asn Lys Asp Phe Lys
610                 615                 620

Gly Ala Gly Val Ser Val His Glu Thr Ala Glu Arg His Phe Tyr Arg
625                 630                 635                 640

Gln Ser Glu Leu Leu Ile Pro Asp Val Leu Ala Asn Val Asn Phe Ser
                645                 650                 655

Gln Ala Asp Glu Val Ile Ala Asp Leu Arg Asp Lys Leu His Gln Leu
            660                 665                 670

Cys Glu Met Leu Phe Asn Gln Ser Val Ala Pro Tyr Ala His His Pro
        675                 680                 685

Lys Leu Ile Ser Thr Leu Ala Leu Ala Arg Ala Thr Leu Tyr Lys His
690                 695                 700

Leu Arg Glu Leu Lys Pro Gln Gly Gly Pro Ser Asn Gly
705                 710                 715

<210> SEQ ID NO 20
<211> LENGTH: 2154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggctcaac tggttaaaag cgaactggaa gagaaaaaaa gtgaactgcg ccacaaactg      60
aaatatgtgc cgcatgaata tatcgagctg attgaaattg cacgtaatcc gacccaggat     120
cgtattctgg aaatgaaagt gatggaattt tttatgaaag tgtacggcta tcgcggtgaa     180
catctgggtg gtagccgtaa accggatggt gcaatttata ccgttggtag cccgattgat     240
tatggtgtta ttgttgatac caaagcctat agcggtggtt ataatctgcc gattggtcag     300
gcagatgaaa tgcagcgtta tgtgaaagaa aatcagaccc gcaacaaaca tattaacccg     360

```
aatgaatggt ggaaagttta tccgagcagc gttaccgagt ttaaattcct gtttgttagc      420
ggtcacttca aaggcaacta taaagcacag ctgacccgtc tgaatcgtaa aaccaattgt      480
aatggtgcag ttctgagcgt tgaagaactg ctgattggtg gtgaaatgat taaagcaggc      540
accctgaccc tggaagaagt tcgtcgcaaa tttaacaatg gcgaaatcaa ctttgcggat      600
cccaccaacc gcgcgaaagg cctggaagcg gtgagcgtgg cgagcatgaa tttgcttatt      660
gataactgga ttcctgtacg cccgcgaaac gggggggaaag tccaaatcat aaatctgcaa      720
tcgctatact gcagtagaga tcagtggcga ttaagtttgc cccgtgacga tatggaactg      780
gccgctttag cactgctggt ttgcattggg caaattatcg ccccggcaaa agatgacgtt      840
gaatttcgac atcgcataat gaatccgctc actgaagatg agtttcaaca actcatcgcg      900
ccgtggatag atatgttcta ccttaatcac gcagaacatc cctttatgca gaccaaaggt      960
gtcaaagcaa atgatgtgac tccaatggaa aaactgttgg ctggggtaag cggcgcgacg     1020
aattgtgcat ttgtcaatca accggggcag ggtgaagcat tatgtggtgg atgcactgcg     1080
attgcgttat tcaaccaggc gaatcaggca ccaggttttg gtggtggttt taaaagcggt     1140
ttacgtggag gaacacctgt aacaacgttc gtacgtggga tcgatcttcg ttcaacggtg     1200
ttactcaatg tcctcacatt acctcgtctt caaaaacaat ttcctaatga atcacatacg     1260
gaaaaccaac ctacctggat taaacctatc aagtccaatg agtctatacc tgcttcgtca     1320
attgggtttg tccgtggtct attctggcaa ccagcgcata ttgaattatg cgatcccatt     1380
gggattggta atgttcttg ctgtggacag gaaagcaatt tgcgttatac cggttttctt      1440
aaggaaaaat ttacctttac agttaatggg ctatggcccc atccgcattc cccttgtctg     1500
gtaacagtca agaaggggga ggttgaggaa aaatttcttg cttttcaccac ctccgcacca     1560
tcatggacac aaatcagccg agttgtggta gataagatta ttcaaaatga aaatggaaat     1620
cgcgtggcgg cggttgtgaa tcaattcaga aatattgcgc cgcaaagtcc tcttgaattg     1680
attatggggg gatatcgtaa taatcaagca tctattcttg aacggcgtca tgatgtgttg     1740
atgtttaatc aggggtggca acaatacggc aatgtgataa acgaaatagt gactgttggt     1800
ttgggatata aaacagcctt acgcaaggcg ttatatacct ttgcagaagg gtttaaaaat     1860
aaagacttca aaggggccgg agtctctgtt catgagactg cagaaaggca tttctatcga     1920
cagagtgaat tattaattcc cgatgtactg gcgaatgtta ttttttccca ggctgatgag     1980
gtaatagctg atttacgaga caaacttcat caattgtgtg aaatgctatt taatcaatct     2040
gtagctccct atgcacatca tcctaaatta ataagcacat tagcgcttgc ccgcgccacg     2100
ctatacaaac atttacggga gttaaaaccg caaggagggc catcaaatgg ctga            2154
```

<210> SEQ ID NO 21
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Pro Thr Gln Asp Arg Ile Leu Glu Met Lys Val Met

```
                35                  40                  45
Glu Phe Phe Met Lys Val Tyr Gly Tyr Arg Gly Glu His Leu Gly Gly
 50                  55                  60

Ser Arg Lys Pro Asp Gly Ala Ile Tyr Thr Val Gly Ser Pro Ile Asp
 65                  70                  75                  80

Tyr Gly Val Ile Val Asp Thr Lys Ala Tyr Ser Gly Tyr Asn Leu
                85                  90                  95

Pro Ile Gly Gln Ala Asp Glu Met Gln Arg Tyr Val Lys Glu Asn Gln
                100                 105                 110

Thr Arg Asn Lys His Ile Asn Pro Asn Glu Trp Trp Lys Val Tyr Pro
                115                 120                 125

Ser Ser Val Thr Glu Phe Lys Phe Leu Phe Val Ser Gly His Phe Lys
                130                 135                 140

Gly Asn Tyr Lys Ala Gln Leu Thr Arg Leu Asn Arg Lys Thr Asn Cys
 145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
                180                 185                 190

Asn Gly Glu Ile Asn Phe Ala Asp Pro Thr Asn Arg Ala Lys Gly Leu
                195                 200                 205

Glu Ala Val Ser Val Ala Ser Met Asn Leu Leu Ile Asp Asn Trp Ile
 210                 215                 220

Pro Val Arg Pro Arg Asn Gly Lys Val Gln Ile Ile Asn Leu Gln
 225                 230                 235                 240

Ser Leu Tyr Cys Ser Arg Asp Gln Trp Arg Leu Ser Leu Pro Arg Asp
                245                 250                 255

Asp Met Glu Leu Ala Ala Leu Ala Leu Leu Val Cys Ile Gly Gln Ile
                260                 265                 270

Ile Ala Pro Ala Lys Asp Asp Val Glu Phe Arg His Arg Ile Met Asn
                275                 280                 285

Pro Leu Thr Glu Asp Glu Phe Gln Gln Leu Ile Ala Pro Trp Ile Asp
                290                 295                 300

Met Phe Tyr Leu Asn His Ala Glu His Pro Phe Met Gln Thr Lys Gly
 305                 310                 315                 320

Val Lys Ala Asn Asp Val Thr Pro Met Glu Lys Leu Leu Ala Gly Val
                325                 330                 335

Ser Gly Ala Thr Asn Cys Ala Phe Val Asn Gln Pro Gly Gln Gly Glu
                340                 345                 350

Ala Leu Cys Gly Gly Cys Thr Ala Ile Ala Leu Phe Asn Gln Ala Asn
                355                 360                 365

Gln Ala Pro Gly Phe Gly Gly Phe Lys Ser Gly Leu Arg Gly Gly
                370                 375                 380

Thr Pro Val Thr Thr Phe Val Arg Gly Ile Asp Leu Arg Ser Thr Val
 385                 390                 395                 400

Leu Leu Asn Val Leu Thr Leu Pro Arg Leu Gln Lys Gln Phe Pro Asn
                405                 410                 415

Glu Ser His Thr Glu Asn Gln Pro Thr Trp Ile Lys Pro Ile Lys Ser
                420                 425                 430

Asn Glu Ser Ile Pro Ala Ser Ser Ile Gly Phe Val Arg Gly Leu Phe
                435                 440                 445

Trp Gln Pro Ala His Ile Glu Leu Cys Asp Pro Ile Gly Ile Gly Lys
                450                 455                 460
```

Cys Ser Cys Cys Gly Gln Glu Ser Asn Leu Arg Tyr Thr Gly Phe Leu
465                 470                 475                 480

Lys Glu Lys Phe Thr Phe Thr Val Asn Gly Leu Trp Pro His Pro His
            485                 490                 495

Ser Pro Cys Leu Val Thr Val Lys Lys Gly Glu Val Glu Lys Phe
        500                 505                 510

Leu Ala Phe Thr Thr Ser Ala Pro Ser Trp Thr Gln Ile Ser Arg Val
        515                 520                 525

Val Val Asp Lys Ile Ile Gln Asn Glu Asn Gly Asn Arg Val Ala Ala
        530                 535                 540

Val Val Asn Gln Phe Arg Asn Ile Ala Pro Gln Ser Pro Leu Glu Leu
545                 550                 555                 560

Ile Met Gly Gly Tyr Arg Asn Asn Gln Ala Ser Ile Leu Glu Arg Arg
                565                 570                 575

His Asp Val Leu Met Phe Asn Gln Gly Trp Gln Gln Tyr Gly Asn Val
                580                 585                 590

Ile Asn Glu Ile Val Thr Val Gly Leu Gly Tyr Lys Thr Ala Leu Arg
            595                 600                 605

Lys Ala Leu Tyr Thr Phe Ala Glu Gly Phe Lys Asn Lys Asp Phe Lys
610                 615                 620

Gly Ala Gly Val Ser Val His Glu Thr Ala Glu Arg His Phe Tyr Arg
625                 630                 635                 640

Gln Ser Glu Leu Leu Ile Pro Asp Val Leu Ala Asn Val Asn Phe Ser
                645                 650                 655

Gln Ala Asp Glu Val Ile Ala Asp Leu Arg Asp Lys Leu His Gln Leu
                660                 665                 670

Cys Glu Met Leu Phe Asn Gln Ser Val Ala Pro Tyr Ala His His Pro
                675                 680                 685

Lys Leu Ile Ser Thr Leu Ala Leu Ala Arg Ala Thr Leu Tyr Lys His
        690                 695                 700

Leu Arg Glu Leu Lys Pro Gln Gly Gly Pro Ser Asn Gly
705                 710                 715

<210> SEQ ID NO 22
<211> LENGTH: 2235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgcatcacc atcatcacca cccgaaaaaa aagcgcaaag tggatccgaa gaaaaaacgt    60
aaagttgaag atccgaaaga catggctcaa ctggttaaaa gcgaactgga agagaaaaaa   120
agtgaactgc gccacaaact gaaatatgtg ccgcatgaat atatcgagct gattgaaatt   180
gcacgtaatc cgacccagga tcgtattctg gaaatgaaag tgatggaatt ttttatgaaa   240
gtgtacggct atcgcggtga acatctgggt ggtagccgta accggatggg tgcaatttat   300
accgttggta gcccgattga ttatggtgtt attgttgata ccaaagccta tagcggtggt   360
tataatctgc cgattggtca ggcagatgaa atgcagcgtt atgtgaaaga aaatcagacc   420
cgcaacaaac atattaaccc gaatgaatgg tggaaagttt atccgagcag cgttaccgag   480
tttaaattcc tgtttgttag cggtcacttc aaaggcaact ataaagcaca gctgacccgt   540
ctgaatcgta aaaccaattg taatggtgca gttctgagcg ttgaagaact gctgattggt   600

-continued

```
ggtgaaatga ttaaagcagg caccctgacc ctggaagaag ttcgtcgcaa atttaacaat    660
ggcgaaatca actttgcgga tcccaccaac cgcgcgaaag cctggaagc ggtgagcgtg     720
gcgagcatga atttgcttat tgataactgg attcctgtac gcccgcgaaa cggggggaaa    780
gtccaaatca taaatctgca atcgctatac tgcagtagaa tcagtggcg attaagtttg     840
ccccgtgacg atatggaact ggccgcttta gcactgctgg tttgcattgg caaattatc    900
gccccggcaa agatgacgt tgaatttcga catcgcataa tgaatccgct cactgaagat    960
gagtttcaac aactcatcgc gccgtggata gatatgttct accttaatca cgcagaacat   1020
cccttatgc agaccaaagg tgtcaaagca atgatgtga ctccaatgga aaaactgttg    1080
gctggggtaa gcggcgcgac gaattgtgca tttgtcaatc aaccggggca gggtgaagca   1140
ttatgtggtg gatgcactgc gattgcgtta ttcaaccagg cgaatcaggc accaggtttt   1200
ggtggtggtt ttaaaagcgg tttacgtgga ggaacacctg taacaacgtt cgtacgtggg   1260
atcgatcttc gttcaacggt gttactcaat gtcctcacat tacctcgtct tcaaaaacaa   1320
tttcctaatg aatcacatac ggaaaaccaa cctacctgga ttaaacctat caagtccaat   1380
gagtctatac ctgcttcgtc aattgggttt gtccgtggtc tattctggca accagcgcat   1440
attgaattat gcgatcccat tgggattggt aaatgttctt gctgtggaca ggaaagcaat   1500
ttgcgttata ccggttttct taaggaaaaa tttaccttta cagttaatgg gctatggccc   1560
catccgcatt cccccttgtct ggtaacagtc aagaaggggg aggttgagga aaaatttctt   1620
gctttcacca cctccgcacc atcatggaca caaatcagcc gagttgtggt agataagatt   1680
attcaaaatg aaaatggaaa tcgcgtggcg gcggttgtga atcaattcag aaatattgcg   1740
ccgcaaagtc ctcttgaatt gattatgggg ggatatcgta ataatcaagc atctattctt   1800
gaacggcgtc atgatgtgtt gatgtttaat caggggtggc aacaatacgg caatgtgata   1860
aacgaaatag tgactgttgg tttgggatat aaaacagcct tacgcaaggc gttatatacc   1920
tttgcagaag ggtttaaaaa taaagacttc aaaggggccg gagtctctgt tcatgagact   1980
gcagaaaggc atttctatcg acagagtgaa ttattaattc ccgatgtact ggcgaatgtt   2040
aatttttccc aggctgatga ggtaatagct gatttacgag acaaacttca tcaattgtgt   2100
gaaatgctat ttaatcaatc tgtagctccc tatgcacatc atcctaaatt aataagcaca   2160
ttagcgcttg cccgcgccac gctatacaaa catttacggg agttaaaacc gcaaggaggg   2220
ccatcaaatg gctga                                                   2235
```

<210> SEQ ID NO 23
<211> LENGTH: 744
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met His His His His His His Pro Lys Lys Arg Lys Val Asp Pro
1               5                   10                  15

Lys Lys Lys Arg Lys Val Glu Asp Pro Lys Asp Met Ala Gln Leu Val
            20                  25                  30

Lys Ser Glu Leu Glu Glu Lys Lys Ser Glu Leu Arg His Lys Leu Lys
        35                  40                  45

Tyr Val Pro His Glu Tyr Ile Glu Leu Ile Glu Ile Ala Arg Asn Pro
    50                  55                  60
```

```
Thr Gln Asp Arg Ile Leu Glu Met Lys Val Met Glu Phe Phe Met Lys
 65                  70                  75                  80

Val Tyr Gly Tyr Arg Gly Glu His Leu Gly Gly Ser Arg Lys Pro Asp
                 85                  90                  95

Gly Ala Ile Tyr Thr Val Gly Ser Pro Ile Asp Tyr Gly Val Ile Val
            100                 105                 110

Asp Thr Lys Ala Tyr Ser Gly Gly Tyr Asn Leu Pro Ile Gly Gln Ala
            115                 120                 125

Asp Glu Met Gln Arg Tyr Val Lys Glu Asn Gln Thr Arg Asn Lys His
            130                 135                 140

Ile Asn Pro Asn Glu Trp Trp Lys Val Tyr Pro Ser Ser Val Thr Glu
145                 150                 155                 160

Phe Lys Phe Leu Phe Val Ser Gly His Phe Lys Gly Asn Tyr Lys Ala
                165                 170                 175

Gln Leu Thr Arg Leu Asn Arg Lys Thr Asn Cys Asn Gly Ala Val Leu
            180                 185                 190

Ser Val Glu Glu Leu Leu Ile Gly Gly Glu Met Ile Lys Ala Gly Thr
            195                 200                 205

Leu Thr Leu Glu Glu Val Arg Arg Lys Phe Asn Asn Gly Glu Ile Asn
210                 215                 220

Phe Ala Asp Pro Thr Asn Arg Ala Lys Gly Leu Glu Ala Val Ser Val
225                 230                 235                 240

Ala Ser Met Asn Leu Leu Ile Asp Asn Trp Ile Pro Val Arg Pro Arg
                245                 250                 255

Asn Gly Gly Lys Val Gln Ile Ile Asn Leu Gln Ser Leu Tyr Cys Ser
            260                 265                 270

Arg Asp Gln Trp Arg Leu Ser Leu Pro Arg Asp Asp Met Glu Leu Ala
            275                 280                 285

Ala Leu Ala Leu Leu Val Cys Ile Gly Gln Ile Ile Ala Pro Ala Lys
            290                 295                 300

Asp Asp Val Glu Phe Arg His Arg Ile Met Asn Pro Leu Thr Glu Asp
305                 310                 315                 320

Glu Phe Gln Gln Leu Ile Ala Pro Trp Ile Asp Met Phe Tyr Leu Asn
                325                 330                 335

His Ala Glu His Pro Phe Met Gln Thr Lys Gly Val Lys Ala Asn Asp
            340                 345                 350

Val Thr Pro Met Glu Lys Leu Leu Ala Gly Val Ser Gly Ala Thr Asn
            355                 360                 365

Cys Ala Phe Val Asn Gln Pro Gly Gln Gly Glu Ala Leu Cys Gly Gly
            370                 375                 380

Cys Thr Ala Ile Ala Leu Phe Asn Gln Ala Asn Gln Ala Pro Gly Phe
385                 390                 395                 400

Gly Gly Gly Phe Lys Ser Gly Leu Arg Gly Thr Pro Val Thr Thr
                405                 410                 415

Phe Val Arg Gly Ile Asp Leu Arg Ser Thr Val Leu Leu Asn Val Leu
            420                 425                 430

Thr Leu Pro Arg Leu Gln Lys Gln Phe Pro Asn Glu Ser His Thr Glu
            435                 440                 445

Asn Gln Pro Thr Trp Ile Lys Pro Ile Lys Ser Asn Glu Ser Ile Pro
            450                 455                 460

Ala Ser Ser Ile Gly Phe Val Arg Gly Leu Phe Trp Gln Pro Ala His
465                 470                 475                 480
```

Ile Glu Leu Cys Asp Pro Ile Gly Ile Gly Lys Cys Ser Cys Cys Gly
                485                 490                 495

Gln Glu Ser Asn Leu Arg Tyr Thr Gly Phe Leu Lys Glu Lys Phe Thr
            500                 505                 510

Phe Thr Val Asn Gly Leu Trp Pro His Pro His Ser Pro Cys Leu Val
        515                 520                 525

Thr Val Lys Lys Gly Glu Val Glu Lys Phe Leu Ala Phe Thr Thr
    530                 535                 540

Ser Ala Pro Ser Trp Thr Gln Ile Ser Arg Val Val Asp Lys Ile
545                 550                 555                 560

Ile Gln Asn Glu Asn Gly Asn Arg Val Ala Ala Val Asn Gln Phe
                565                 570                 575

Arg Asn Ile Ala Pro Gln Ser Pro Leu Glu Leu Ile Met Gly Gly Tyr
            580                 585                 590

Arg Asn Asn Gln Ala Ser Ile Leu Glu Arg Arg His Asp Val Leu Met
        595                 600                 605

Phe Asn Gln Gly Trp Gln Tyr Gly Asn Val Ile Asn Glu Ile Val
    610                 615                 620

Thr Val Gly Leu Gly Tyr Lys Thr Ala Leu Arg Lys Ala Leu Tyr Thr
625                 630                 635                 640

Phe Ala Glu Gly Phe Lys Asn Lys Asp Phe Lys Gly Ala Gly Val Ser
                645                 650                 655

Val His Glu Thr Ala Glu Arg His Phe Tyr Arg Gln Ser Glu Leu Leu
            660                 665                 670

Ile Pro Asp Val Leu Ala Asn Val Asn Phe Ser Gln Ala Asp Glu Val
        675                 680                 685

Ile Ala Asp Leu Arg Asp Lys Leu His Gln Leu Cys Glu Met Leu Phe
    690                 695                 700

Asn Gln Ser Val Ala Pro Tyr Ala His His Pro Lys Leu Ile Ser Thr
705                 710                 715                 720

Leu Ala Leu Ala Arg Ala Thr Leu Tyr Lys His Leu Arg Glu Leu Lys
                725                 730                 735

Pro Gln Gly Gly Pro Ser Asn Gly
            740

<210> SEQ ID NO 24
<211> LENGTH: 2235
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
atgcatcacc atcatcacca cccgaaaaaa aagcgcaaag tggatccgaa gaaaaaacgt      60
aaagttgaag atccgaaaga catggctcaa ctggttaaaa gcgaactgga agagaaaaaa     120
agtgaactgc gccacaaact gaaatatgtg ccgcatgaat atatcgagct gattgaaatt     180
gcacgtaatc cgacccagga tcgtattctg gaaatgaaag tgatggaatt ttttatgaaa     240
gtgtacggct atcgcggtga acatctgggt ggtagccgta accggatgg tgcaattat      300 accgttggta gcccgattga ttatggtgtt attgttgata ccaaagccta tagcggtggt     360
tataatctgc cgattggtca ggcagatgaa atggaacgtt atgtggaaga aaatcagacc     420
cgtgataaac atctgaatcc gatgaatgg tggaaagttt atccgagcag cgttaccgag      480
tttaaattcc tgtttgttag cggtcacttc aaaggcaact ataaagcaca gctgacccgt     540

```
ctgaatcata ttaccaattg taatggtgca gttctgagcg ttgaagaact gctgattggt    600
ggtgaaatga ttaaagcagg caccctgacc ctggaagaag ttcgtcgcaa atttaacaat    660
ggcgaaatca actttgcgga tcccaccaac cgcgcgaaag gcctggaagc ggtgagcgtg    720
gcgagcatga atttgcttat tgataactgg attcctgtac gcccgcgaaa cgggggggaaa    780
gtccaaatca taaatctgca atcgctatac tgcagtagag atcagtggcg attaagtttg    840
ccccgtgacg atatggaact ggccgcttta gcactgctgg tttgcattgg gcaaattatc    900
gccccggcaa agatgacgt tgaatttcga catcgcataa tgaatccgct cactgaagat     960
gagtttcaac aactcatcgc gccgtggata gatatgttct accttaatca cgcagaacat   1020
cccttatgc agaccaaagg tgtcaaagca atgatgtga ctccaatgga aaaactgttg     1080
gctggggtaa gcggcgcgac gaattgtgca tttgtcaatc aaccggggca gggtgaagca   1140
ttatgtggtg gatgcactgc gattgcgtta ttcaaccagg cgaatcaggc accaggtttt   1200
ggtggtggtt ttaaaagcgg tttacgtgga ggaacacctg taacaacgtt cgtacgtggg   1260
atcgatcttc gttcaacggt gttactcaat gtcctcacat tacctcgtct tcaaaaacaa   1320
tttcctaatg aatcacatac ggaaaaccaa cctacctgga ttaaacctat caagtccaat   1380
gagtctatac ctgcttcgtc aattgggttt gtccgtggtc tattctggca accagcgcat   1440
attgaattat gcgatcccat tgggattggt aaatgttctt gctgtggaca ggaaagcaat   1500
ttgcgttata ccggttttct taaggaaaaa tttacctttta cagttaatgg gctatggccc   1560
catccgcatt cccctttgtct ggtaacagtc aagaaagggg aggttgagga aaaatttctt   1620
gctttcacca cctccgcacc atcatggaca caaatcagcc gagttgtggt agataagatt   1680
attcaaaatg aaaatggaaa tcgcgtggcg gcggttgtga atcaattcag aaatattgcg   1740
ccgcaaagtc ctcttgaatt gattatgggg ggatatcgta ataatcaagc atctattctt   1800
gaacggcgtc atgatgtgtt gatgtttaat caggggtggc aacaatacgg caatgtgata   1860
aacgaaatag tgactgttgg tttgggatat aaaacagcct tacgcaaggc gttatatacc   1920
tttgcagaag ggtttaaaaa taaagacttc aaaggggccg gagtctctgt tcatgagact   1980
gcagaaaggc atttctatcg acagagtgaa ttattaattc ccgatgtact ggcgaatgtt   2040
aatttttccc aggctgatga ggtaatagct gatttacgag acaaacttca tcaattgtgt   2100
gaaatgctat ttaatcaatc tgtagctccc tatgcacatc atcctaaatt aataagcaca   2160
ttagcgcttg cccgcgccac gctatacaaa catttacggg agttaaaacc gcaaggaggg   2220
ccatcaaatg gctga                                                    2235
```

<210> SEQ ID NO 25
<211> LENGTH: 744
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met His His His His His His Pro Lys Lys Arg Lys Val Asp Pro
1               5                   10                  15

Lys Lys Lys Arg Lys Val Glu Asp Pro Lys Asp Met Ala Gln Leu Val
                20                  25                  30

Lys Ser Glu Leu Glu Glu Lys Lys Ser Glu Leu Arg His Lys Leu Lys
            35                  40                  45

-continued

```
Tyr Val Pro His Glu Tyr Ile Glu Leu Ile Glu Ile Ala Arg Asn Pro
 50                  55                  60

Thr Gln Asp Arg Ile Leu Glu Met Lys Val Met Glu Phe Phe Met Lys
 65                  70                  75                  80

Val Tyr Gly Tyr Arg Gly Glu His Leu Gly Gly Ser Arg Lys Pro Asp
                 85                  90                  95

Gly Ala Ile Tyr Thr Val Gly Ser Pro Ile Asp Tyr Gly Val Ile Val
            100                 105                 110

Asp Thr Lys Ala Tyr Ser Gly Gly Tyr Asn Leu Pro Ile Gly Gln Ala
        115                 120                 125

Asp Glu Met Glu Arg Tyr Val Glu Glu Asn Gln Thr Arg Asp Lys His
130                 135                 140

Leu Asn Pro Asn Glu Trp Trp Lys Val Tyr Pro Ser Ser Val Thr Glu
145                 150                 155                 160

Phe Lys Phe Leu Phe Val Ser Gly His Phe Lys Gly Asn Tyr Lys Ala
                165                 170                 175

Gln Leu Thr Arg Leu Asn His Ile Thr Asn Cys Asn Gly Ala Val Leu
            180                 185                 190

Ser Val Glu Glu Leu Leu Ile Gly Gly Glu Met Ile Lys Ala Gly Thr
        195                 200                 205

Leu Thr Leu Glu Glu Val Arg Arg Lys Phe Asn Asn Gly Glu Ile Asn
210                 215                 220

Phe Ala Asp Pro Thr Asn Arg Ala Lys Gly Leu Glu Ala Val Ser Val
225                 230                 235                 240

Ala Ser Met Asn Leu Leu Ile Asp Asn Trp Ile Pro Val Arg Pro Arg
                245                 250                 255

Asn Gly Gly Lys Val Gln Ile Ile Asn Leu Gln Ser Leu Tyr Cys Ser
            260                 265                 270

Arg Asp Gln Trp Arg Leu Ser Leu Pro Arg Asp Asp Met Glu Leu Ala
        275                 280                 285

Ala Leu Ala Leu Leu Val Cys Ile Gly Gln Ile Ile Ala Pro Ala Lys
290                 295                 300

Asp Asp Val Glu Phe Arg His Arg Ile Met Asn Pro Leu Thr Glu Asp
305                 310                 315                 320

Glu Phe Gln Gln Leu Ile Ala Pro Trp Ile Asp Met Phe Tyr Leu Asn
                325                 330                 335

His Ala Glu His Pro Phe Met Gln Thr Lys Gly Val Lys Ala Asn Asp
            340                 345                 350

Val Thr Pro Met Glu Lys Leu Leu Ala Gly Val Ser Gly Ala Thr Asn
        355                 360                 365

Cys Ala Phe Val Asn Gln Pro Gly Gln Gly Glu Ala Leu Cys Gly Gly
370                 375                 380

Cys Thr Ala Ile Ala Leu Phe Asn Gln Ala Asn Gln Ala Pro Gly Phe
385                 390                 395                 400

Gly Gly Gly Phe Lys Ser Gly Leu Arg Gly Thr Pro Val Thr Thr
                405                 410                 415

Phe Val Arg Gly Ile Asp Leu Arg Ser Thr Val Leu Leu Asn Val Leu
            420                 425                 430

Thr Leu Pro Arg Leu Gln Lys Gln Phe Pro Asn Glu Ser His Thr Glu
        435                 440                 445

Asn Gln Pro Thr Trp Ile Lys Pro Ile Lys Ser Asn Glu Ser Ile Pro
450                 455                 460

Ala Ser Ser Ile Gly Phe Val Arg Gly Leu Phe Trp Gln Pro Ala His
```

```
                465                 470                 475                 480
        Ile Glu Leu Cys Asp Pro Ile Gly Ile Gly Lys Cys Ser Cys Gly
                            485                 490                 495
        Gln Glu Ser Asn Leu Arg Tyr Thr Gly Phe Leu Lys Glu Lys Phe Thr
                        500                 505                 510
        Phe Thr Val Asn Gly Leu Trp Pro His Pro Ser Pro Cys Leu Val
                        515                 520                 525
        Thr Val Lys Lys Gly Glu Val Glu Lys Phe Leu Ala Phe Thr Thr
                    530                 535                 540
        Ser Ala Pro Ser Trp Thr Gln Ile Ser Arg Val Val Asp Lys Ile
        545                 550                 555                 560
        Ile Gln Asn Glu Asn Gly Asn Arg Val Ala Ala Val Val Asn Gln Phe
                            565                 570                 575
        Arg Asn Ile Ala Pro Gln Ser Pro Leu Glu Leu Ile Met Gly Gly Tyr
                        580                 585                 590
        Arg Asn Asn Gln Ala Ser Ile Leu Glu Arg Arg His Asp Val Leu Met
                    595                 600                 605
        Phe Asn Gln Gly Trp Gln Gln Tyr Gly Asn Val Ile Asn Glu Ile Val
            610                 615                 620
        Thr Val Gly Leu Gly Tyr Lys Thr Ala Leu Arg Lys Ala Leu Tyr Thr
        625                 630                 635                 640
        Phe Ala Glu Gly Phe Lys Asn Lys Asp Phe Lys Gly Ala Gly Val Ser
                            645                 650                 655
        Val His Glu Thr Ala Glu Arg His Phe Tyr Arg Gln Ser Glu Leu Leu
                        660                 665                 670
        Ile Pro Asp Val Leu Ala Asn Val Asn Phe Ser Gln Ala Asp Glu Val
                    675                 680                 685
        Ile Ala Asp Leu Arg Asp Lys Leu His Gln Leu Cys Glu Met Leu Phe
                690                 695                 700
        Asn Gln Ser Val Ala Pro Tyr Ala His His Pro Lys Leu Ile Ser Thr
        705                 710                 715                 720
        Leu Ala Leu Ala Arg Ala Thr Leu Tyr Lys His Leu Arg Glu Leu Lys
                        725                 730                 735
        Pro Gln Gly Gly Pro Ser Asn Gly
                    740

<210> SEQ ID NO 26
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gaattcacaa cggtgagcaa gtcactgttg gcaagccagg atctgaacaa taccgtcttg      60
ctttcgagcg ctagctctag aactagtcct cagcctaggc tcgttccga agctgtcttt     120 cgctgctgag ggtgacgatc ccgcataggc ggcctttaac tcggatcc                 168

<210> SEQ ID NO 27
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 27

```
gaattcacaa cggtgagcaa gtcactgttg gcaagccagg atctgaacaa taccgtcttt      60
tcgagcgcta gctctagaac tagtcctcag cctaggcctc gttcaagctg tctttcgctg     120
ctgagggtga cgatcccgca taggcggcct ttaactcgga tcc                       163
```

<210> SEQ ID NO 28
<211> LENGTH: 158
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gaattcacaa cggtgagcaa gtcactgttg gcaagccagg atctgaacaa taccgtcttc      60
gagcgctagc tctagaacta gtcctcagcc taggcctcga agctgtcttt cgctgctgag     120
ggtgacgatc ccgcataggc ggcctttaac tcggatcc                             158
```

<210> SEQ ID NO 29
<211> LENGTH: 153
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
gaattcacaa cggtgagcaa gtcactgttg gcaagccagg atctgaacaa taccgtcttg      60
cgctagctct agaactagtc ctcagcctag gcctaagctg tctttcgctg ctgagggtga     120
cgatcccgca taggcggcct ttaactcgga tcc                                  153
```

<210> SEQ ID NO 30
<211> LENGTH: 148
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
gaattcacaa cggtgagcaa gtcactgttg gcaagccagg atctgaacaa taccgtcttg      60
ctagctctag aactagtcct cagcctagga agctgtcttt cgctgctgag ggtgacgatc     120
ccgcataggc ggcctttaac tcggatcc                                        148
```

<210> SEQ ID NO 31
<211> LENGTH: 143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gaattcacaa cggtgagcaa gtcactgttg gcaagccagg atctgaacaa taccgtcttc      60
tctagaacta gtcctcagcc taggaagctg tctttcgctg ctgagggtga cgatcccgca     120
taggcggcct ttaactcgga tcc                                             143
```

<210> SEQ ID NO 32
<211> LENGTH: 41

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cttgcgctag ctctagaact agtcctcagc ctaggcctaa g                    41

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cttaggccta ggctgaggac tagttctaga gctagcgcaa g                    41

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cttgcgctag ctctagaact agctagtcct cagcctaggc ctaag               45

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cttaggccta ggctgaggac tagctagttc tagagctagc gcaag               45

<210> SEQ ID NO 36
<211> LENGTH: 1100
<212> TYPE: DNA
<213> ORGANISM: Homo sapiens

<400> SEQUENCE: 36
ggtggaacaa gatggattat caagtgtcaa gtccaatcta tgacatcaat tattatacat    60
cggagccctg ccaaaaaatc aatgtgaagc aaatcgcagc ccgcctcctg cctccgctct   120
actcactggt gttcatcttt ggttttgtgg gcaacatgct ggtcatcctc atcctgataa   180
actgcaaaag gctgaagagc atgactgaca tctacctgct caacctggcc atctctgacc   240 tgttttttcct tcttactgtc cccttctggg ctcactatgc tgccgcccag tgggactttg   300
gaaatacaat gtgtcaactc ttgacagggc tctattttat aggcttcttc tctggaatct   360
tcttcatcat cctcctgaca atcgataggt acctggctgt cgtccatgct gtgtttgctt   420
taaaagccag gacggtcacc tttggggtgg tgacaagtgt gatcacttgg gtggtggctg   480
tgtttgcgtc tctcccagga atcatctttta ccagatctca aaaagaaggt cttcattaca   540
cctgcagctc tcattttcca tacagtcagt atcaattctg gaagaatttc cagacattaa   600
agatagtcat cttggggctg gtcctgccgc tgcttgtcat ggtcatctgc tactcgggaa   660
```

| tcctaaaaac tctgcttcgg tgtcgaaatg agaagaagag gcacagggct gtgaggctta | 720 |
| tcttcaccat catgattgtt tattttctct tctgggctcc ctacaacatt gtccttctcc | 780 |
| tgaacacctt ccaggaattc tttggcctga ataattgcag tagctctaac aggttggacc | 840 |
| aagctatgca ggtgacagag actcttggga tgacgcactg ctgcatcaac ccatcatct | 900 |
| atgcctttgt cggggagaag ttcagaaact acctcttagt cttcttccaa aagcacattg | 960 |
| ccaaacgctt ctgcaaatgc tgttctattt tccagcaaga ggctcccgag cgagcaagct | 1020 |
| cagtttacac ccgatccact ggggagcagg aaatatctgt gggcttgtga cacggactca | 1080 |
| agtgggctgg tgacccagtc | 1100 |

```
<210> SEQ ID NO 37
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
```

| ccatggtaat acgactcact atagggagaa ttagctgatc tttaataata aggaaatgtt | 60 |
| acattaaggt tggtgggttg tttttatggg aaaaaatgct ttaagaacaa atgtatactt | 120 |
| ttagagagtt ccccgcgcca gcggggataa accgcaaaca cagcatggac gacagccagg | 180 |
| tacctagagt tccccgcgcc agcggggata accgcaaac acagcatgga cgacagccag | 240 |
| gtacctagag ttccccgcgc cagcggggat aaaccgcaaa cacagcatgg acgacagcca | 300 |
| ggtacctaga gttccccgcg ccagcgggga taaaccgaaa acaaaaggct cagtcggaag | 360 |
| actgggcctt tgttttaac cccttggggc tctaaacgg tcttgaggg gttttttggg | 420 |
| tacc | 424 |

```
<210> SEQ ID NO 38
<211> LENGTH: 424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
```

| ccatggtaat acgactcact atagggagaa ttagctgatc tttaataata aggaaatgtt | 60 |
| acattaaggt tggtgggttg tttttatggg aaaaaatgct ttaagaacaa atgtatactt | 120 |
| ttagagagtt ccccgcgcca gcggggataa accgtgtgat cacttgggtg gtggctgtgt | 180 |
| ttgcgtgagt tccccgcgcc agcggggata accgtgtga tcacttgggt ggtggctgtg | 240 |
| tttgcgtgag ttccccgcgc cagcggggat aaaccgtgtg atcacttggg tggtggctgt | 300 |
| gtttgcgtga gttccccgcg ccagcgggga taaaccgaaa acaaaaggct cagtcggaag | 360 |
| actgggcctt tgttttaac cccttggggc tctaaacgg tcttgaggg gttttttggg | 420 |
| tacc | 424 |

```
<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 39
aaggatgcca gtgataagtg aatgccatg tgggctgtca aaa                43

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaggatgcga gtgataagtg aatgccatg tgggctgtca aaa                43

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gccatgtggg ctgtcaaaa                                          19

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gaatgccatg tgggctgtca aaa                                     23

<210> SEQ ID NO 43
<211> LENGTH: 1604
<212> TYPE: PRT
<213> ORGANISM: Streptomyces sp.

<400> SEQUENCE: 43

Met Pro Asp Gln Leu Asn Ala Pro Thr Pro Leu Gly Asp Arg Leu Thr
1               5                   10                  15

Gly Ala Val Arg Thr Val Trp Ala Lys His Asp Arg Asp Thr Gly Lys
                20                  25                  30

Trp Leu Pro Leu Trp Arg His Met Thr Asp Ser Ala Ala Val Ala Gly
            35                  40                  45

Leu Leu Trp Asp His Trp Leu Pro Arg Asn Ile Lys Asp Leu Ile Ala
        50                  55                  60

Glu Pro Leu Pro Gly Gly Val Ala Asp Ala Arg Ser Leu Cys Val Trp
65                  70                  75                  80

Leu Ala Gly Thr His Asp Ile Gly Lys Ala Thr Pro Ala Phe Ala Cys
                85                  90                  95

Gln Val Asp Glu Leu Ala Gly Val Met Thr Ala Ala Gly Leu Asp Met
                100                 105                 110

Arg Thr Ser Lys Gln Leu Gly Glu Asp Arg Arg Met Ala Pro His Gly
            115                 120                 125

Leu Ala Gly Gln Val Leu Leu Gln Glu Trp Leu Glu Glu Arg Arg Gly
        130                 135                 140

Trp Thr His Arg Ala Ser Ala Gln Phe Ala Val Val Ala Gly Gly His

-continued

```
            145                 150                 155                 160
        His Gly Val Pro Pro Asp His Met Gln Leu His Asn Leu Asp Ala His
                        165                 170                 175
        Pro Glu Leu Leu Arg Thr Gln Gly Leu Ala Glu Ala Gln Trp Arg Ala
                    180                 185                 190
        Val Gln Asp Glu Leu Leu Asp Ala Cys Ala Leu Val Phe Gly Val Glu
                195                 200                 205
        Glu Arg Leu Asp Ala Trp Arg Thr Val Lys Leu Pro Gln Thr Val Gln
            210                 215                 220
        Val Leu Leu Thr Ala Thr Val Ile Val Ser Asp Trp Ile Ala Ser Asn
        225                 230                 235                 240
        Pro Asp Leu Phe Pro Tyr Phe Pro Glu Glu His Pro Arg Glu Glu Ala
                        245                 250                 255
        Glu Arg Val Ala Ala Ala Trp Gln Gly Leu Leu Leu Pro Ala Pro Trp
                    260                 265                 270
        Glu Pro Glu Glu Pro Ser Ala Pro Ala Ala Glu Phe Tyr Ala Ser Arg
                275                 280                 285
        Phe Ala Leu Pro Pro Gly Ala Val Arg Pro Val Gln Glu Gln Ala
            290                 295                 300
        Leu Ala Met Ala Arg Asp Met Glu Arg Pro Gly Met Leu Ile Ile Glu
        305                 310                 315                 320
        Ala Pro Met Gly Glu Gly Lys Thr Glu Ala Ala Leu Ala Val Ala Glu
                        325                 330                 335
        Val Phe Ala Ala Arg Ser Gly Ala Gly Gly Cys Tyr Val Ala Leu Pro
                    340                 345                 350
        Thr Met Ala Thr Ser Asn Ala Met Phe Pro Arg Leu Leu Arg Trp Leu
                355                 360                 365
        Asp Arg Leu Pro Arg Ala Asp Val Ser Gly Gly Arg Asp His Glu Gln
            370                 375                 380
        Arg Ser Val Leu Leu Ala His Ala Lys Ser Ala Leu Gln Glu Asp Tyr
        385                 390                 395                 400
        Ala Thr Leu Met Arg Glu Ser His Arg Thr Ile Ala Ala Val Asp Ala
                        405                 410                 415
        Tyr Gly Asp Asp Ser Arg Pro Arg Lys Gly Arg Pro Ala Ala Asp Gly
                    420                 425                 430
        Val Arg Arg Lys Ala Pro Ala Glu Leu Val Ala His Gln Trp Leu Arg
                435                 440                 445
        Gly Arg Lys Lys Gly Leu Leu Ala Ser Phe Ala Val Gly Thr Ile Asp
            450                 455                 460
        Gln Leu Leu Met Ala Gly Leu Lys Ser Arg His Leu Ala Leu Arg His
        465                 470                 475                 480
        Leu Ala Met Ala Gly Lys Val Val Val Ile Asp Glu Val His Ala Tyr
                        485                 490                 495
        Asp Thr Tyr Met Asn Ala Tyr Leu Asp Arg Val Leu Ala Trp Leu Gly
                    500                 505                 510
        Glu Tyr Arg Val Pro Val Val Leu Ser Ala Thr Leu Pro Ala Arg
                515                 520                 525
        Arg Arg Gly Glu Leu Ala Ala Tyr Thr Gly Glu Asp Ala Gln Ala
            530                 535                 540
        Leu Thr Glu Ala Thr Gly Tyr Pro Leu Leu Thr Ala Val Pro Gly
        545                 550                 555                 560
        Arg Glu Ala Val Gln Phe Val Ala Ala Ala Ser Gly Arg Gly Ser Asp
                        565                 570                 575
```

```
Val Leu Leu Glu Lys Leu Asp Asp Asp Glu Ala Leu Ala Asp Arg
            580                 585                 590

Leu Asp Thr Asp Leu Ala Asp Gly Gly Cys Ala Leu Val Val Arg Asn
            595                 600                 605

Thr Val Asp Arg Val Met Asp Thr Ala Ser Val Leu Arg Glu Arg Phe
    610                 615                 620

Gly Ala Asp His Val Thr Val Ala His Ala Arg Phe Val Asp Leu Asp
625                 630                 635                 640

Arg Ala Arg Lys Asp Ser Glu Leu Leu Ala Arg Phe Gly Pro Pro Asp
                645                 650                 655

Pro Asp Gly Gly Ser Pro Gln Arg Pro Arg Asn Ala His Ile Val Val
            660                 665                 670

Ala Ser Gln Val Ala Glu Gln Ser Leu Asp Val Asp Phe Asp Leu Leu
        675                 680                 685

Val Ser Asp Leu Cys Pro Val Asp Leu Leu Gln Arg Met Gly Arg
    690                 695                 700

Leu His Arg His Pro Arg Gly Arg Asp Gln Glu Arg Arg Pro Ala Arg
705                 710                 715                 720

Leu Arg Gln Ala Arg Cys Leu Val Thr Gly Val Gly Trp Asp Thr Ser
                725                 730                 735

Pro Ala Pro Glu Ala Asp Glu Gly Ser Arg Ala Ile Tyr Gly Ala Tyr
            740                 745                 750

Ser Leu Leu Arg Ser Leu Ala Val Leu Ala Pro His Leu Gly Thr Ala
        755                 760                 765

Gly Ala Ala Gly His Pro Leu Arg Leu Pro Glu Asp Ile Ser Pro Leu
    770                 775                 780

Val Arg Arg Ala Tyr Gly Glu Glu Asp Pro Cys Pro Pro Glu Trp Glu
785                 790                 795                 800

Pro Val Leu Ala Pro Ala Arg Asp Lys Tyr Arg Thr Ala Arg Glu Arg
                805                 810                 815

Gln Ser Gln Lys Ala Glu Val Phe Arg Leu Asp Glu Val Arg Lys Ala
            820                 825                 830

Gly Arg Pro Leu Ile Gly Trp Ile Asp Ala Gly Val Gly Asp Ala Asp
        835                 840                 845

Asp Thr Pro Val Gly Arg Ala Gln Val Arg Asp Thr Lys Glu Gly Leu
    850                 855                 860

Glu Val Leu Val Val Arg Arg Arg Ala Asp Gly Ser Leu Cys Thr Leu
865                 870                 875                 880

Pro Trp Leu Asp Lys Gly Arg Gly Gly Leu Glu Leu Pro Val Asp Ala
                885                 890                 895

Val Pro Ser Ala Leu Ala Ala Arg Ala Val Ala Ala Ser Gly Leu Arg
            900                 905                 910

Leu Pro Tyr His Phe Thr Ser Ser Pro Gln Thr Leu Asp Arg Thr Leu
        915                 920                 925

Ala Glu Leu Glu Glu Leu Tyr Val Pro Ala Trp Gln Glu Lys Glu Ser
    930                 935                 940

His Trp Ile Ala Gly Glu Leu Ile Leu Ala Leu Asp Glu Glu Gly Arg
945                 950                 955                 960

Ala Ala Leu Ala Gly Gln Gln Leu Val Tyr Asn Pro Glu Glu Gly Leu
                965                 970                 975

Leu Val Ala Ser Ala Asp Ala Asn Thr Glu Ala Thr Ser Gly Arg Val
            980                 985                 990
```

```
Met Asp Gly Lys Pro Ser Ser Ala Gly Asp Gly Lys Pro Gly His Ala
        995                 1000                1005

Ala Asp Gly Asn Arg Ala Arg Thr Thr Val Gly Gln Ser Pro Ala
    1010                1015                1020

Asp Arg Gln Thr His Gln Pro Pro Glu Gly Glu Arg His Pro Val
    1025                1030                1035

Pro Pro Ser Ala Ala Pro Pro Ala Arg Pro Ser Phe Asp Leu
    1040                1045                1050

Thr Ser Arg Pro Trp Leu Pro Val Leu Leu Lys Asp Gly Ser Glu
    1055                1060                1065

Arg Glu Leu Ser Leu Pro Glu Val Phe Asp Gln Ala Arg Asp Ile
    1070                1075                1080

Arg Arg Leu Val Gly Asp Leu Pro Thr Gln Asp Phe Ala Leu Thr
    1085                1090                1095

Arg Met Leu Leu Ala Leu Leu Tyr Asp Ala Leu Ser Glu Pro Gly
    1100                1105                1110

Gly Asp Met Ala Pro Ala Asp Thr Asp Ala Trp Glu Glu Leu Trp
    1115                1120                1125

Leu Ser Gln Ser Ala Tyr Ala Ala Pro Val Ala Ala Tyr Leu His
    1130                1135                1140

Arg Tyr Arg Glu Arg Phe Asp Leu Leu His Pro Glu Ser Pro Phe
    1145                1150                1155

Phe Gln Thr Pro Gly Leu Arg Thr Ala Lys Asn Glu Val Phe Ser
    1160                1165                1170

Leu Asn Arg Leu Val Ala Asp Val Pro Asn Gly Asp Pro Phe Phe
    1175                1180                1185

Ser Met Arg Arg Pro Gly Val Asp Arg Leu Gly Phe Ala Glu Ala
    1190                1195                1200

Ala Arg Trp Leu Val His Ala Gln Ala Tyr Asp Thr Ser Gly Ile
    1205                1210                1215

Lys Thr Gly Ala Val Gly Asp Pro Arg Val Lys Ala Gly Lys Gly
    1220                1225                1230

Tyr Pro Gln Gly Pro Ala Trp Ala Gly Asn Leu Gly Gly Val Leu
    1235                1240                1245

Leu Glu Gly Asp Asn Leu His Glu Thr Leu Leu Leu Asn Leu Ile
    1250                1255                1260

Ala Gly Asp Thr Pro Gly Val His Ala Ala Glu Val Asp Arg Pro
    1265                1270                1275

Ala Trp Arg Ala Glu Pro Ser Gly Pro Ala Pro Ala Pro Asp Leu
    1280                1285                1290

Gly Leu Arg Pro Tyr Gly Leu Arg Asp Leu Tyr Thr Trp Gln Ser
    1295                1300                1305

Arg Arg Ile Arg Leu His His Asp Ala Asp Gly Val His Gly Val
    1310                1315                1320

Val Leu Ala Tyr Gly Asp Ser Leu Glu Pro His Asn Arg His Gly
    1325                1330                1335

His Glu Pro Met Thr Ser Trp Arg Arg Ser Pro Thr Gln Glu Lys
    1340                1345                1350

Lys Arg Gln Glu Asn Leu Val Tyr Leu Pro Arg Glu His Asp Pro
    1355                1360                1365

Ser Arg Leu Ala Trp Arg Gly Met Asp Gly Leu Leu Ala Gly Arg
    1370                1375                1380

Glu Thr Gly Ser Ala Gln Gly Pro Asp Gly Ala Asp Arg Leu Ala
```

```
                   1385                1390                1395

Pro Lys Val Val Gln Trp Ala Ala Gln Leu Thr Thr Glu Gly Leu
    1400                1405                1410

Leu Pro Arg Gly Tyr Leu Ile Arg Thr Arg Val Ile Gly Ala Arg
    1415                1420                1425

Tyr Gly Thr Gln Gln Ser Val Ile Asp Glu Val Asp Asp Gly
    1430                1435                1440

Val Leu Met Pro Ala Val Leu His Glu Ala Asp Arg Arg Tyr
    1445                1450                1455

Gly Asp Lys Ala Val Asp Ala Leu His Asp Ala Glu Lys Ala Val
    1460                1465                1470

Gly Ala Leu Ala Gln Leu Ala Ala Asp Leu Ala Leu Ala Val Gly
    1475                1480                1485

Thr Asp Pro Glu Pro Gly Arg Asn Thr Ala Arg Asp Leu Gly Phe
    1490                1495                1500

Gly Thr Leu Asp Thr His Tyr Arg Arg Trp Leu Arg Glu Leu Gly
    1505                1510                1515

Gly Thr Ser Asp Pro Glu Glu His Arg Asp Arg Trp Lys Gln Glu
    1520                1525                1530

Val Arg Arg Leu Val Ala Glu Leu Gly Glu Arg Leu Leu Asp Gly
    1535                1540                1545

Ala Gly Pro Ala Ala Trp Glu Gly Arg Leu Val Glu Thr Gly Lys
    1550                1555                1560

Gly Thr Arg Trp Leu Asn Asp Ala Ala Ala Glu Leu Arg Phe Arg
    1565                1570                1575

Thr Arg Leu Arg Glu Phe Leu Thr Thr Ala Pro Asp Thr Pro Thr
    1580                1585                1590

Ser Pro Arg Pro Ala Pro Val Glu Ser Pro Ala
    1595                1600

<210> SEQ ID NO 44
<211> LENGTH: 1559
<212> TYPE: PRT
<213> ORGANISM: Streptomyces griseus

<400> SEQUENCE: 44

Met Ser Asn Thr Pro Met Ser Arg Asp His Pro Glu Ser Leu Ser Ala
1               5                   10                  15

Tyr Ala Arg Leu Ser Pro Val Ser Arg Thr Ala Trp Gly Lys His Asp
                20                  25                  30

Arg Gln Thr Glu Gln Trp Leu Pro Leu Trp Arg His Met Ala Asp Ser
            35                  40                  45

Ala Ala Val Ala Glu Arg Leu Trp Asp Gln Trp Val Pro Asp Asn Val
        50                  55                  60

Lys Ala Leu Ile Ala Asp Ala Phe Pro Gln Gly Ala Gln Asp Ala Arg
65                  70                  75                  80

Arg Val Ala Val Phe Leu Ala Cys Val His Asp Ile Gly Lys Ala Thr
                85                  90                  95

Pro Ala Phe Ala Cys Gln Val Asp Gly Leu Ala Asp Arg Met Arg Ala
            100                 105                 110

Ala Gly Leu Ser Met Pro Tyr Leu Lys Gln Phe Gly Leu Asp Arg Arg
        115                 120                 125

Met Ala Pro His Gly Leu Ala Gly Gln Leu Leu Leu Gln Glu Trp Leu
    130                 135                 140
```

```
Ala Glu Arg Phe Gly Trp Ser Glu Arg Ala Ser Gly Gln Phe Ala Val
145                 150                 155                 160

Val Ala Gly Gly His His Gly Thr Pro Asp His Gln His Ile His
                165                 170                 175

Asp Leu Gly Leu Arg Pro His Leu Leu Arg Thr Ala Gly Glu Ser Gln
                180                 185                 190

Asp Thr Trp Arg Ser Val Gln Asp Glu Leu Met Asp Ala Cys Ala Val
            195                 200                 205

Arg Ala Gly Val Gly Gly Arg Phe Gly Ala Trp Arg Ser Val Arg Leu
        210                 215                 220

Pro Gln Pro Val Gln Val Val Leu Thr Ala Ile Val Ile Val Ser Asp
225                 230                 235                 240

Trp Ile Ala Ser Ser Ser Glu Leu Phe Pro Tyr Asp Pro Ala Ser Trp
                245                 250                 255

Ser Pro Val Gly Pro Glu Gly Glu Gly Arg Arg Leu Thr Ala Ala Trp
                260                 265                 270

Gly Gly Leu Asp Leu Pro Gly Pro Trp Arg Ala Asp Gln Pro Asp Cys
            275                 280                 285

Thr Ala Ala Glu Leu Phe Gly Lys Arg Phe Asp Leu Pro Glu Gly Ala
        290                 295                 300

Gly Val Arg Pro Val Gln Glu Ala Val Arg Val Ala Gln Glu Leu
305                 310                 315                 320

Pro Gly Pro Gly Leu Leu Ile Ile Glu Ala Pro Met Gly Glu Gly Lys
                325                 330                 335

Thr Glu Ala Ala Phe Ala Ala Ala Glu Ile Leu Ala Ala Arg Thr Gly
                340                 345                 350

Ala Gly Gly Cys Leu Val Ala Leu Pro Thr Arg Ala Thr Gly Asp Ala
            355                 360                 365

Met Phe Pro Arg Leu Leu Arg Trp Leu Glu Arg Leu Pro Ser Asp Gly
        370                 375                 380

Pro Arg Ser Val Val Leu Ala His Ala Lys Ala Ala Leu Asn Glu Val
385                 390                 395                 400

Trp Ala Gly Met Thr Lys Ala Asp Arg Arg Lys Ile Thr Ala Val Asp
                405                 410                 415

Leu Asp Ser Gln Val Glu Asp Val Ser Ser Ala Gly Gly Ala Arg Arg
                420                 425                 430

Ala Asn Pro Ala Ser Leu His Ala His Gln Trp Leu Arg Gly Arg Lys
            435                 440                 445

Lys Ala Leu Leu Ser Ser Phe Ala Val Gly Thr Val Asp Gln Val Leu
450                 455                 460

Phe Ala Gly Leu Lys Ser Arg His Leu Ala Leu Arg His Leu Ala Val
465                 470                 475                 480

Ala Gly Lys Val Val Ile Val Asp Glu Val His Ala Tyr Asp Ala Tyr
                485                 490                 495

Met Ser Ala Tyr Leu Asp Arg Val Leu Glu Trp Leu Ala Ala Tyr Arg
            500                 505                 510

Val Pro Val Val Met Leu Ser Ala Thr Leu Pro Ala His Arg Arg Arg
        515                 520                 525

Glu Leu Ala Ala Ala Tyr Ala Gly Glu Glu Thr Pro Glu Leu Ala Asp
            530                 535                 540

Ala Leu Ala Leu Pro Asp Asp Ala Tyr Pro Leu Ile Thr Ala Val Ala
545                 550                 555                 560

Pro Gly Gly Leu Val Leu Thr Ala Arg Pro Glu Pro Ala Ser Gly Arg
```

```
            565                 570                 575
Arg Thr Glu Val Val Leu Glu Arg Leu Gly Asp Gly Pro Ala Leu Leu
            580                 585                 590

Ala Ala Arg Leu Asp Glu Glu Leu Arg Asp Gly Gly Cys Ala Leu Val
            595                 600                 605

Val Arg Asn Thr Val Asp Arg Val Leu Glu Ala Ala Glu His Leu Arg
            610                 615                 620

Ala His Phe Gly Ala Glu Ala Val Thr Val Ala His Ser Arg Phe Val
625                 630                 635                 640

Ala Ala Asp Arg Ala Arg Asn Asp Thr Val Leu Arg Glu Arg Phe Gly
            645                 650                 655

Pro Gly Gly Asp Arg Pro Ala Gly Pro His Ile Val Val Ala Ser Gln
            660                 665                 670

Val Val Glu Gln Ser Leu Asp Ile Asp Phe Asp Leu Leu Val Thr Asp
            675                 680                 685

Leu Ala Pro Val Asp Leu Val Leu Gln Arg Met Gly Arg Leu His Arg
            690                 695                 700

His Pro Arg Thr Arg Pro Pro Arg Leu Ser Arg Ala Arg Cys Leu Ile
705                 710                 715                 720

Thr Gly Val Glu Asp Trp His Ala Glu Arg Pro Val Pro Val Arg Gly
                    725                 730                 735

Ser Leu Ala Val Tyr Gln Gly Pro His Thr Leu Leu Arg Ala Leu Ala
            740                 745                 750

Val Leu Gly Pro His Leu Asp Gly Val Pro Leu Val Leu Pro Asp His
            755                 760                 765

Ile Ser Pro Leu Val Gln Ala Ala Tyr Asp Glu Arg Pro Val Gly Pro
            770                 775                 780

Ala His Trp Ala Pro Val Leu Asp Glu Ala Arg Arg Gln Tyr Leu Thr
785                 790                 795                 800

Arg Leu Ala Glu Lys Arg Glu Arg Ala Asp Val Phe Arg Leu Gly Pro
                    805                 810                 815

Val Arg Arg Pro Gly Arg Pro Leu Phe Gly Trp Leu Asp Gly Asn Ala
            820                 825                 830

Gly Asp Ala Asp Asp Ser Arg Thr Gly Arg Ala Gln Val Arg Asp Ser
            835                 840                 845

Glu Glu Ser Leu Glu Val Leu Val Val Gln Arg Arg Ala Asp Gly Arg
            850                 855                 860

Leu Thr Thr Val Ser Trp Leu Asp Gly Arg Gly Gly Leu Asp Leu
865                 870                 875                 880

Pro Glu His Ala Pro Pro Pro Arg Ala Ala Glu Val Val Ala Ala
                    885                 890                 895

Cys Ala Leu Thr Leu Pro Arg Ser Leu Thr His Pro Gly Val Ile Asp
            900                 905                 910

Arg Thr Ile Ala Glu Leu Glu Arg Phe Val Pro Ala Trp Gln Val
            915                 920                 925

Lys Glu Cys Pro Trp Leu Ala Gly Glu Leu Leu Val Leu Asp Glu
            930                 935                 940

Asp Cys Gln Thr Arg Leu Ser Gly Leu Glu Val His Tyr Ser Thr Asp
945                 950                 955                 960

Gln Gly Leu Arg Val Gly Ser Val Gly Thr Arg Ser Thr Asn Arg Ala
            965                 970                 975

Lys Gly Leu Glu Ala Val Ser Val Ala Ser Phe Asp Leu Val Ser Arg
            980                 985                 990
```

-continued

```
Pro Trp Leu Pro Val Gln Tyr Glu  Asp Gly Ala Thr Gly  Glu Leu Ser
        995              1000              1005

Leu Arg  Glu Val Phe Ala Arg  Ala Gly Glu Val Arg  Arg Leu Val
    1010             1015              1020

Gly Asp  Leu Pro Thr Gln Glu  Leu Ala Leu Leu Arg  Leu Leu Leu
    1025             1030              1035

Ala Ile  Leu Tyr Asp Ala Tyr  Asp Glu Ala Pro Gly  Arg Ser Gly
    1040             1045              1050

Gly Ala  Pro Ala Gln Leu Glu  Asp Trp Glu Ala Leu  Trp Asp Glu
    1055             1060              1065

Pro Asp  Ser Phe Ala Val Val  Ala Gly Tyr Leu Asp  Arg His Arg
    1070             1075              1080

Asp Arg  Phe Asp Leu Leu His  Pro Glu Arg Pro Phe  Phe Gln Val
    1085             1090              1095

Ala Gly  Leu His Thr Gln Lys  His Glu Val Ala Ser  Leu Asn Arg
    1100             1105              1110

Ile Val  Ala Asp Val Pro Asn  Gly Glu Ala Phe Phe  Ser Met Arg
    1115             1120              1125

Arg Pro  Gly Val His Arg Leu  Gly Leu Ala Glu Ala  Ala Arg Trp
    1130             1135              1140

Leu Val  His Thr His Ala Tyr  Asp Ala Ser Gly Ile  Lys Ser Gly
    1145             1150              1155

Met Glu  Gly Asp Ala Arg Val  Lys Gly Gly Lys Val  Tyr Pro Gln
    1160             1165              1170

Gly Val  Gly Trp Val Gly Gly  Leu Gly Gly Val Phe  Ala Glu Gly
    1175             1180              1185

Ala Ser  Leu Arg Glu Thr Leu  Leu Leu Asn Leu Ile  Pro Thr Asp
    1190             1195              1200

Glu Asp  Ile Leu Thr Ser Glu  Pro Lys Ala Asp Leu  Pro Val Trp
    1205             1210              1215

Arg Arg  Glu Thr Pro Pro Gly  Pro Gly Val Val Glu  Gly Asp Pro
    1220             1225              1230

Ser Ala  Pro Arg Pro Ala Gly  Pro Arg Asp Leu Tyr  Thr Trp Gln
    1235             1240              1245

Ser Arg  Arg Leu Leu Leu His  Thr Glu Gly Ser Asp  Ala Ile Gly
    1250             1255              1260

Val Val  Leu Gly Tyr Gly Asp  Pro Leu Ser Pro Ala  Asn Arg Gln
    1265             1270              1275

Lys Thr  Glu Pro Met Thr Gly  Trp Arg Arg Ser Pro  Ala Gln Glu
    1280             1285              1290

Lys Lys  Leu Gly Arg Pro Leu  Val Tyr Leu Pro Arg  Gln His Asp
    1295             1300              1305

Pro Gly  Arg Ala Ala Trp Arg  Gly Leu Ala Ser Leu  Leu Tyr Pro
    1310             1315              1320

Gln Gly  Glu Asp Gly Asp Thr  Thr Gly Arg Gly Thr  Asp Arg Ser
    1325             1330              1335

Arg Pro  Ala Gly Ile Val Arg  Trp Leu Ala Leu Leu  Ser Thr Glu
    1340             1345              1350

Gly Val  Leu Pro Lys Gly Ser  Leu Ile Arg Thr Arg  Leu Val Gly
    1355             1360              1365

Ala Val  Tyr Gly Thr Gln Gln  Ser Val Val Asp Asp  Val Val Asp
    1370             1375              1380
```

```
Asp Ser Ile Ala Leu Pro Val Val Leu Leu His Gln Asp Arg Arg
    1385               1390               1395

Leu His Gly Ala Val Ala Val Asp Ala Val Ala Asp Ala Glu Arg
    1400               1405               1410

Ala Val Ser Ala Leu Gly His Leu Ala Gly Asn Leu Ala Arg Ala
    1415               1420               1425

Ser Gly Ser Glu Ala Gly Pro Ala Thr Ala Thr Ala Arg Asp Gln
    1430               1435               1440

Gly Phe Gly Ala Leu Asp Gly Pro Tyr Arg Arg Trp Leu Val Asp
    1445               1450               1455

Leu Ala Glu Asp Thr Asp Leu Glu Arg Ala Arg Ala Ala Trp Arg
    1460               1465               1470

Asp Thr Val Arg Leu Val Val Leu Gly Ile Gly Arg Glu Leu Leu
    1475               1480               1485

Asp Ala Ala Gly Arg Ala Ala Ala Glu Gly Arg Val Ile Glu Leu
    1490               1495               1500

Pro Gly Val Gly Lys Arg Trp Ile Asp Ser Ser Arg Ala Asp Leu
    1505               1510               1515

Trp Phe Arg Thr Arg Ile Asn Arg Val Leu Pro Arg Pro Leu Pro
    1520               1525               1530

Glu Ala His Ala Pro Thr Ala Asp Ile His Ala Gly His Ala Val
    1535               1540               1545

Arg Ala Asp Glu Ala Leu Ser Glu Glu Thr Val
    1550               1555

<210> SEQ ID NO 45
<211> LENGTH: 1540
<212> TYPE: PRT
<213> ORGANISM: Catenulispora acidiphila

<400> SEQUENCE: 45

Met Phe Asn Val Gly Ser Thr Arg Cys Trp Gly Asp Gly Gly Leu Arg
1               5                   10                  15

Asn Ala Ala Glu Asp Leu Ser Ala Ala Thr Arg Ser Ala Trp Ala Lys
                20                  25                  30

Ser Asp Pro Asp Ser Gly Gln Ser Leu Ser Leu Ile Arg His Leu Ala
            35                  40                  45

Asp Ser Ala Ala Ile Ala Glu His Leu Trp Asp Gln Trp Leu Pro Asp
        50                  55                  60

His Val Lys Ser Leu Ile Ala Glu Gly Leu Pro Glu Gly Leu Val Asp
65                  70                  75                  80

Gly Arg Thr Leu Ala Val Trp Leu Ala Gly Thr His Asp Ile Gly Lys
                85                  90                  95

Leu Thr Pro Ala Phe Ala Cys Gln Cys Glu Pro Leu Ala Gln Ala Met
                100                 105                 110

Arg Glu Cys Gly Leu Asp Met Pro Thr Arg Thr Gln Phe Gly Asp Asp
            115                 120                 125

Arg Arg Val Ala Pro His Gly Leu Ala Gly Gln Val Leu Leu Arg Glu
        130                 135                 140

Trp Leu Met Glu Arg His Gly Trp Ser Gly Arg Ser Ala Asp Ala Phe
145                 150                 155                 160

Thr Val Ile Ala Gly Gly His Gly Val Pro Pro Ser Tyr Ser Gln
                165                 170                 175

Leu His Asp Leu Asp Ala Tyr Pro Glu Leu Leu Arg Thr Pro Gly Ala
                180                 185                 190
```

```
Ser Glu Gly Ile Trp Lys Ser Ser Gln His Glu Leu Leu Asp Ala Cys
        195                 200                 205

Ala Val Met Thr Gly Ala Ser Ser Arg Leu Ala His Trp Arg Gly Leu
        210                 215                 220

Arg Leu Ser Gln Gln Ala Gln Val Leu Leu Thr Gly Leu Val Ile Val
225                 230                 235                 240

Ala Asp Trp Ile Ala Ser Asn Thr Asp Leu Phe Pro Tyr Pro Ala Leu
                245                 250                 255

Gly Thr Gly Glu Ala Ala Ile Asp Pro Gly Lys Arg Val Glu Leu Ala
                260                 265                 270

Trp Arg Gly Leu Glu Leu Pro Ala Pro Trp Ala Pro Lys Tyr Leu Met
            275                 280                 285

Pro Gly Met Gln Gly Leu Leu Ala Ser Arg Phe Gly Leu Pro Ala Asp
            290                 295                 300

Ala Gln Leu Arg Pro Val Gln Met Ala Val Gln Leu Ala Ser Ala
305                 310                 315                 320

Asn Ala Ala Pro Gly Leu Leu Val Ile Glu Ala Pro Met Gly Glu Gly
                325                 330                 335

Lys Thr Glu Ala Ala Leu Leu Ala Ala Glu Ile Leu Ala Ala Arg Ser
            340                 345                 350

Gly Ala Gly Gly Val Phe Leu Ala Leu Pro Thr Gln Ala Thr Ser Asn
            355                 360                 365

Ala Met Phe Ala Arg Val Val Asn Trp Leu Arg Gln Val Pro Arg Glu
    370                 375                 380

Gly Val Ala Ser Val His Leu Ala His Gly Lys Ala Ala Leu Asp Asp
385                 390                 395                 400

Ala Phe Ala Ser Phe Leu Arg Ala Ala Pro Arg Leu Thr Ser Ile Asp
                405                 410                 415

Ala Asp Gly Tyr Ala Gly Glu Ala Asn Val Arg Arg Asp Arg Arg Ala
                420                 425                 430

Gly Ser Ala Asp Met Val Ala His Gln Trp Leu Arg Gly Arg Lys Lys
            435                 440                 445

Gly Ile Leu Ser Pro Phe Val Val Gly Thr Ile Asp Gln Leu Leu Phe
    450                 455                 460

Thr Gly Leu Lys Ser Arg His Leu Ala Leu Arg His Leu Ala Val Ala
465                 470                 475                 480

Gly Lys Val Val Val Ile Asp Glu Val His Ala Tyr Asp Ala Tyr Met
                485                 490                 495

Ser Val Tyr Leu Glu Arg Val Leu Ser Trp Leu Gly Ala Tyr Arg Val
            500                 505                 510

Pro Val Val Leu Leu Ser Ala Thr Leu Pro Ala Asp Arg Arg Gln Ala
            515                 520                 525

Leu Val Glu Ala Tyr Gly Gly Ile Thr Ser Glu Ala Leu Arg Asp Ala
530                 535                 540

Arg Glu Ala Tyr Pro Val Leu Thr Ala Val Thr Ile Gly Ala Pro Ala
545                 550                 555                 560

Gln Ala Val Gly Thr Glu Pro Ala Glu Gly Arg Arg Val Asp Val Asn
                565                 570                 575

Val Glu Ala Phe Asp Asp Leu Gly Arg Leu Ala Asp Arg Leu Glu
                580                 585                 590

Ala Glu Leu Val Asp Gly Gly Cys Ala Leu Ile Ile Arg Asn Thr Val
            595                 600                 605
```

```
Gly Arg Val Leu Gln Thr Ala Gln Gln Leu Arg Glu Arg Phe Gly Ala
610                 615                 620

Gly Gln Val Thr Val Ala His Ser Arg Phe Ile Asp Leu Asp Arg Ala
625                 630                 635                 640

Arg Lys Asp Ala Asp Leu Leu Ala Arg Phe Gly His Asp Gly Ala Arg
                645                 650                 655

Pro Arg Arg His Ile Val Val Ala Ser Gln Val Ala Glu Gln Ser Leu
                660                 665                 670

Asp Ile Asp Phe Asp Leu Leu Val Thr Asp Leu Ala Pro Ile Asp Leu
            675                 680                 685

Val Leu Gln Arg Met Gly Arg Val His Arg His His Arg Gly Gly Pro
690                 695                 700

Glu Gln Ser Glu Arg Pro Ser Leu Arg Thr Ala Arg Cys Leu Val
705                 710                 715                 720

Thr Gly Val Asp Trp Ala Gly Ile Pro Ser Ala Pro Ile Ala Gly Ser
                725                 730                 735

Val Ala Val Tyr Gly Leu His Pro Leu Leu Arg Ser Leu Ala Val Leu
                740                 745                 750

Gln Pro Tyr Leu Thr Gly Ser Ala Leu Thr Leu Pro Gly Asp Ile Asn
            755                 760                 765

Pro Leu Val Gln Cys Ala Tyr Ala Gln Ser Phe Val Ala Pro Thr Gly
770                 775                 780

Trp Gly Glu Ala Met Asp Ala Ala Gln Ala Glu His Met Ala His Ile
785                 790                 795                 800

Val Gln Gln Arg Glu Gly Ala Met Ala Phe Cys Leu Asp Glu Val Arg
                805                 810                 815

Gly Pro Gly Arg Ser Leu Ile Gly Trp Ile Asp Gly Val Gly Asp
                820                 825                 830

Ala Asp Asp Thr Arg Ala Gly Arg Ala Gln Val Arg Asp Ser Pro Glu
            835                 840                 845

Thr Ile Glu Val Leu Val Val Gln Arg Gly Ser Asp Gly Val Leu Arg
850                 855                 860

Thr Leu Pro Trp Leu Asp Arg Gly Arg Gly Leu Glu Leu Pro Thr
865                 870                 875                 880

Glu Ala Val Pro Pro Arg Ala Ala Arg Ala Ala Ala Ser Ala
                885                 890                 895

Leu Arg Leu Pro Gly Leu Phe Ala Lys Pro Trp Met Phe Asp Arg Val
                900                 905                 910

Leu Arg Glu Leu Glu Arg Glu Tyr His Glu Ala Trp Gln Ala Lys Glu
            915                 920                 925

Ser Ser Trp Leu Gln Gly Glu Leu Leu Leu Val Leu Asp Glu Glu Cys
930                 935                 940

Arg Thr Val Leu Ala Gly Tyr Glu Leu Ser Tyr Asn Pro Asp Asp Gly
945                 950                 955                 960

Leu Glu Met Val Met Pro Gly Pro His Ala Ala Val Val Arg Asp
                965                 970                 975

Lys Glu Ala Ser Asp Asp Lys Thr Ala Ser Phe Asp Leu Thr Ser Ala
            980                 985                 990

Pro Trp Leu Pro Val Leu Tyr Ala Asp Gly Met Gln Gly Val Leu Ser
                995                 1000                1005

Leu Arg Asp Val Phe Ala Gln Ser Asn Leu Ile Arg Arg Leu Val
            1010                1015                1020

Gly Asp Leu Pro Thr Gln Asp Phe Ala Leu Leu Arg Leu Leu Leu
```

```
              1025                1030                1035

Ala Val Leu Tyr Asp Ala Val Asp Gly Pro Arg Asp Gly Gln Asp
         1040                1045                1050

Trp Glu Asp Leu Trp Thr Ser Asp Asp Pro Phe Ala Ala Val Pro
         1055                1060                1065

Ala Tyr Leu Asp Ser His Arg Glu Arg Phe Asp Leu Leu His Pro
         1070                1075                1080

Ala Thr Pro Phe Tyr Gln Val Pro Gly Leu Gln Thr Ala Lys Gly
         1085                1090                1095

Glu Val Gly Pro Leu Asn Lys Ile Val Ala Asp Val Pro Asp Gly
         1100                1105                1110

Asp Pro Phe Leu Thr Met Arg Met Pro Gly Val Glu Gln Leu Ser
         1115                1120                1125

Phe Ala Glu Ala Ala Arg Trp Leu Val His Thr Gln Ala Phe Asp
         1130                1135                1140

Thr Ser Gly Ile Lys Ser Gly Val Val Gly Asp Pro Lys Ala Val
         1145                1150                1155

Asn Gly Lys Arg Tyr Pro Gln Gly Val Ala Trp Leu Gly Asn Leu
         1160                1165                1170

Gly Gly Val Phe Ala Glu Gly Asp Thr Leu Arg Gln Thr Leu Leu
         1175                1180                1185

Leu Asn Leu Ile Pro Ala Asp Thr Thr Asn Leu Gln Val Thr Ser
         1190                1195                1200

Ala Gln Asp Val Pro Ala Trp Arg Gly Thr Asn Gly Arg Ala Gly
         1205                1210                1215

Ser Asp His Ala Asp Ala Glu Pro Arg Val Pro Ala Gly Leu Arg
         1220                1225                1230

Asp Leu Tyr Thr Trp Gln Ser Arg Arg Ile Arg Leu Glu Tyr Asp
         1235                1240                1245

Thr Arg Gly Val Thr Gly Ala Val Leu Thr Tyr Gly Asp Glu Leu
         1250                1255                1260

Thr Ala His Asn Lys His Gly Val Glu Pro Met Thr Gly Trp Arg
         1265                1270                1275

Arg Ser Lys Pro Gln Glu Lys Lys Leu Gly Leu Ser Thr Val Tyr
         1280                1285                1290

Met Pro Gln Gln His Asp Pro Thr Arg Ala Ala Trp Arg Gly Ile
         1295                1300                1305

Glu Ser Leu Leu Ala Gly Ser Ala Gly Ser Gly Ser Ser Gln Thr
         1310                1315                1320

Gly Glu Pro Ala Ser His Tyr Arg Pro Lys Ile Val Asp Trp Leu
         1325                1330                1335

Gly Glu Leu Ala His His Gly Asn Leu Pro Ser Arg Gly Leu Ile
         1340                1345                1350

Arg Val Arg Thr Ser Gly Ala Val Tyr Gly Thr Gln Gln Ser Ile
         1355                1360                1365

Ile Asp Glu Val Val Ser Asp Glu Leu Thr Met Ala Val Val Leu
         1370                1375                1380

Leu His Glu Asp Asp Pro Arg Phe Gly Lys Ala Ala Val Thr Ala
         1385                1390                1395

Val Lys Asp Ala Asp Ser Ala Val Ala Ala Leu Gly Asp Leu Ala
         1400                1405                1410

Ser Asp Leu Ala Arg Ala Ala Gly Leu Asp Pro Glu Pro Glu Arg
         1415                1420                1425
```

Val Thr Ala Arg Asp Arg Ala Phe Gly Ala Leu Asp Gly Pro Tyr
    1430                1435                1440

Arg Arg Trp Leu Leu Asp Leu Gly Asn Ser Thr Asp Pro Ala Ala
    1445                1450                1455

Met Arg Ala Val Trp Gln Gly Arg Val Tyr Asp Ile Ile Ala Val
    1460                1465                1470

Gln Gly Gln Met Leu Leu Asp Ser Ala Gly Ser Ala Ala Ala Gln
    1475                1480                1485

Gly Arg Met Val Lys Thr Thr Arg Gly Glu Arg Trp Met Asp Asp
    1490                1495                1500

Ser Leu Ala Asp Leu Tyr Phe Lys Gly Arg Ile Ala Lys Ala Leu
    1505                1510                1515

Ser Ser Arg Leu Gly Lys Lys Pro Thr Asp Pro Gly Glu Pro Val
    1520                1525                1530

Gly Ile Gln Glu Asp Pro Ala
    1535                1540

<210> SEQ ID NO 46
<211> LENGTH: 1407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Glu Pro Phe Lys Tyr Ile Cys His Tyr Trp Gly Lys Ser Lys
1               5                   10                  15

Ser Leu Thr Lys Gly Asn Asp Ile His Leu Leu Ile Tyr His Cys Leu
                20                  25                  30

Asp Val Ala Ala Val Ala Asp Cys Trp Trp Asp Gln Ser Val Val Leu
                35                  40                  45

Gln Asn Thr Phe Cys Arg Asn Glu Met Leu Ser Lys Gln Arg Val Lys
    50                  55                  60

Ala Trp Leu Leu Phe Phe Ile Ala Leu His Asp Ile Gly Lys Phe Asp
65                  70                  75                  80

Ile Arg Phe Gln Tyr Lys Ser Ala Glu Ser Trp Leu Lys Leu Asn Pro
                85                  90                  95

Ala Thr Pro Ser Leu Asn Gly Pro Ser Thr Gln Met Cys Arg Lys Phe
                100                 105                 110

Asn His Gly Ala Ala Gly Leu Tyr Trp Phe Asn Gln Asp Ser Leu Ser
                115                 120                 125

Glu Gln Ser Leu Gly Asp Phe Phe Ser Phe Phe Asp Ala Ala Pro His
    130                 135                 140

Pro Tyr Glu Ser Trp Phe Pro Trp Val Glu Ala Val Thr Gly His His
145                 150                 155                 160

Gly Phe Ile Leu His Ser Gln Asp Gln Asp Lys Ser Arg Trp Glu Met
                165                 170                 175

Pro Ala Ser Leu Ala Ser Tyr Ala Ala Gln Asp Lys Gln Ala Arg Glu
                180                 185                 190

Glu Trp Ile Ser Val Leu Glu Ala Leu Phe Leu Thr Pro Ala Gly Leu
                195                 200                 205

Ser Ile Asn Asp Ile Pro Pro Asp Cys Ser Ser Leu Leu Ala Gly Phe
    210                 215                 220

Cys Ser Leu Ala Asp Trp Leu Gly Ser Trp Thr Thr Thr Asn Thr Phe

-continued

```
            225                 230                 235                 240

Leu Phe Asn Glu Asp Ala Pro Ser Asp Ile Asn Ala Leu Arg Thr Tyr
                245                 250                 255

Phe Gln Asp Arg Gln Gln Asp Ala Ser Arg Val Leu Glu Leu Ser Gly
                260                 265                 270

Leu Val Ser Asn Lys Arg Cys Tyr Glu Gly Val His Ala Leu Leu Asp
                275                 280                 285

Asn Gly Tyr Gln Pro Arg Gln Leu Gln Val Leu Val Asp Ala Leu Pro
            290                 295                 300

Val Ala Pro Gly Leu Thr Val Ile Glu Ala Pro Thr Gly Ser Gly Lys
305                 310                 315                 320

Thr Glu Thr Ala Leu Ala Tyr Ala Trp Lys Leu Ile Asp Gln Gln Ile
                    325                 330                 335

Ala Asp Ser Val Ile Phe Ala Leu Pro Thr Gln Ala Thr Ala Asn Ala
                340                 345                 350

Met Leu Thr Arg Met Glu Ala Ser Ala Ser His Leu Phe Ser Ser Pro
                355                 360                 365

Asn Leu Ile Leu Ala His Gly Asn Ser Arg Phe Asn His Leu Phe Gln
            370                 375                 380

Ser Ile Lys Ser Arg Ala Ile Thr Glu Gln Gly Gln Glu Glu Ala Trp
385                 390                 395                 400

Val Gln Cys Cys Gln Trp Leu Ser Gln Ser Asn Lys Lys Val Phe Leu
                405                 410                 415

Gly Gln Ile Gly Val Cys Thr Ile Asp Gln Val Leu Ile Ser Val Leu
                420                 425                 430

Pro Val Lys His Arg Phe Ile Arg Gly Leu Gly Ile Gly Arg Ser Val
            435                 440                 445

Leu Ile Val Asp Glu Val His Ala Tyr Asp Thr Tyr Met Asn Gly Leu
450                 455                 460

Leu Glu Ala Val Leu Lys Ala Gln Ala Asp Val Gly Gly Ser Val Ile
465                 470                 475                 480

Leu Leu Ser Ala Thr Leu Pro Met Lys Gln Lys Gln Lys Leu Leu Asp
                485                 490                 495

Thr Tyr Gly Leu His Thr Asp Pro Val Glu Asn Asn Ser Ala Tyr Pro
                500                 505                 510

Leu Ile Asn Trp Arg Gly Val Asn Gly Ala Gln Arg Phe Asp Leu Leu
            515                 520                 525

Ala His Pro Glu Gln Leu Pro Pro Arg Phe Ser Ile Gln Pro Glu Pro
            530                 535                 540

Ile Cys Leu Ala Asp Met Leu Pro Asp Leu Thr Met Leu Glu Arg Met
545                 550                 555                 560

Ile Ala Ala Ala Asn Ala Gly Ala Gln Val Cys Leu Ile Cys Asn Leu
                565                 570                 575

Val Asp Val Ala Gln Val Cys Tyr Gln Arg Leu Lys Glu Leu Asn Asn
                580                 585                 590

Thr Gln Val Asp Ile Asp Leu Phe His Ala Arg Phe Thr Leu Asn Asp
            595                 600                 605

Arg Arg Glu Lys Glu Asn Arg Val Ile Ser Phe Gly Lys Asn Gly
            610                 615                 620

Lys Arg Asn Val Gly Arg Ile Leu Val Ala Thr Gln Val Val Glu Gln
625                 630                 635                 640

Ser Leu Asp Val Asp Phe Asp Trp Leu Ile Thr Gln His Cys Pro Ala
                645                 650                 655
```

Asp Leu Leu Phe Gln Arg Leu Gly Arg Leu His Arg His His Arg Lys
            660                 665                 670

Tyr Arg Pro Ala Gly Phe Glu Ile Pro Val Ala Thr Ile Leu Leu Pro
        675                 680                 685

Asp Gly Glu Gly Tyr Gly Arg His Glu His Ile Tyr Ser Asn Val Arg
    690                 695                 700

Val Met Trp Arg Thr Gln Gln His Ile Glu Glu Leu Asn Gly Ala Ser
705                 710                 715                 720

Leu Phe Phe Pro Asp Ala Tyr Arg Gln Trp Leu Asp Ser Ile Tyr Asp
                725                 730                 735

Asp Ala Glu Met Asp Glu Pro Glu Trp Val Gly Asn Gly Met Asp Lys
            740                 745                 750

Phe Glu Ser Ala Glu Cys Glu Lys Arg Phe Lys Ala Arg Lys Val Leu
        755                 760                 765

Gln Trp Ala Glu Glu Tyr Ser Leu Gln Asp Asn Asp Glu Thr Ile Leu
    770                 775                 780

Ala Val Thr Arg Asp Gly Glu Met Ser Leu Pro Leu Pro Tyr Val
785                 790                 795                 800

Gln Thr Ser Ser Gly Lys Gln Leu Leu Asp Gly Gln Val Tyr Glu Asp
            805                 810                 815

Leu Ser His Glu Gln Gln Tyr Glu Ala Leu Ala Leu Asn Arg Val Asn
        820                 825                 830

Val Pro Phe Thr Trp Lys Arg Ser Phe Ser Glu Val Val Asp Glu Asp
    835                 840                 845

Gly Leu Leu Trp Leu Glu Gly Lys Gln Asn Leu Asp Gly Trp Val Trp
850                 855                 860

Gln Gly Asn Ser Ile Val Ile Thr Tyr Thr Gly Asp Glu Gly Met Thr
865                 870                 875                 880

Arg Val Ile Pro Ala Asn Pro Lys Gly Asp Pro Thr Asn Arg Ala Lys
            885                 890                 895

Gly Leu Glu Ala Val Ser Val Ala Ser Met Asn Leu Leu Ile Asp Asn
        900                 905                 910

Trp Ile Pro Val Arg Pro Arg Asn Gly Gly Lys Val Gln Ile Ile Asn
    915                 920                 925

Leu Gln Ser Leu Tyr Cys Ser Arg Asp Gln Trp Arg Leu Ser Leu Pro
930                 935                 940

Arg Asp Asp Met Glu Leu Ala Ala Leu Ala Leu Leu Val Cys Ile Gly
945                 950                 955                 960

Gln Ile Ile Ala Pro Ala Lys Asp Asp Val Glu Phe Arg His Arg Ile
            965                 970                 975

Met Asn Pro Leu Thr Glu Asp Glu Phe Gln Gln Leu Ile Ala Pro Trp
        980                 985                 990

Ile Asp Met Phe Tyr Leu Asn His Ala Glu His Pro Phe Met Gln Thr
    995                 1000                1005

Lys Gly Val Lys Ala Asn Asp Val Thr Pro Met Glu Lys Leu Leu
    1010                1015                1020

Ala Gly Val Ser Gly Ala Thr Asn Cys Ala Phe Val Asn Gln Pro
    1025                1030                1035

Gly Gln Gly Glu Ala Leu Cys Gly Gly Cys Thr Ala Ile Ala Leu
    1040                1045                1050

Phe Asn Gln Ala Asn Gln Ala Pro Gly Phe Gly Gly Phe Lys
    1055                1060                1065

Ser Gly Leu Arg Gly Gly Thr Pro Val Thr Phe Val Arg Gly
1070                1075                1080

Ile Asp Leu Arg Ser Thr Val Leu Leu Asn Val Leu Thr Leu Pro
    1085                1090                1095

Arg Leu Gln Lys Gln Phe Pro Asn Glu Ser His Thr Glu Asn Gln
    1100                1105                1110

Pro Thr Trp Ile Lys Pro Ile Lys Ser Asn Glu Ser Ile Pro Ala
    1115                1120                1125

Ser Ser Ile Gly Phe Val Arg Gly Leu Phe Trp Gln Pro Ala His
    1130                1135                1140

Ile Glu Leu Cys Asp Pro Ile Gly Ile Gly Lys Cys Ser Cys Cys
    1145                1150                1155

Gly Gln Glu Ser Asn Leu Arg Tyr Thr Gly Phe Leu Lys Glu Lys
    1160                1165                1170

Phe Thr Phe Thr Val Asn Gly Leu Trp Pro His Pro His Ser Pro
    1175                1180                1185

Cys Leu Val Thr Val Lys Lys Gly Glu Val Glu Glu Lys Phe Leu
    1190                1195                1200

Ala Phe Thr Thr Ser Ala Pro Ser Trp Thr Gln Ile Ser Arg Val
    1205                1210                1215

Val Val Asp Lys Ile Ile Gln Asn Glu Asn Gly Asn Arg Val Ala
    1220                1225                1230

Ala Val Val Asn Gln Phe Arg Asn Ile Ala Pro Gln Ser Pro Leu
    1235                1240                1245

Glu Leu Ile Met Gly Gly Tyr Arg Asn Asn Gln Ala Ser Ile Leu
    1250                1255                1260

Glu Arg Arg His Asp Val Leu Met Phe Asn Gln Gly Trp Gln Gln
    1265                1270                1275

Tyr Gly Asn Val Ile Asn Glu Ile Val Thr Val Gly Leu Gly Tyr
    1280                1285                1290

Lys Thr Ala Leu Arg Lys Ala Leu Tyr Thr Phe Ala Glu Gly Phe
    1295                1300                1305

Lys Asn Lys Asp Phe Lys Gly Ala Gly Val Ser Val His Glu Thr
    1310                1315                1320

Ala Glu Arg His Phe Tyr Arg Gln Ser Glu Leu Leu Ile Pro Asp
    1325                1330                1335

Val Leu Ala Asn Val Asn Phe Ser Gln Ala Asp Glu Val Ile Ala
    1340                1345                1350

Asp Leu Arg Asp Lys Leu His Gln Leu Cys Glu Met Leu Phe Asn
    1355                1360                1365

Gln Ser Val Ala Pro Tyr His His Pro Lys Leu Ile Ser Thr
    1370                1375                1380

Leu Ala Leu Ala Arg Ala Thr Leu Tyr Lys His Leu Arg Glu Leu
    1385                1390                1395

Lys Pro Gln Gly Gly Pro Ser Asn Gly
    1400                1405

<210> SEQ ID NO 47
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ccgtcttgcg ctagctctag aactagtcct cagcctaggc ctaagctgt          49

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 48

His His His His His His
1               5

<210> SEQ ID NO 49
<211> LENGTH: 15
<212> TYPE: PRT
<213> ORGANISM: Simian virus 40

<400> SEQUENCE: 49

Pro Lys Lys Lys Arg Lys Val Asp Pro Lys Lys Lys Arg Lys Val
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met His His His His His His
1               5
```